(12) United States Patent
Parinov et al.

(10) Patent No.: US 8,137,974 B2
(45) Date of Patent: Mar. 20, 2012

(54) TRANSPOSITION OF MAIZE AC/DS ELEMENTS IN VERTEBRATES

(75) Inventors: Sergey Parinov, Singapore (SG); Alexander Emelyanov, Singapore (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 619 days.

(21) Appl. No.: 11/914,711

(22) PCT Filed: May 11, 2006

(86) PCT No.: PCT/SG2006/000121
§ 371 (c)(1),
(2), (4) Date: Jun. 18, 2008

(87) PCT Pub. No.: WO2006/124001
PCT Pub. Date: Nov. 23, 2006

(65) Prior Publication Data
US 2009/0131272 A1   May 21, 2009

Related U.S. Application Data

(60) Provisional application No. 60/681,447, filed on May 17, 2005.

(51) Int. Cl.
*C12N 15/00* (2006.01)
*C12N 5/00* (2006.01)
*C07H 21/02* (2006.01)
*C07H 21/04* (2006.01)
*C12Q 1/00* (2006.01)

(52) U.S. Cl. ............ 435/455; 435/320.1; 435/325; 536/23.1; 536/23.2; 536/23.6; 530/327; 530/376

(58) Field of Classification Search ........... 435/320.1, 435/325, 455; 530/327, 376; 536/23.1, 23.2, 536/23.6
See application file for complete search history.

(56) References Cited

U.S. PATENT DOCUMENTS

| | | | |
|---|---|---|---|
| 6,271,436 B1 | 8/2001 | Piedrahita et al. | |
| 6,825,394 B1 | 11/2004 | Rudland et al. | |
| 2004/0003424 A1 | 1/2004 | Olson et al. | |
| 2004/0172667 A1* | 9/2004 | Cooper et al. | 800/19 |
| 2004/0197910 A1* | 10/2004 | Cooper et al. | 435/455 |
| 2004/0199938 A1 | 10/2004 | Perez et al. | |

FOREIGN PATENT DOCUMENTS

JP    2002-36691 A    12/2002

OTHER PUBLICATIONS

Tatsuka et al. (Electroporation-mediated transfection of mammalian cells with crude plasmid DNA preparations, 1995, Genetic Analysis: Biomolecular Engineering, vol. 12, pp. 113-117).*

Weil et al. (Transposition of Maize *Ac/Ds* transposable elements in the yeast *Saccharomyces cerevisiae*, 2000, Nature Genetics, vol. 26, pp. 187-190.*

Kunze et al. (Dominant transposition-deficient mutants of maize *Activator (Ac)* transposase, 1993, PNAS, vol. 90, pp. 7094-7098.*

Gong et al. (GENBANK, 2001, Accession No. AF440690, accessed on Oct. 15, 2010, SCORE alignment, 4 pages).*

Boehm et al. (One of three nuclear localization signals of maize *Activator (Ac)* transposase overlaps the DNA-binding domain, 1995, The Plant Journal, vol. 7, pp. 441-451).*

Kunze et al. (2) (PIR, 1988, accession No. T02916, accessed on Mar. 18, 2011, see attached SCORE alignment).*

Gong et al. (1) (Green fluorescent protein expression in germ-line transmitted transgenic zebrafish under a stratified epithelial promoter from Keratin8, 2002, Developmental Dynamics, vol. 223, pp. 204-215).*

Hamer, Lisbeth et al., "Recent advances in large-scale transposon mutagenesis," Current Opinion in Chemical Biology, vol. 5, No. 1, Feb. 2001, pp. 67-73, 7 pages.

Emelyanov, Alexander et al., "Trans-kingdom transposition of the maize Dissociation element," Genetics, vol. 174, No. 3, Nov. 2006, pp. 1095-1104, 10 pages.

European Communication dated Jul. 13, 2010, Extended European Search Report (Supplementary), Application No. 06748078.0-2405 / 1885856 PCT/SG2006000121, Temasek Life Sciences Laboratory Limited, 5 pages.

Kunze, R., et al., Proceedings of the National Academy of Sciences, (1993), 90:7094-7098, "Dominant transposition-deficient mutants of maize *Activator (Ac)* transposase."

Houba-Herin, N., et al., The Plant Journal (1994), 6(1):55-66, "Transposition of a *Ds* element from a plasmid into the plant genome in *Nicotiana plumbaginifolia* plortoplast-derived cells."

Weil, C.F., and Kunze, R.; Nature Genetics (2000), 26:187-190, "Transposition of maize *Ac/Dc* transposable elements in the yeast *Saccharomyces cerevisiae*."

Parinov, S., Developmental Dynamics (2004), 231:449-459, "Tol2 Transposon-mediated enhancer Trap to identify developmentally regulated zebrafish genes in vivo."

Fadool, J. et al., "Transposition of the mariner element from *Drosophila mauritiana* in zebrafish," Proceedings of the National Academy of Sciences of the United States of America, Apr. 1998, vol. 95, pp. 5182-5186, 5 pages.

Raz, E. et al., "Transposition of the nematode *Caenorhabditis elegans* Tc3 element in the zebrafish Danio rerio," Current Biology, Dec. 1997, vol. 8, pp. 82-88, 7 pages.

Japanese Office Action, Application No. 2008-512248, Mail date: Dec. 16, 2011, (translation attached), 5 pages.

* cited by examiner

*Primary Examiner* — Sue Liu
*Assistant Examiner* — Shannon Janssen
(74) *Attorney, Agent, or Firm* — Rothwell, Figg, Ernst & Manbeck P.C.

(57) ABSTRACT

The present invention is directed to the use of the maize Ac/Ds transposable elements in vertebrates.

31 Claims, 8 Drawing Sheets

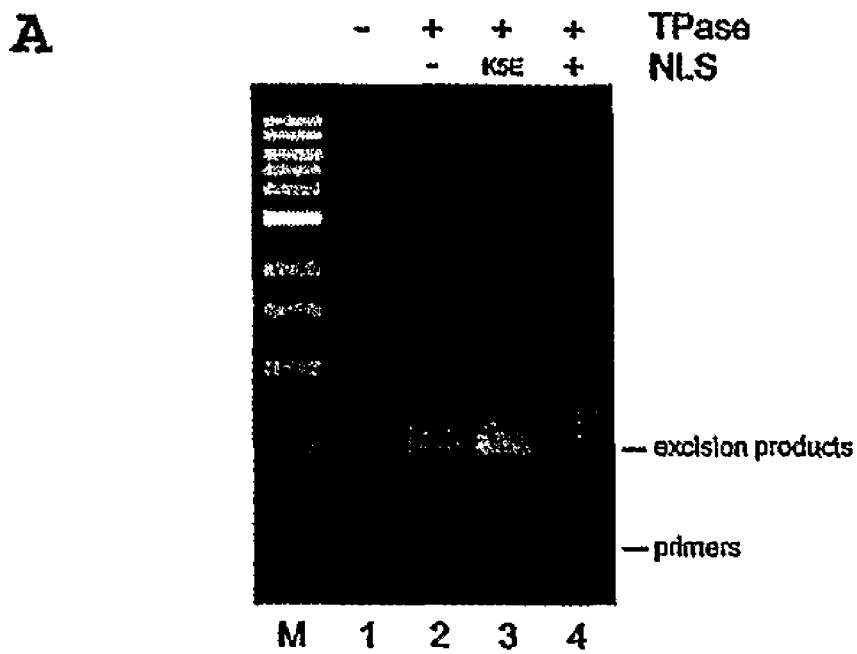

A

B

<u>Donor 1</u>

Before excision:
...GAGGATCCCCGACAtagggatgaaa-Ds-tttcatccctgCGTCGGGTATCGAG...

After excision:
...GAGGATCCCCGAC......................GGTCGGGTATCGAG...
...GAGGATCCCCGACT......................GTCGGGTATCGAG...

<u>Donor 2</u>

Before excision:
...TGGAGCTCCCCGACtagggatgaaa-Ds-tttcatccctgCGTCGGGTACCCAA...

After excision:
...TGGAGCTCCCCGA......................GTCGGGTACCCAA...
...TGGAGCTCCCCGAC......................GGTCGGGTACCCAA...

C

...CATGTT<u>GAACTGAC</u>tagggatgaaa-Ds-tttcatccctg<u>GAACTGAC</u>CGTCAT...
...TATATG<u>CTTTTCTT</u>tagggatgaaa-Ds-tttcatccctg<u>CTTTTCTT</u>CTGCTG...

Figure 2

- DNA 1 -

Homo sapiens chromosome 17, clone hRPK.294_J_22, AC005921.3 GI:4982556

A7 (Ds5'-122331-... +\-):   5'
atcggttatacgatacggtcggtacgggattttcccatcctactttcatccctgAGTGAGACTCTGACGGCCTCCTGCT
TCCCCCACACTGTGGAAGGTGGGGCTCCCCAAGCCTGCACTCCTACCTGAGATGCC
AGTCTCTTTGTCTACTTTAGACACCAGGTTCCAAAGACCCTGTGCTCTCAGATACCT
TTTATGTCTAAAGCAGAGGCCCTACCCCAGCACTCCCCATCTCAGTAGACAGTAACT
CCATTTACCA (SEQ ID NO:56)

D4 (...-122331-Ds5' +\+):   5'rev,
AGCACAGGGTCTTTGGAACCTGGTGTCTAAAGTAGACAAAGAGACTGGCATCTCAG
GTAGGAGTGCAGGCTTGGGGAGCCCCACCTTCCACAGTGTGGGGGAAGCAGGAGG
CCGTCAGAGTCTCACTcagggatgaaagtaggatgggaaaatcccgtaccgaccgttatcgtataaccgattttgttagtttta
tcccgatcgatttcgaacccgaggtaaaaaacgaaaacggaacggaaacggatataca (SEQ ID NO:57)

D5 (...-122331-Ds5' +\+):   5'rev,
GGGCCTCTGCTTTAGACATAAAAGGTATCTGAGAGCACAGGGTCTTTGGAACCTGG
TGTCTAAAGTAGACAAAGAGACTGGCATCTCAGGTAGGAGTGCAGGCTTGGGGAGC
CCCACCTTCCACAGTGTGGGGGAAGCAGGAGGCCGTCAGAGTCTCACTcagggatgaaagt
aggatgggaaaatcccgtaccgaccgttatcgtataaccgattttgttagttttatcccgatcgatttcgaacccgaggtaaaaacg (SEQ
ID NO:58)

D6 (...-122331-Ds5' +\+):   5'rev,
GCTTTAGACATAAAAGGTATCTGAGAGCACAGGGTCTTTGGAACCTGGTGTCTAAA
GTAGACAAAGAGACTGGCATCTCAGGTAGGAGTGCAGGCTTGGGGAGCCCCACCTT
CCACAGTGTGGGGGAAGCAGGAGGCCGTCAGAGTCTCACTcagggatgaaagtaggatgggaaa
atcccgtaccgaccgttatcgtataaccgattttgttagttttatcccgatcgatttcgaacccgaggtaaaaaacgaaaacggaacga
(SEQ ID NO:59)

D7 (...-122324-Ds3' +/+):   3'rev,
ACTGGCAACACCGCCTCTTGTTCTCCTCTATTTCCAGCATCCAGAAAAGTGTCTGGC
TTATCCTTGGTGCTCCATAAATTTTACTGAATGAATGAATAAATGAATTCATGAAT
GAACAGGATGGCTAGTGAGACtagggatgaaaacggtcggtaacggtcggtaaaatacctctaccgttttcattttcata
tttaacttgcgggacggaaacgaaaacgggatataccggtaacgaaaacgaacggg (SEQ ID NO:60)

D9 (...-122324-Ds3' +/+):   3'rev,
GACTGGCAACACCGCCTCTTGTTCTCCTCTATTTCCAGCATCCAGAAAAGTGTCTGG
CTTATCCTTGGTGCTCCATAAATTTTACTGAATGAATGAATAAATGAATTCATGAA
TGAACAGGATGGCTAGTGAGACtagggatgaaaacggtcggtaacggtcggtaaaatacctctaccgttttcattttcat
atttaacttgcgggacggaaacga (SEQ ID NO:61)

Figure 6A

DNA 2 insertion site:

GGAAGCAGGAGGCCGTCAGA*GTCTCACT*cagggatgaaagtagg...5'-Ds-3'...accgttttcatccc ta*GT CTCACT*AGCCATCCTGTTCATTCATG (SEQ ID NO:62....5'-Ds-3'...SEQ ID NO:63)

- DNA 2 -

Homo sapiens chromosome 17, clone RP11-219F9  AC046170.6  GI:17488726

1A2-1 (Ds3'-23951-... +\-): 3'
aatatgaaaatgaaaacggtagaggtattttaccgaccgttaccgaccgttttcatccctaTATAGATGCATGTTTAGAGA
GGACTGAGGGGGCAACTGAATGTGTTTAATTTCAAGCTTACTATGTGATCATGAAAT
ACCCAACACATTATGCTGGTACAAATCCAGAGTTCTAAACTGAGACCGAGGTGGCA
TATGCATATTTGAGAGTTAGCAGCATAAAGATACTAATTGAAGCTATGAAACAGAT
GTGATTAATTTGGAGGAGAATAATTAGAGAAAAATAATAGGTCAAAGACAGACTCC
TGAGGAACCCCAACATTTTAAGGGACACAAAAGAGGTTGAAAAGAGACAGCCAGA
GAGGTAAAAGGAAAACCAGAAATGCTTGGAGTGAGAAAAGCCAAGTAAAGAGGGT
ATTTCAAGCAAAAGTAGTCAACAGTGTGTTTCCTAAACACGTGCAGACTGATTGGA
AGCTAGA (SEQ ID NO:64)

1A2-2 (...-23951-Ds3' +\+): 3'rev:
CTGTTGACTACTTTTGCTTGAATACCCTCTTTACTTGGCTTTTCTCACTCCAAGCATT
TCTGGTTTTCCTTTTACCTCTCTGGCTGTCTCTTTTCAACCTCTTTTGTGTCCCTTAAA
ATGTTGGGGTTCCTCAGGAGTCTGTCTTTGACCTATTATTTTTCTCTAATTATTCTCC
TCCAAATTAATCACATCTGTTTCATAGCTTCAATTAGTATCTTTATGCTGCTAACTCT
CAAATATGCATATGCCACCTCGGTCTCAGTTTACAACTCTGGATTTGTACCAGCATA
ATGTGTTGGGTATTTCATGATCACATAGTAAGCTTGAAATTAAACACATTCAGTTGC
CCCCTCAGTCCTCTCTAAACATGCATCTATAtagggatgaaaacggtcggtaacggtcggtaaaatacctcta
ccgttttcattttcatatttaacttgcgggacggaaacgaaaacgggatataccggtaacgaaaacgaacgggataaatac (SEQ ID NO:65)

Figure 6B

- DNA 3 -

Homo sapiens chromosome 18, clone RP11-813B21 AC090330.22 GI:24137587

B7 (Ds3'-17490-... +/+):    3'
tccgtcccgcaagttaaatatgaaaatgaaaacggtagaggtattttaccgaccgttaccgaccgttttcatccctaGTGAGAGTCT
GCTCTTCTGTAAACAGACGGCTGAAATTGCTGAAAATCAGACACAAGCTGTTACTA
TGCAAGTGATTGACCTGCAACGAAAGGTACATGCTCAGCCTCACTGGATGTCTACT
GTTAAAGGGAGGACATTGATTGGAAAAGAGTGGGACCCTGAAAGTTGAGATGGGG
ACACGTCGAGGGGCCCTAATGAAGCTGGGAATACTGAGATAATAAATTCTGATGAG
CCTTTTTAGCAAGAGGGAATCGCCTCCCCACCCCCAGTGGTAGAAACATGCCCTTGC
CCATCTACTGCAGTACCAGGCTTTCA (SEQ ID NO:66)

B10 (Ds3'-17490-... +/+):    3'
atatgaaaatgaaaacggtagaggtattttaccgaccgttaccgaccgttttcatccctaGTGAGAGTCTGCTCTTCTGTA
AACAGACGGCTGAAATTGCTGAAAATCAGACACAAGCTGTTACTATGCAAGTGATT
GACCTGCAACGAAAGGTACATGCTCAGCCTCACTGGATGTCTACTGTTAAAGGGAG
GACATTGATTGGAAAAGAGTGGGACCCTGAAAGTTGAGATGGGGACACGTCGAGG
GGCCCTAATGAAGCTGGGAATACTGAGATAATAAATTCTGATGAGCCTTTTTAGCA
AGAGGGAATCGCCTCCCCACCCCCAGTGGTAGAAACATGCCCTTGCCCATCTACTG
CA (SEQ ID NO:67)

Figure 6C

SEQUENCE LISTING

<160> NUMBER OF SEQ ID NOS: 71

<210> SEQ ID NO 1
<211> LENGTH: 3998
<212> TYPE: DNA

<213> ORGANISM: Artificial
<220> FEATURE:
<223> OTHER INFORMATION: Ds Construct

<400> SEQUENCE: 1

```
ccatggtggc gaccggtgct cgactctaga ggatccccga catagggatg aaaacggtcg      60
gtaacggtcg gtaaaatacc tctaccgttt tcattttcat atttaacttg cgggacggaa     120
acgaaaacgg gatataccgg taacgaaaac gaacgggata aatacggtaa tcgaaaaccg     180
atacgatccg gtcgggttaa agtcgaaatc ggacgggaac cggtattttt gttcggtaaa     240
atcacacatg aaaacatata ttcaaaactt aaaaacaaat ataaaaatt gtaaacacaa      300
gtcttaatta acatagata aaatccatat aaatctggag cacacatagt ttaatgtagc      360
acataagtga taagtcttgg gctcttggct aacataagaa gccatataag tccctcgacc     420
tctagcttcg aattcccttc ccttctactt ttgacgtcct tttaagagct tgtgcatgaa     480
agcagatttg gagctgatta ctcatctcaa acacccatac aaagggatga ttgccgtacc     540
atgatctcac acctttcaca cctggtttat actatgatag ttgtagacga ttgcgtaatg     600
ctattaaatg cccatcagtg ctggctgtga cacccaactg ctgccatttc gtgttgactt     660
gcacgagaaa tgagaaattg tctgactatg cagggtgtct atgcgtggga acatttatca     720
gtggtcatta aatactatag tttacagtta gaccaaagtg tgctgtattt ttgtgttagc     780
ttagctgcag ttttttgtgtg tgaagtaaca aatgacaaat actcaaacta ttgtaattaa    840
gtagttttc tcagaaattg taatttacta agtagtttaa aaatgtgtac ttttactttc      900
ccttgagtac atttttagtg cagtgttggt acttttattt cacttccttc cttcaacctg     960
cagtcactac tttatttatt cttgtctatg tggattagac aaatcagtcc tgtgattcct    1020
gtccaatcaa attgcacata gaaggtaaat cacatcataa tgaactacct taagacatgg    1080
gccatttata attgcagcaa actgtttgcc agcattaaaa gaagatgtca aaatatttta   1140
cacgcattaa cccagagact gcttagatgc atgtcactga tgagaagatg atggatgttt    1200
actgtatgat gaccgaaata actttaaacg cacacaagac ggcacaagac gtcaacatgg    1260
cgttaggttg acgttgtacc ccaacgcagt ggggacgttg catttgtttt agaaatgaaa    1320
attaggttga cgtcagaact caacgtcagg tcgatgtcaa tgttcaacat ccaatctaaa    1380
atcatatatc aatgtctaat gatgttacag cttgatgtta tgcggatgtt accctatga     1440
cgtctatcag acgttggatt atggttgcca tacctgatga ataaatgtca ttatttgacg    1500
ttggtttaag atgttggttc gacattggat tttggtcgct ttccaacaca acctaaatcc    1560
accaaatatt aacttcctat gacatcgtta ttggacgtca aaataacaat atccttagat    1620
gctggctaga ctttgaattt aggtcaccac aacctatatt taacctaata ttaacatctt    1680
atgatgttgt gtgcctgctg ggcaataact aaatgcacta cagaatgtta cgtttacaca    1740
catgtaaatt acatgtaaat gcatcagctt ttcacagcat aatactcact acttactact    1800
cttgagtact tttaaaaaag ctacttttca ctcatacttt gagtaatatt tacaactgat    1860
acttttactc gcactacatt tttaggcatg tattgatatt tttactatga ttttcagta    1920
ctctttccac tactgcagcc ctccccatac ataatcgtat gtttacacat atggtggagt   1980
ttagagccat aatctacatt agctttgtta gccgctagca ttactgtgca gaattgtgtg   2040
tgtgcacatt ttccaatatc aatacagaag gaaactgtgt tccctgttcc cttgtaaatc   2100
tcaacaatgc aactgttcag ctcagggggga aaaatgccct gccagatcca aacggctggc   2160
aaaagtgaat ggaaaaaagc ctttcattaa tgtgaaagtt gctgcgcgcc ccacccagat   2220
```

-continued

| | |
|---|---|
| aaaaagagca gaggttaaca tgctctctac ggctgtccag ccaaccagat actgaggcag | 2280 |
| aaacacaccc gctggcagat ggtgagagct acactgtctt ttccagagtt tctactggaa | 2340 |
| tgcctgtcct caagtctcaa gcctctcctt gcattctctc attccacctg gggcaaagcc | 2400 |
| ccaggctggg tgtgacaaca tttatcttac cactttctct ctgtacctgt ctaacaggta | 2460 |
| gggtgtgtgt gagagtgcgt atgtgtgcaa gtgcgtgtgt gtgtgagagc agtcagctcc | 2520 |
| accctctcaa gagtgtgtat aaaattggtc agccagctgc tgagagacac gcagagggac | 2580 |
| tttgactctc ctttgtgagc aacctcctcc actcactcct ctctcagaga gcactctcgt | 2640 |
| acctccttct cagcaactca agacacagg atccaccggt cgccaccatg gtgagcaagg | 2700 |
| gcgaggagct gttcaccggg gtggtgccca tcctggtcga gctggacggc gacgtaaacg | 2760 |
| gccacaagtt cagcgtgtcc ggcgagggcg agggcgatgc cacctacggc aagctgaccc | 2820 |
| tgaagttcat ctgcaccacc ggcaagctgc ccgtgccctg gcccaccctc gtgaccaccc | 2880 |
| tgacctacgg cgtgcagtgc ttcagccgct accccgacca catgaagcag cacgacttct | 2940 |
| tcaagtccgc catgcccgaa ggctacgtcc aggagcgcac catcttcttc aaggacgacg | 3000 |
| gcaactacaa gacccgcgcc gaggtgaagt tcgagggcga caccctggtg aaccgcatcg | 3060 |
| agctgaaggg catcgacttc aaggaggacg gcaacatcct ggggcacaag ctggagtaca | 3120 |
| actacaacag ccacaacgtc tatatcatgg ccgacaagca gaagaacggc atcaaggtga | 3180 |
| acttcaagat ccgccacaac atcgaggacg gcagcgtgca gctcgccgac cactaccagc | 3240 |
| agaacacccc catcggcgac ggccccgtgc tgctgcccga caaccactac ctgagcaccc | 3300 |
| agtccgccct gagcaaagac cccaacgaga agcgcgatca catggtcctg ctggagttcg | 3360 |
| tgaccgccgc cgggatcact ctcggcatgg acgagctgta caagtaaagc ggccgcgact | 3420 |
| ctagatcata atcagccata ccacatttgt agaggttcta cttgctttaa aaaacctccc | 3480 |
| acacctcccc ctgaacctga aacataaaat gaatgcaatt gttgttgtta acttgtttat | 3540 |
| tgcagcttat aatggttaca aataaagcaa tagcatcaca aatttcacaa ataaagcatt | 3600 |
| tttttcactg cattctagtt gtggtttgtc caaactcatc aatgtgcgag gatctgttg | 3660 |
| cagtcatccc gaattagaaa atacggtaac gaaacgggat catcccgatt aaaaacggga | 3720 |
| tcccggtgaa acgtcgggaa actagctct accgtttccg tttccgttta ccgttttgta | 3780 |
| tatcccgttt ccgttccgtt ttcgtttttt acctcgggtt cgaaatcgat cgggataaaa | 3840 |
| ctaacaaaat cggttatacg ataacggtcg gtacgggatt ttcccatcct actttcatcc | 3900 |
| ctgcgtcggg tatcgagctc gaattaagct tgatatcgaa ttcctgcagg aaaaaaaaac | 3960 |
| aattagaatt aattttatat ttatacaatt tatggtgc | 3998 |

```
<210> SEQ ID NO 2
<211> LENGTH: 11
<212> TYPE: PRT
<213> ORGANISM: Artificial
<220> FEATURE:
<223> OTHER INFORMATION: Synthetic Nuclear Localization Signal

<400> SEQUENCE: 2

Met Gly Pro Pro Lys Lys Lys Arg Lys Val Glu
1               5                   10

<210> SEQ ID NO 3
<211> LENGTH: 27
<212> TYPE: DNA
<213> ORGANISM: Artificial
<220> FEATURE:
<223> OTHER INFORMATION: vector DNA
```

```
<400> SEQUENCE: 3
gaggatcccc gacggtcggg tatcgag                                              27

<210> SEQ ID NO 4
<211> LENGTH: 27
<212> TYPE: DNA
<213> ORGANISM: Artificial
<220> FEATURE:
<223> OTHER INFORMATION: vector DNA

<400> SEQUENCE: 4
gaggatcccc gactgtcggg tatcgag                                              27

<210> SEQ ID NO 5
<211> LENGTH: 26
<212> TYPE: DNA
<213> ORGANISM: Artificial
<220> FEATURE:
<223> OTHER INFORMATION: vector DNA

<400> SEQUENCE: 5
tggagctccc cgagtcgggt acccaa                                               26

<210> SEQ ID NO 6
<211> LENGTH: 28
<212> TYPE: DNA
<213> ORGANISM: Artificial
<220> FEATURE:
<223> OTHER INFORMATION: vector DNA

<400> SEQUENCE: 6
tggagctccc cgacggtcgg gtacccaa                                             28

<210> SEQ ID NO 7
<211> LENGTH: 2115
<212> TYPE: DNA
<213> ORGANISM: Zea mays
<220> FEATURE:
<221> NAME/KEY: CDS
<222> LOCATION: (1)..(2115)

<400> SEQUENCE: 7
```

| | | | | | | | | | | | | | | | | |
|---|---|---|---|---|---|---|---|---|---|---|---|---|---|---|---|---|
| atg | gct | att | gtt | cat | gaa | cca | caa | cca | caa | cca | caa | cca | gaa | | | 48 |
| Met | Ala | Ile | Val | His | Glu | Pro | Gln | Pro | Gln | Pro | Gln | Pro | Glu | | | |
| 1 | | | | 5 | | | | | 10 | | | | | 15 | | |
| cca | caa | cca | cag | cca | caa | cct | gaa | ccc | gaa | gaa | gaa | gca | cca | cag | aag | 96 |
| Pro | Gln | Pro | Gln | Pro | Gln | Pro | Glu | Pro | Glu | Glu | Glu | Ala | Pro | Gln | Lys | |
| | | 20 | | | | | 25 | | | | | 30 | | | | |
| agg | gca | aag | aag | tgc | aca | tcg | gat | gta | tgg | cag | cat | ttc | acc | aag | aag | 144 |
| Arg | Ala | Lys | Lys | Cys | Thr | Ser | Asp | Val | Trp | Gln | His | Phe | Thr | Lys | Lys | |
| | 35 | | | | | 40 | | | | | 45 | | | | | |
| gaa | att | gaa | gtg | gag | gtc | gat | gga | aag | aaa | tac | gtt | cag | gta | tgg | ggg | 192 |
| Glu | Ile | Glu | Val | Glu | Val | Asp | Gly | Lys | Lys | Tyr | Val | Gln | Val | Trp | Gly | |
| 50 | | | | | 55 | | | | | 60 | | | | | | |
| cat | tgc | aac | ttt | cct | aat | tgc | aag | gct | aag | tat | agg | gct | gag | ggt | cat | 240 |
| His | Cys | Asn | Phe | Pro | Asn | Cys | Lys | Ala | Lys | Tyr | Arg | Ala | Glu | Gly | His | |
| 65 | | | | 70 | | | | | 75 | | | | | 80 | | |
| cat | gga | aca | agc | gga | ttt | cga | aat | cac | ttg | aga | aca | tca | cat | agt | tta | 288 |
| His | Gly | Thr | Ser | Gly | Phe | Arg | Asn | His | Leu | Arg | Thr | Ser | His | Ser | Leu | |
| | | | | 85 | | | | | 90 | | | | | 95 | | |
| gtt | aaa | ggt | cag | ttg | tgt | cta | aaa | agt | gaa | aag | gat | cat | ggc | aaa | gac | 336 |
| Val | Lys | Gly | Gln | Leu | Cys | Leu | Lys | Ser | Glu | Lys | Asp | His | Gly | Lys | Asp | |
| | | | 100 | | | | | 105 | | | | | 110 | | | |

```
ata aat ctc att gag cct tat aag tac gat gaa gtg gtt agc cta aag      384
Ile Asn Leu Ile Glu Pro Tyr Lys Tyr Asp Glu Val Val Ser Leu Lys
    115                 120                 125 aag ctt cat ttg gca ata atc atg cat gaa tac cct ttc aat att gta      432
Lys Leu His Leu Ala Ile Ile Met His Glu Tyr Pro Phe Asn Ile Val
130                 135                 140 gaa cat gag tac ttt gtt gag ttt gtt aag tct ctg cgc cct cac ttt      480
Glu His Glu Tyr Phe Val Glu Phe Val Lys Ser Leu Arg Pro His Phe
145                 150                 155                 160 cca ata aag tcc cgt gtc act gct aga aaa tat atc atg gat ttg tat      528
Pro Ile Lys Ser Arg Val Thr Ala Arg Lys Tyr Ile Met Asp Leu Tyr
                165                 170                 175 ttg gaa gaa aaa gaa aag ttg tat gga aaa cta aaa gat gtt cag tct      576
Leu Glu Glu Lys Glu Lys Leu Tyr Gly Lys Leu Lys Asp Val Gln Ser
            180                 185                 190 cgc ttc agt aca act atg gat atg tgg aca tct tgt caa aat aag tca      624
Arg Phe Ser Thr Thr Met Asp Met Trp Thr Ser Cys Gln Asn Lys Ser
        195                 200                 205 tac atg tgt gtc acc atc cat tgg att gat gat gat tgg tgt ctc caa      672
Tyr Met Cys Val Thr Ile His Trp Ile Asp Asp Asp Trp Cys Leu Gln
    210                 215                 220 aaa aga att gtt ggc ttt ttt cat gtt gaa ggg cgc cac act ggc caa      720
Lys Arg Ile Val Gly Phe Phe His Val Glu Gly Arg His Thr Gly Gln
225                 230                 235                 240 agg tta tca caa acc ttc act gca atc atg gtt aag tgg aac att gag      768
Arg Leu Ser Gln Thr Phe Thr Ala Ile Met Val Lys Trp Asn Ile Glu
                245                 250                 255 aaa aaa ttg ttt gcc ttg tct ttg gat aat gct agt gca aat gaa gta      816
Lys Lys Leu Phe Ala Leu Ser Leu Asp Asn Ala Ser Ala Asn Glu Val
            260                 265                 270 gct gtg cac gat ata att gag gat ttg cag gac act gat tca aat cta      864
Ala Val His Asp Ile Ile Glu Asp Leu Gln Asp Thr Asp Ser Asn Leu
        275                 280                 285 gtt tgt gat ggt gct ttc ttt cat gtg agg tgt gct tgt cac ata ctg      912
Val Cys Asp Gly Ala Phe Phe His Val Arg Cys Ala Cys His Ile Leu
    290                 295                 300 aac ttg gtt gca aag gat ggc ttg gct gta att gca gga aca att gag      960
Asn Leu Val Ala Lys Asp Gly Leu Ala Val Ile Ala Gly Thr Ile Glu
305                 310                 315                 320 aaa atc aaa gcg att gtt ctt gct gta aaa tct tct cct ttg cag tgg     1008
Lys Ile Lys Ala Ile Val Leu Ala Val Lys Ser Ser Pro Leu Gln Trp
                325                 330                 335 gaa gaa cta atg aag tgt gct agt gaa tgt gac ttg gat aaa tct aaa     1056
Glu Glu Leu Met Lys Cys Ala Ser Glu Cys Asp Leu Asp Lys Ser Lys
            340                 345                 350 ggg atc tca tat gat gtc tca act aga tgg aat tca acc tat ttg atg     1104
Gly Ile Ser Tyr Asp Val Ser Thr Arg Trp Asn Ser Thr Tyr Leu Met
        355                 360                 365 ttg agg gat gcc tta tat tat aag cct gca cta ata agg ctt aaa aca     1152
Leu Arg Asp Ala Leu Tyr Tyr Lys Pro Ala Leu Ile Arg Leu Lys Thr
    370                 375                 380 agt gat cct cgc agg tac gat gca att tgt cct aaa gcc gag gag tgg     1200
Ser Asp Pro Arg Arg Tyr Asp Ala Ile Cys Pro Lys Ala Glu Glu Trp
385                 390                 395                 400 aag atg gca tta act ctt ttt aag tgt ttg aag aag ttt ttt gat ctc     1248
Lys Met Ala Leu Thr Leu Phe Lys Cys Leu Lys Lys Phe Phe Asp Leu
                405                 410                 415 act gaa ctc cta tct ggt act caa tat tcc act gca aat tta ttt tac     1296
Thr Glu Leu Leu Ser Gly Thr Gln Tyr Ser Thr Ala Asn Leu Phe Tyr
            420                 425                 430
```

```
aaa ggt ttc tgt gag ata aag gat ttg att gac caa tgg tgt gtt cat    1344
Lys Gly Phe Cys Glu Ile Lys Asp Leu Ile Asp Gln Trp Cys Val His
        435                 440                 445 gaa aaa ttt gtc att agg aga atg gcc gtt gca atg agt gaa aag ttt    1392
Glu Lys Phe Val Ile Arg Arg Met Ala Val Ala Met Ser Glu Lys Phe
450                 455                 460 gag aaa tat tgg aaa gtg tct aat att gca cta gct gta gca tgc ttc    1440
Glu Lys Tyr Trp Lys Val Ser Asn Ile Ala Leu Ala Val Ala Cys Phe
465                 470                 475                 480 ctt gac cct agg tac aag aaa ata ttg att gag ttc tat atg aaa aaa    1488
Leu Asp Pro Arg Tyr Lys Lys Ile Leu Ile Glu Phe Tyr Met Lys Lys
                485                 490                 495 ttt cat ggt gat tca tac aaa gtt cat gta gat gac ttt gtt agg gtc    1536
Phe His Gly Asp Ser Tyr Lys Val His Val Asp Asp Phe Val Arg Val
            500                 505                 510 att aga aaa ttg tat caa ttc tat tct agt tgt agt cct tca gct cca    1584
Ile Arg Lys Leu Tyr Gln Phe Tyr Ser Ser Cys Ser Pro Ser Ala Pro
        515                 520                 525 aag aca aag aca act act aat gat agt atg gat gat acc ttg atg gaa    1632
Lys Thr Lys Thr Thr Thr Asn Asp Ser Met Asp Asp Thr Leu Met Glu
530                 535                 540 aat gaa gat gat gaa ttt caa aac tat ttg cat gag ttg aag gat tat    1680
Asn Glu Asp Asp Glu Phe Gln Asn Tyr Leu His Glu Leu Lys Asp Tyr
545                 550                 555                 560 gat caa gta gag tca aat gaa ttg gat aaa tat atg tct gaa ccc ctt    1728
Asp Gln Val Glu Ser Asn Glu Leu Asp Lys Tyr Met Ser Glu Pro Leu
                565                 570                 575 ttg aag cat agt ggt cag ttt gat att tta tca tgg tgg agg gga agg    1776
Leu Lys His Ser Gly Gln Phe Asp Ile Leu Ser Trp Trp Arg Gly Arg
            580                 585                 590 gtt gca gaa tat cct att ctc acc caa att gca agg gat gtg cta gca    1824
Val Ala Glu Tyr Pro Ile Leu Thr Gln Ile Ala Arg Asp Val Leu Ala
        595                 600                 605 ata caa gtg tca act gtt gct tct gag tct gcg ttc agt gct ggt ggt    1872
Ile Gln Val Ser Thr Val Ala Ser Glu Ser Ala Phe Ser Ala Gly Gly
610                 615                 620 cgt gtt gtt gat cct tac cgc aat cgt ctt ggt tcg gag att gtt gaa    1920
Arg Val Val Asp Pro Tyr Arg Asn Arg Leu Gly Ser Glu Ile Val Glu
625                 630                 635                 640 gct ttg ata tgc aca aaa gat tgg gta gca gca tct aga aaa ggt gct    1968
Ala Leu Ile Cys Thr Lys Asp Trp Val Ala Ala Ser Arg Lys Gly Ala
                645                 650                 655 aca tat ttt cca aca atg att ggt gat ctc gag gtg cta gac tct gtt    2016
Thr Tyr Phe Pro Thr Met Ile Gly Asp Leu Glu Val Leu Asp Ser Val
            660                 665                 670 att gct gct gca aca aat cat gag aat cat atg gat gag gat gaa gac    2064
Ile Ala Ala Ala Thr Asn His Glu Asn His Met Asp Glu Asp Glu Asp
        675                 680                 685 gca ata gaa ttt tct aag aat aat gaa gat gta gca agt ggc tcc tct    2112
Ala Ile Glu Phe Ser Lys Asn Asn Glu Asp Val Ala Ser Gly Ser Ser
690                 695                 700 cca                                                                 2115
Pro
705

<210> SEQ ID NO 8
<211> LENGTH: 705
<212> TYPE: PRT
<213> ORGANISM: Zea mays

<400> SEQUENCE: 8
```

```
Met Ala Ile Val His Glu Pro Gln Pro Gln Pro Gln Pro Gln Pro Glu
1               5                   10                  15

Pro Gln Pro Gln Pro Gln Pro Glu Pro Glu Glu Ala Pro Gln Lys
            20                  25                  30

Arg Ala Lys Lys Cys Thr Ser Asp Val Trp Gln His Phe Thr Lys Lys
            35                  40                  45

Glu Ile Glu Val Glu Val Asp Gly Lys Lys Tyr Val Gln Val Trp Gly
        50                  55                  60

His Cys Asn Phe Pro Asn Cys Lys Ala Lys Tyr Arg Ala Glu Gly His
65                  70                  75                  80

His Gly Thr Ser Gly Phe Arg Asn His Leu Arg Thr Ser His Ser Leu
                85                  90                  95

Val Lys Gly Gln Leu Cys Leu Lys Ser Glu Lys Asp His Gly Lys Asp
            100                 105                 110

Ile Asn Leu Ile Glu Pro Tyr Lys Tyr Asp Glu Val Val Ser Leu Lys
            115                 120                 125

Lys Leu His Leu Ala Ile Ile Met His Glu Tyr Pro Phe Asn Ile Val
        130                 135                 140

Glu His Glu Tyr Phe Val Glu Phe Val Lys Ser Leu Arg Pro His Phe
145                 150                 155                 160

Pro Ile Lys Ser Arg Val Thr Ala Arg Lys Tyr Ile Met Asp Leu Tyr
                165                 170                 175

Leu Glu Glu Lys Glu Lys Leu Tyr Gly Lys Leu Lys Asp Val Gln Ser
            180                 185                 190

Arg Phe Ser Thr Thr Met Asp Met Trp Thr Ser Cys Gln Asn Lys Ser
        195                 200                 205

Tyr Met Cys Val Thr Ile His Trp Ile Asp Asp Trp Cys Leu Gln
210                 215                 220

Lys Arg Ile Val Gly Phe Phe His Val Glu Gly Arg His Thr Gly Gln
225                 230                 235                 240

Arg Leu Ser Gln Thr Phe Thr Ala Ile Met Val Lys Trp Asn Ile Glu
                245                 250                 255

Lys Lys Leu Phe Ala Leu Ser Leu Asp Asn Ala Ser Ala Asn Glu Val
            260                 265                 270

Ala Val His Asp Ile Ile Glu Asp Leu Gln Asp Thr Asp Ser Asn Leu
        275                 280                 285

Val Cys Asp Gly Ala Phe Phe His Val Arg Cys Ala Cys His Ile Leu
290                 295                 300

Asn Leu Val Ala Lys Asp Gly Leu Ala Val Ile Ala Gly Thr Ile Glu
305                 310                 315                 320

Lys Ile Lys Ala Ile Val Leu Ala Val Lys Ser Ser Pro Leu Gln Trp
                325                 330                 335

Glu Glu Leu Met Lys Cys Ala Ser Glu Cys Asp Leu Asp Lys Ser Lys
            340                 345                 350

Gly Ile Ser Tyr Asp Val Ser Thr Arg Trp Asn Ser Thr Tyr Leu Met
        355                 360                 365

Leu Arg Asp Ala Leu Tyr Tyr Lys Pro Ala Leu Ile Arg Leu Lys Thr
370                 375                 380

Ser Asp Pro Arg Arg Tyr Asp Ala Ile Cys Pro Lys Ala Glu Glu Trp
385                 390                 395                 400

Lys Met Ala Leu Thr Leu Phe Lys Cys Leu Lys Lys Phe Phe Asp Leu
                405                 410                 415

Thr Glu Leu Leu Ser Gly Thr Gln Tyr Ser Thr Ala Asn Leu Phe Tyr
            420                 425                 430
```

```
Lys Gly Phe Cys Glu Ile Lys Asp Leu Ile Asp Gln Trp Cys Val His
            435                 440                 445
Glu Lys Phe Val Ile Arg Arg Met Ala Val Ala Met Ser Glu Lys Phe
        450                 455                 460
Glu Lys Tyr Trp Lys Val Ser Asn Ile Ala Leu Ala Val Ala Cys Phe
465                 470                 475                 480
Leu Asp Pro Arg Tyr Lys Lys Ile Leu Ile Glu Phe Tyr Met Lys Lys
                485                 490                 495
Phe His Gly Asp Ser Tyr Lys Val His Val Asp Asp Phe Val Arg Val
            500                 505                 510
Ile Arg Lys Leu Tyr Gln Phe Tyr Ser Ser Cys Ser Pro Ser Ala Pro
        515                 520                 525
Lys Thr Lys Thr Thr Thr Asn Asp Ser Met Asp Asp Thr Leu Met Glu
530                 535                 540
Asn Glu Asp Asp Glu Phe Gln Asn Tyr Leu His Glu Leu Lys Asp Tyr
545                 550                 555                 560
Asp Gln Val Glu Ser Asn Glu Leu Asp Lys Tyr Met Ser Glu Pro Leu
                565                 570                 575
Leu Lys His Ser Gly Gln Phe Asp Ile Leu Ser Trp Trp Arg Gly Arg
            580                 585                 590
Val Ala Glu Tyr Pro Ile Leu Thr Gln Ile Ala Arg Asp Val Leu Ala
        595                 600                 605
Ile Gln Val Ser Thr Val Ala Ser Glu Ser Ala Phe Ser Ala Gly Gly
        610                 615                 620
Arg Val Val Asp Pro Tyr Arg Asn Arg Leu Gly Ser Glu Ile Val Glu
625                 630                 635                 640
Ala Leu Ile Cys Thr Lys Asp Trp Val Ala Ser Arg Lys Gly Ala
                645                 650                 655
Thr Tyr Phe Pro Thr Met Ile Gly Asp Leu Glu Val Leu Asp Ser Val
            660                 665                 670
Ile Ala Ala Ala Thr Asn His Glu Asn His Met Asp Glu Asp Glu Asp
        675                 680                 685
Ala Ile Glu Phe Ser Lys Asn Asn Glu Asp Val Ala Ser Gly Ser Ser
        690                 695                 700
Pro
705

<210> SEQ ID NO 9
<211> LENGTH: 11
<212> TYPE: PRT
<213> ORGANISM: Artificial
<220> FEATURE:
<223> OTHER INFORMATION: Modified Synthetic Nuclear Localization Signal

<400> SEQUENCE: 9

Met Gly Pro Pro Glu Lys Lys Arg Lys Val Glu
1               5                   10

<210> SEQ ID NO 10
<211> LENGTH: 2148
<212> TYPE: DNA
<213> ORGANISM: Artificial
<220> FEATURE:
<223> OTHER INFORMATION: NLS-TPase103-807 CDS

<400> SEQUENCE: 10
atgggtcctc caagaagaa gcgtaaggta gaaatggcta ttgttcatga accacaacca    60
```

|                                                                          |      |
|--------------------------------------------------------------------------|------|
| caaccacaac cacaaccaga accacaacca cagccacaac ctgaacccga agaagaagca        | 120  |
| ccacagaaga gggcaaagaa gtgcacatcg gatgtatggc agcatttcac caagaaggaa        | 180  |
| attgaagtgg aggtcgatgg aaagaaatac gttcaggtat gggggcattg caactttcct        | 240  |
| aattgcaagg ctaagtatag ggctgagggt catcatggaa caagcggatt tcgaaatcac        | 300  |
| ttgagaacat cacatagttt agttaaaggt cagttgtgtc taaaaagtga aaggatcat         | 360  |
| ggcaaagaca taaatctcat tgagcct tat aagtacgatg aagtggttag cctaaagaag       | 420  |
| cttcatttgg caataatcat gcatgaatac cctttcaata ttgtagaaca tgagtacttt        | 480  |
| gttgagtttg ttaagtctct gcgccctcac tttccaataa agtcccgtgt cactgctaga        | 540  |
| aaatatatca tggatttgta tttggaagaa aaagaaaagt tgtatggaaa actaaaagat        | 600  |
| gttcagtctc gcttcagtac aactatggat atgtggacat cttgtcaaaa taagtcatac        | 660  |
| atgtgtgtca ccatccattg gattgatgat gattggtgtc tccaaaaaag aattgttggc        | 720  |
| tttttttcatg ttgaagggcg ccacactggc caaaggttat cacaaacctt cactgcaatc      | 780  |
| atggttaagt ggaacattga gaaaaaattg tttgccttgt ctttggataa tgctagtgca        | 840  |
| aatgaagtag ctgtgcacga tataattgag gatttgcagg acactgattc aaatctagtt        | 900  |
| tgtgatggtg ctttctttca tgtgaggtgt gcttgtcaca tactgaactt ggttgcaaag        | 960  |
| gatggcttgg ctgtaattgc aggaacaatt gagaaaatca aagcgattgt tcttgctgta       | 1020 |
| aaatcttctc ctttgcagtg ggaagaacta atgaagtgtg ctagtgaatg tgacttggat       | 1080 |
| aaatctaaag ggatctcata tgatgtctca actagatgga attcaaccta tttgatgttg       | 1140 |
| agggatgcct tatattataa gcctgcacta ataaggctta aaacaagtga tcctcgcagg       | 1200 |
| tacgatgcaa tttgtcctaa agccgaggag tggaagatgg cattaactct ttttaagtgt       | 1260 |
| ttgaagaagt ttttgatct cactgaactc ctatctggta ctcaatattc cactgcaaat        | 1320 |
| ttatttaca aaggtttctg tgagataaag gatttgattg accaatggtg tgttcatgaa        | 1380 |
| aaatttgtca ttaggagaat ggccgttgca atgagtgaaa agtttgagaa atattggaaa       | 1440 |
| gtgtctaata ttgcactagc tgtagcatgc ttccttgacc ctaggtacaa gaaaatattg       | 1500 |
| attgagttct atatgaaaaa atttcatggt gattcataca aagttcatgt agatgacttt       | 1560 |
| gttagggtca ttagaaaatt gtatcaattc tattctagtt gtagtccttc agctccaaag       | 1620 |
| acaaagacaa ctactaatga tagtatggat gataccttga tggaaaatga agatgatgaa       | 1680 |
| tttcaaaact atttgcatga gttgaaggat tatgatcaag tagagtcaaa tgaattggat       | 1740 |
| aaatatatgt ctgaaccccct tttgaagcat agtggtcagt ttgatatttt atcatggtgg     | 1800 |
| agggaagggg ttgcagaata tcctattctc acccaaattg caagggatgt gctagcaata      | 1860 |
| caagtgtcaa ctgttgcttc tgagtctgcg ttcagtgctg gtggtcgtgt tgttgatcct      | 1920 |
| taccgcaatc gtcttggttc ggagattgtt gaagctttga tatgcacaaa agattgggta      | 1980 |
| gcagcatcta gaaaaggtgc tacatatttt ccaacaatga ttggtgatct cgaggtgcta      | 2040 |
| gactctgtta ttgctgctgc aacaaatcat gagaatcata tggatgagga tgaagacgca     | 2100 |
| atagaatttt ctaagaataa tgaagatgta gcaagtggct cctctcca                    | 2148 |

<210> SEQ ID NO 11
<211> LENGTH: 2687
<212> TYPE: DNA
<213> ORGANISM: Artificial
<220> FEATURE:
<223> OTHER INFORMATION: Modified Ac Transposase Construct
<220> FEATURE:
<221> NAME/KEY: misc_feature
<222> LOCATION: (1)..(2685)

<223> OTHER INFORMATION: n may be any nucleotide

<400> SEQUENCE: 11

| | | | | | |
|---|---|---|---|---|---|
| attaggcttg | tacatatgtn | gttagaacgc | ggctacaatt | aatacataac | cttatgtatc | 60 |
| atacacatac | gatttaggtg | acactataga | atacaagctt | gcttgttctt | tttgcagaag | 120 |
| ctcagaataa | acgctcaact | ttggcagatc | cgccaccatg | ggtcctccaa | agaagaagcg | 180 |
| taaggtagaa | atggctattg | ttcatgaacc | acaaccacaa | ccacaaccac | aaccagaacc | 240 |
| acaaccacag | ccacaacctg | aacccgaaga | agaagcacca | cagaagaggg | caagaagtg | 300 |
| cacatcggat | gtatggcagc | atttcaccaa | gaaggaaatt | gaagtggagg | tcgatggaaa | 360 |
| gaaatacgtt | caggtatggg | ggcattgcaa | ctttcctaat | tgcaaggcta | agtataggc | 420 |
| tgagggtcat | catggaacaa | gcggatttcg | aaatcacttg | agaacatcac | atagtttagt | 480 |
| taaaggtcag | ttgtgtctaa | aaagtgaaaa | ggatcatggc | aaagacataa | atctcattga | 540 |
| gccttataag | tacgatgaag | tggttagcct | aaagaagctt | catttggcaa | taatcatgca | 600 |
| tgaatacct | ttcaatattg | tagaacatga | gtactttgtt | gagtttgtta | agtctctgcg | 660 |
| ccctcacttt | ccaataaagt | cccgtgtcac | tgctagaaaa | tatatcatgg | atttgtattt | 720 |
| ggaagaaaaa | gaaaagttgt | atggaaaact | aaaagatgtt | cagtctcgct | tcagtacaac | 780 |
| tatggatatg | tggacatctt | gtcaaaataa | gtcatacatg | tgtgtcacca | tccattggat | 840 |
| tgatgatgat | tggtgtctcc | aaaaaagaat | tgttggcttt | tttcatgttg | aagggcgcca | 900 |
| cactggccaa | aggttatcac | aaaccttcac | tgcaatcatg | gttaagtgga | acattgagaa | 960 |
| aaaattgttt | gccttgtctt | tggataatgc | tagtgcaaat | gaagtagctg | tgcacgatat | 1020 |
| aattgaggat | ttgcaggaca | ctgattcaaa | tctagtttgt | gatggtgctt | tctttcatgt | 1080 |
| gaggtgtgct | tgtcacatac | tgaacttggt | tgcaaaggat | ggcttggctg | taattgcagg | 1140 |
| aacaattgag | aaaatcaaag | cgattgttct | tgctgtaaaa | tcttctcctt | tgcagtggga | 1200 |
| agaactaatg | aagtgtgcta | gtgaatgtga | cttggataaa | tctaaaggga | tctcatatga | 1260 |
| tgtctcaact | agatggaatt | caacctattt | gatgttgagg | gatgccttat | attataagcc | 1320 |
| tgcactaata | aggcttaaaa | caagtgatcc | tcgcaggtac | gatgcaattt | gtcctaaagc | 1380 |
| cgaggagtgg | aagatggcat | taactctttt | taagtgtttg | aagaagttt | ttgatctcac | 1440 |
| tgaactccta | tctggtactc | aatattccac | tgcaaattta | ttttacaaag | gtttctgtga | 1500 |
| gataaaggat | ttgattgacc | aatggtgtgt | tcatgaaaaa | tttgtcatta | ggagaatggc | 1560 |
| cgttgcaatg | agtgaaaagt | ttgagaaata | ttggaaagtg | tctaatattg | cactagctgt | 1620 |
| agcatgcttc | cttgacccta | ggtacaagaa | aatattgatt | gagttctata | tgaaaaaatt | 1680 |
| tcatggtgat | tcatacaaag | ttcatgtaga | tgactttgtt | agggtcatta | gaaaattgta | 1740 |
| tcaattctat | tctagttgta | gtccttcagc | tccaaagaca | aagacaacta | ctaatgatag | 1800 |
| tatgatgat | accttgatgg | aaaatgaaga | tgatgaattt | caaaactatt | tgcatgagtt | 1860 |
| gaaggattat | gatcaagtag | agtcaaatga | attggataaa | tatatgtctg | aacccctttt | 1920 |
| gaagcatagt | ggtcagtttg | atattttatc | atggtggagg | ggaagggttg | cagaatatcc | 1980 |
| tattctcacc | caaattgcaa | gggatgtgct | agcaatacaa | gtgtcaactg | ttgcttctga | 2040 |
| gtctgcgttc | agtgctggtg | gtcgtgttgt | tgatccttac | cgcaatcgtc | ttggttcgga | 2100 |
| gattgttgaa | gctttgatat | gcacaaaaga | ttgggtagca | gcatctagaa | aaggtgctac | 2160 |
| atattttcca | acaatgattg | gtgatctcga | ggtgctagac | tctgttattg | ctgctgcaac | 2220 |
| aaatcatgag | aatcatatgg | atgaggatga | agacgcaata | gaattttcta | agaataatga | 2280 |

| | |
|---|---|
| agatgtagca agtggctcct ctccatgagc aatgtgtctt atgtttgttg acagatgagc | 2340 |
| cttggttgta atagtttatg catgctaagt gctccagatg tgagcaagtg attatgaata | 2400 |
| tgtgttttaa actttatatt gtgtcatgtg tgctagtaga cttatatggc ttcttatgtt | 2460 |
| agccaagggg gccccgggat ctggttacca ctaaaccagc ctcaagaaca cccgaatgga | 2520 |
| gtctctaagc tacataatac caacttacac tttacaaaat gttgtccccc aagatgtagc | 2580 |
| cattcgtatc tgctcctaat aaaaagaaag tttcttcaca ttctaaaaaa aaaaaaaaaa | 2640 |
| aaaaaaaaaa aaaaaaaacc cccccccccc cccccctgca ggtcgac | 2687 |

<210> SEQ ID NO 12
<211> LENGTH: 11
<212> TYPE: DNA
<213> ORGANISM: Zea mays

<400> SEQUENCE: 12
tttcatccct g                                                            11

<210> SEQ ID NO 13
<211> LENGTH: 11
<212> TYPE: DNA
<213> ORGANISM: Zea mays

<400> SEQUENCE: 13
tttcatccct a                                                            11

<210> SEQ ID NO 14
<211> LENGTH: 47
<212> TYPE: DNA
<213> ORGANISM: Artificial
<220> FEATURE:
<223> OTHER INFORMATION: PCR Primer

<400> SEQUENCE: 14
ccaaagaaga agcgtaaggt agaaatggct attgttcatg aaccaca                     47

<210> SEQ ID NO 15
<211> LENGTH: 27
<212> TYPE: DNA
<213> ORGANISM: Artificial
<220> FEATURE:
<223> OTHER INFORMATION: PCR Primer

<400> SEQUENCE: 15
gtatcgataa gcttgatatc gaattcc                                           27

<210> SEQ ID NO 16
<211> LENGTH: 46
<212> TYPE: DNA
<213> ORGANISM: Artificial
<220> FEATURE:
<223> OTHER INFORMATION: PCR Primer

<400> SEQUENCE: 16
cgcggatccg ccaccatggg tcctccaaag aagaagcgta aggtag                      46

<210> SEQ ID NO 17
<211> LENGTH: 27
<212> TYPE: DNA
<213> ORGANISM: Artificial
<220> FEATURE:
<223> OTHER INFORMATION: PCR Primer

<400> SEQUENCE: 17

```
                                                                      27
gtatcgataa gcttgatatc gaattcc
```

<210> SEQ ID NO 18
<211> LENGTH: 23
<212> TYPE: DNA
<213> ORGANISM: Artificial
<220> FEATURE:
<223> OTHER INFORMATION: Primer

<400> SEQUENCE: 18

```
                                                                      23
gagaatttca cttgttgact aga
```

<210> SEQ ID NO 19
<211> LENGTH: 21
<212> TYPE: DNA
<213> ORGANISM: Artificial
<220> FEATURE:
<223> OTHER INFORMATION: Primer

<400> SEQUENCE: 19

```
                                                                      21
gcgcatgaac tccttgatga c
```

<210> SEQ ID NO 20
<211> LENGTH: 716
<212> TYPE: PRT
<213> ORGANISM: Artificial
<220> FEATURE:
<223> OTHER INFORMATION: NLS-TPase103-807

<400> SEQUENCE: 20

```
Met Gly Pro Pro Lys Lys Arg Lys Val Glu Met Ala Ile Val His
1               5                   10                  15

Glu Pro Gln Pro Gln Pro Gln Pro Gln Pro Glu Pro Gln Pro Gln Pro
            20                  25                  30

Gln Pro Glu Pro Glu Glu Ala Pro Gln Lys Arg Ala Lys Lys Cys
        35                  40                  45

Thr Ser Asp Val Trp Gln His Phe Thr Lys Lys Glu Ile Glu Val Glu
    50                  55                  60

Val Asp Gly Lys Lys Tyr Val Gln Val Trp Gly His Cys Asn Phe Pro
65                  70                  75                  80

Asn Cys Lys Ala Lys Tyr Arg Ala Glu Gly His His Gly Thr Ser Gly
                85                  90                  95

Phe Arg Asn His Leu Arg Thr Ser His Ser Leu Val Lys Gly Gln Leu
            100                 105                 110

Cys Leu Lys Ser Glu Lys Asp His Gly Lys Asp Ile Asn Leu Ile Glu
        115                 120                 125

Pro Tyr Lys Tyr Asp Glu Val Val Ser Leu Lys Lys Leu His Leu Ala
    130                 135                 140

Ile Ile Met His Glu Tyr Pro Phe Asn Ile Val Glu His Glu Tyr Phe
145                 150                 155                 160

Val Glu Phe Val Lys Ser Leu Arg Pro His Phe Pro Ile Lys Ser Arg
                165                 170                 175

Val Thr Ala Arg Lys Tyr Ile Met Asp Leu Tyr Leu Glu Glu Lys Glu
            180                 185                 190

Lys Leu Tyr Gly Lys Leu Lys Asp Val Gln Ser Arg Phe Ser Thr Thr
        195                 200                 205

Met Asp Met Trp Thr Ser Cys Gln Asn Lys Ser Tyr Met Cys Val Thr
    210                 215                 220

Ile His Trp Ile Asp Asp Asp Trp Cys Leu Gln Lys Arg Ile Val Gly
225                 230                 235                 240
```

-continued

```
Phe Phe His Val Glu Gly Arg His Thr Gly Gln Arg Leu Ser Gln Thr
            245                 250                 255

Phe Thr Ala Ile Met Val Lys Trp Asn Ile Glu Lys Lys Leu Phe Ala
            260                 265                 270

Leu Ser Leu Asp Asn Ala Ser Asn Glu Val Ala Val His Asp Ile
            275                 280                 285

Ile Glu Asp Leu Gln Asp Thr Asp Ser Asn Leu Val Cys Asp Gly Ala
        290                 295                 300

Phe Phe His Val Arg Cys Ala Cys His Ile Leu Asn Leu Val Ala Lys
305                 310                 315                 320

Asp Gly Leu Ala Val Ile Ala Gly Thr Ile Glu Lys Ile Lys Ala Ile
                    325                 330                 335

Val Leu Ala Val Lys Ser Ser Pro Leu Gln Trp Glu Glu Leu Met Lys
                340                 345                 350

Cys Ala Ser Glu Cys Asp Leu Asp Lys Ser Lys Gly Ile Ser Tyr Asp
                355                 360                 365

Val Ser Thr Arg Trp Asn Ser Thr Tyr Leu Met Leu Arg Asp Ala Leu
        370                 375                 380

Tyr Tyr Lys Pro Ala Leu Ile Arg Leu Lys Thr Ser Asp Pro Arg Arg
385                 390                 395                 400

Tyr Asp Ala Ile Cys Pro Lys Ala Glu Glu Trp Lys Met Ala Leu Thr
                    405                 410                 415

Leu Phe Lys Cys Leu Lys Lys Phe Phe Asp Leu Thr Glu Leu Leu Ser
                420                 425                 430

Gly Thr Gln Tyr Ser Thr Ala Asn Leu Phe Tyr Lys Gly Phe Cys Glu
                435                 440                 445

Ile Lys Asp Leu Ile Asp Gln Trp Cys Val His Glu Lys Phe Val Ile
        450                 455                 460

Arg Arg Met Ala Val Ala Met Ser Glu Lys Phe Glu Lys Tyr Trp Lys
465                 470                 475                 480

Val Ser Asn Ile Ala Leu Ala Val Ala Cys Phe Leu Asp Pro Arg Tyr
                    485                 490                 495

Lys Lys Ile Leu Ile Glu Phe Tyr Met Lys Lys Phe His Gly Asp Ser
                500                 505                 510

Tyr Lys Val His Val Asp Asp Phe Val Arg Val Ile Arg Lys Leu Tyr
            515                 520                 525

Gln Phe Tyr Ser Ser Cys Ser Pro Ser Ala Pro Lys Thr Lys Thr Thr
        530                 535                 540

Thr Asn Asp Ser Met Asp Asp Thr Leu Met Glu Asn Glu Asp Asp Glu
545                 550                 555                 560

Phe Gln Asn Tyr Leu His Glu Leu Lys Asp Tyr Asp Gln Val Glu Ser
                    565                 570                 575

Asn Glu Leu Asp Lys Tyr Met Ser Glu Pro Leu Leu Lys His Ser Gly
                580                 585                 590

Gln Phe Asp Ile Leu Ser Trp Trp Arg Gly Arg Val Ala Glu Tyr Pro
            595                 600                 605

Ile Leu Thr Gln Ile Ala Arg Asp Val Leu Ala Ile Gln Val Ser Thr
        610                 615                 620

Val Ala Ser Glu Ser Ala Phe Ser Ala Gly Arg Val Val Asp Pro
625                 630                 635                 640

Tyr Arg Asn Arg Leu Gly Ser Glu Ile Val Glu Ala Leu Ile Cys Thr
                    645                 650                 655

Lys Asp Trp Val Ala Ala Ser Arg Lys Gly Ala Thr Tyr Phe Pro Thr
```

-continued

```
                    660                 665                 670
Met Ile Gly Asp Leu Glu Val Leu Asp Ser Val Ile Ala Ala Ala Thr
                675                 680                 685

Asn His Glu Asn His Met Asp Glu Asp Glu Asp Ala Ile Glu Phe Ser
            690                 695                 700

Lys Asn Asn Glu Asp Val Ala Ser Gly Ser Ser Pro
705                 710                 715

<210> SEQ ID NO 21
<211> LENGTH: 24
<212> TYPE: DNA
<213> ORGANISM: Artificial
<220> FEATURE:
<223> OTHER INFORMATION: Primer

<400> SEQUENCE: 21
ccgtttaccg ttttgtatat cccg                                          24

<210> SEQ ID NO 22
<211> LENGTH: 22
<212> TYPE: DNA
<213> ORGANISM: Artificial
<220> FEATURE:
<223> OTHER INFORMATION: Primer

<400> SEQUENCE: 22
cgttccgttt tcgttttttta cc                                           22

<210> SEQ ID NO 23
<211> LENGTH: 20
<212> TYPE: DNA
<213> ORGANISM: Artificial
<220> FEATURE:
<223> OTHER INFORMATION: Primer

<400> SEQUENCE: 23
cggtcggtac gggatttttcc                                              20

<210> SEQ ID NO 24
<211> LENGTH: 24
<212> TYPE: DNA
<213> ORGANISM: Artificial
<220> FEATURE:
<223> OTHER INFORMATION: Primer

<400> SEQUENCE: 24
cgattaccgt atttatcccg ttcg                                          24

<210> SEQ ID NO 25
<211> LENGTH: 19
<212> TYPE: DNA
<213> ORGANISM: Artificial
<220> FEATURE:
<223> OTHER INFORMATION: Primer

<400> SEQUENCE: 25
ccggtatatc ccgttttcg                                                19

<210> SEQ ID NO 26
<211> LENGTH: 21
<212> TYPE: DNA
<213> ORGANISM: Artificial
<220> FEATURE:
<223> OTHER INFORMATION: Primer

<400> SEQUENCE: 26
```

```
gaaattgaaa acggtagagg t                                             21

<210> SEQ ID NO 27
<211> LENGTH: 16
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(16)
<223> OTHER INFORMATION: n may be any nucleotide

<400> SEQUENCE: 27
wgtgnagnan canaga                                                   16

<210> SEQ ID NO 28
<211> LENGTH: 16
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(16)
<223> OTHER INFORMATION: n may be any nucleotide

<400> SEQUENCE: 28
wcagntgwtn gtnctg                                                   16

<210> SEQ ID NO 29
<211> LENGTH: 16
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(16)
<223> OTHER INFORMATION: n may be any nucleotide

<400> SEQUENCE: 29
sttgntastn ctntgc                                                   16

<210> SEQ ID NO 30
<211> LENGTH: 16
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(16)
<223> OTHER INFORMATION: n may be any nucleotide

<400> SEQUENCE: 30
ncasgawagn cswcaa                                                   16

<210> SEQ ID NO 31
<211> LENGTH: 4
<212> TYPE: PRT
<213> ORGANISM: Zea mays

<400> SEQUENCE: 31

Met Ala Ile Val
 1

<210> SEQ ID NO 32
```

```
<211> LENGTH: 25
<212> TYPE: DNA
<213> ORGANISM: Artificial
<220> FEATURE:
<223> OTHER INFORMATION: Zea mays Ds flanked by zebrafish DNA

<400> SEQUENCE: 32
catgttgaac tgactaggga tgaaa                                        25

<210> SEQ ID NO 33
<211> LENGTH: 25
<212> TYPE: DNA
<213> ORGANISM: Artificial
<220> FEATURE:
<223> OTHER INFORMATION: Zea mays Ds flanked by zebrafish DNA

<400> SEQUENCE: 33
tttcatccct ggaactgacc gtcat                                        25

<210> SEQ ID NO 34
<211> LENGTH: 25
<212> TYPE: DNA
<213> ORGANISM: Artificial
<220> FEATURE:
<223> OTHER INFORMATION: Zea mays Ds flanked by zebrafish DNA

<400> SEQUENCE: 34
tatatgcttt tctttaggga tgaaa                                        25

<210> SEQ ID NO 35
<211> LENGTH: 25
<212> TYPE: DNA
<213> ORGANISM: Artificial
<220> FEATURE:
<223> OTHER INFORMATION: Zea mays Ds flanked by zebrafish DNA

<400> SEQUENCE: 35
tttcatccct gcttttcttc tgctg                                        25

<210> SEQ ID NO 36
<211> LENGTH: 2148
<212> TYPE: DNA
<213> ORGANISM: Artificial
<220> FEATURE:
<223> OTHER INFORMATION: NLS(K5E)-TPase103-807 CDS

<400> SEQUENCE: 36
atgggtcctc cagagaagaa gcgtaaggta gaaatggcta ttgttcatga accacaacca      60
caaccacaac cacaaccaga accacaacca cagccacaac ctgaacccga agaagaagca     120
ccacagaaga gggcaaagaa gtgcacatcg gatgtatggc agcatttcac caagaaggaa     180
attgaagtgg aggtcgatgg aaagaaatac gttcaggtat gggggcattg caactttcct     240
aattgcaagg ctaagtatag gctgagggt catcatggaa caagcggatt tcgaaatcac      300
ttgagaacat cacatagttt agttaaaggt cagttgtgtc taaaaagtga aaggatcat      360 ggcaaagaca taaatctcat tgagccttat aagtacgatg aagtggttag cctaaagaag     420
cttcatttgg caataatcat gcatgaatac cctttcaata ttgtagaaca tgagtacttt     480
gttgagtttg ttaagtctct gcgccctcac tttccaataa agtcccgtgt cactgctaga     540
aaatatatca tggatttgta tttggaagaa aaagaaaagt tgtatggaaa actaaaagat     600
gttcagtctc gcttcagtac aactatggat atgtggacat cttgtcaaaa taagtcatac     660
atgtgtgtca ccatccattg gattgatgat gattggtgtc tccaaaaaag aattgttggc     720
```

| | | |
|---|---|---|
| tttttttcatg ttgaagggcg ccacactggc caaaggttat cacaaacctt cactgcaatc | 780 | |
| atggttaagt ggaacattga gaaaaaattg tttgccttgt ctttggataa tgctagtgca | 840 | |
| aatgaagtag ctgtgcacga tataattgag gatttgcagg acactgattc aaatctagtt | 900 | |
| tgtgatggtg cttctcttt ca tgtgaggtgt gcttgtcaca tactgaactt ggttgcaaag | 960 | |
| gatggcttgg ctgtaattgc aggaacaatt gagaaaatca aagcgattgt tcttgctgta | 1020 | |
| aaatcttctc ctttgcagtg ggaagaacta atgaagtgtg ctagtgaatg tgacttggat | 1080 | |
| aaatctaaag ggatctcata tgatgtctca actagatgga attcaaccta tttgatgttg | 1140 | |
| agggatgcct tatattataa gcctgcacta ataaggctta aaacaagtga tcctcgcagg | 1200 | |
| tacgatgcaa tttgtcctaa agccgaggag tggaagatgg cattaactct ttttaagtgt | 1260 | |
| ttgaagaagt ttttgatct cactgaactc ctatctggta ctcaatattc cactgcaaat | 1320 | |
| ttatttaca aaggtttctg tgagataaag gatttgattg accaatggtg tgttcatgaa | 1380 | |
| aaatttgtca ttaggagaat ggccgttgca atgagtgaaa agtttgagaa atattggaaa | 1440 | |
| gtgtctaata ttgcactagc tgtagcatgc ttccttgacc ctaggtacaa gaaaatattg | 1500 | |
| attgagttct atatgaaaaa atttcatggt gattcataca aagttcatgt agatgacttt | 1560 | |
| gttagggtca ttagaaaatt gtatcaattc tattctagtt gtagtccttc agctccaaag | 1620 | |
| acaaagacaa ctactaatga tagtatggat gataccttga tggaaaatga agatgatgaa | 1680 | |
| tttcaaaact atttgcatga gttgaaggat tatgatcaag tagagtcaaa tgaattggat | 1740 | |
| aaatatatgt ctgaaccct tttgaagcat agtggtcagt ttgatatttt atcatggtgg | 1800 | |
| aggggaaggg ttgcagaata tcctattctc acccaaattg caagggatgt gctagcaata | 1860 | |
| caagtgtcaa ctgttgcttc tgagtctgcg ttcagtgctg gtggtcgtgt tgttgatcct | 1920 | |
| taccgcaatc gtcttggttc ggagattgtt gaagctttga tatgcacaaa agattgggta | 1980 | |
| gcagcatcta gaaaaggtgc tacatatttt ccaacaatga ttggtgatct cgaggtgcta | 2040 | |
| gactctgtta ttgctgctgc aacaaatcat gagaatcata tggatgagga tgaagacgca | 2100 | |
| atagaatttt ctaagaataa tgaagatgta gcaagtggct cctctcca | 2148 | |

<210> SEQ ID NO 37
<211> LENGTH: 2687
<212> TYPE: DNA
<213> ORGANISM: Artificial
<220> FEATURE:
<223> OTHER INFORMATION: Modified Ac Transposase Construct
<220> FEATURE:
<221> NAME/KEY: misc_feature
<222> LOCATION: (20)..(20)
<223> OTHER INFORMATION: n is a, c, g, or t

<400> SEQUENCE: 37

| | | |
|---|---|---|
| attaggcttg tacatatgtn gttagaacgc ggctacaatt aatacataac cttatgtatc | 60 | |
| atacacatac gatttaggtg acactataga ataagctt gcttgttctt tttgcagaag | 120 | |
| ctcagaataa acgctcaact tggcagatc cgccaccatg ggtcctccag agaagaagcg | 180 | |
| taaggtagaa atggctattg ttcatgaacc acaaccacaa ccacaaccac aaccagaacc | 240 | |
| acaaccacag ccacaaccctg aacccgaaga agaagcacca cagaagaggg caaagaagtg | 300 | |
| cacatcggat gtatggcagc atttcaccaa gaaggaaatt gaagtggagg tcgatggaaa | 360 | |
| gaaatacgtt caggtatggg ggcattgcaa cttttcctaat tgcaaggcta agtatagggc | 420 | |
| tgagggtcat catggaacaa gcggatttcg aaattcacttg agaacatcac atagtttagt | 480 | |
| taaaggtcag ttgtgtctaa aaagtgaaaa ggatcatggc aaagacataa atctcattga | 540 | |

```
gccttataag tacgatgaag tggttagcct aagaagctt catttggcaa taatcatgca    600
tgaatacccct ttcaatattg tagaacatga gtactttgtt gagtttgtta agtctctgcg   660
ccctcacttt ccaataaagt cccgtgtcac tgctagaaaa tatatcatgg atttgtattt   720
ggaagaaaaa gaaagttgt atggaaaact aaaagatgtt cagtctcgct tcagtacaac   780
tatggatatg tggacatctt gtcaaaataa gtcatacatg tgtgtcacca tccattggat   840
tgatgatgat tggtgtctcc aaaaaagaat tgttggcttt tttcatgttg aagggcgcca   900
cactggccaa aggttatcac aaaccttcac tgcaatcatg gttaagtgga acattgagaa   960
aaaattgttt gccttgtctt tggataatgc tagtgcaaat gaagtagctg tgcacgatat   1020
aattgaggat ttgcaggaca ctgattcaaa tctagtttgt gatggtgctt tctttcatgt   1080
gaggtgtgct tgtcacatac tgaacttggt tgcaaaggat ggcttggctg taattgcagg   1140
aacaattgag aaaatcaaag cgattgttct tgctgtaaaa tcttctcctt tgcagtggga   1200
agaactaatg aagtgtgcta gtgaatgtga cttggataaa tctaaaggga tctcatatga   1260
tgtctcaact agatggaatt caacctattt gatgttgagg gatgccttat attataagcc   1320
tgcactaata aggcttaaaa caagtgatcc tcgcaggtac gatgcaattt gtcctaaagc   1380
cgaggagtgg aagatggcat aactcttt taagtgtttg aagaagtttt ttgatctcac   1440
tgaactccta tctggtactc aatattccac tgcaaattta ttttacaaag gtttctgtga   1500
gataaaggat ttgattgacc aatggtgtgt tcatgaaaaa tttgtcatta ggagaatggc   1560
cgttgcaatg agtgaaaagt ttgagaaata ttggaaagtg tctaatattg cactagctgt   1620
agcatgcttc cttgacccta ggtacaagaa aatattgatt gagttctata tgaaaaaatt   1680
tcatggtgat tcatacaaag ttcatgtaga tgactttgtt agggtcatta gaaaattgta   1740
tcaattctat tctagttgta gtccttcagc tccaaagaca aagacaacta ctaatgatag   1800
tatggatgat accttgatgg aaaatgaaga tgatgaattt caaaactatt tgcatgagtt   1860
gaaggattat gatcaagtag agtcaaatga attggataaa tatatgtctg aaccccttt   1920
gaagcatagt ggtcagtttg atatttttatc atggtggagg ggaaggggttg cagaatatcc   1980
tattctcacc caaattgcaa gggatgtgct agcaatacaa gtgtcaactg ttgcttctga   2040
gtctgcgttc agtgctggtg gtcgtgttgt tgatccttac cgcaatcgtc ttggttcgga   2100
gattgttgaa gctttgatat gcacaaaaga ttgggtagca gcatctagaa aaggtgctac   2160
atatttttcca acaatgattg gtgatctcga ggtgctagac tctgttattg ctgctgcaac   2220
aaatcatgag aatcatatgg atgaggatga agacgcaata gaattttcta gaataatga   2280
agatgtagca agtggctcct ctccatgagc aatgtgtctt atgtttgttg acagatgagc   2340
cttggttgta atagtttatg catgctaagt gctccagatg tgagcaagtg attatgaata   2400
tgtgttttaa actttatatt gtgtcatgtg tgctagtaga cttatatggc ttcttatgtt   2460
agccaagggg gccccgggat ctggttacca ctaaaccagc ctcaagaaca cccgaatgga   2520
gtctctaagc tacataatac caacttacac tttacaaaat gttgtccccc aagatgtagc   2580
cattcgtatc tgctccctaat aaaagaaag tttcttcaca ttctaaaaaa aaaaaaaaaa   2640
aaaaaaaaaa aaaaaaaacc ccccccccc ccccctgca ggtcgac                  2687
```

<210> SEQ ID NO 38
<211> LENGTH: 50
<212> TYPE: DNA
<213> ORGANISM: Artificial
<220> FEATURE:
<223> OTHER INFORMATION: Primer -continued

```
<400> SEQUENCE: 38
ctcaactttg gcagatccgc caccatggct attgttcatg aaccacaacc        50

<210> SEQ ID NO 39
<211> LENGTH: 50
<212> TYPE: DNA
<213> ORGANISM: Artificial
<220> FEATURE:
<223> OTHER INFORMATION: Primer

<400> SEQUENCE: 39
ggttgtggtt catgaacaat agccatggtg gcggatctgc caaagttgag        50

<210> SEQ ID NO 40
<211> LENGTH: 31
<212> TYPE: DNA
<213> ORGANISM: Artificial
<220> FEATURE:
<223> OTHER INFORMATION: PCR Primer

<400> SEQUENCE: 40
agagggatcc agctcagaat aaacgctcaa c                            31

<210> SEQ ID NO 41
<211> LENGTH: 32
<212> TYPE: DNA
<213> ORGANISM: Artificial
<220> FEATURE:
<223> OTHER INFORMATION: PCR Primer

<400> SEQUENCE: 41
agagaccggt cctggagagg agccacttgc ta                           32

<210> SEQ ID NO 42
<211> LENGTH: 42
<212> TYPE: DNA
<213> ORGANISM: Artificial
<220> FEATURE:
<223> OTHER INFORMATION: Primer

<400> SEQUENCE: 42
agaagaagcg taaggtagaa atggtgagca agggcgagga gc                42

<210> SEQ ID NO 43
<211> LENGTH: 42
<212> TYPE: DNA
<213> ORGANISM: Artificial
<220> FEATURE:
<223> OTHER INFORMATION: Primer

<400> SEQUENCE: 43
gctcctcgcc cttgctcacc atttctacct tacgcttctt ct                42

<210> SEQ ID NO 44
<211> LENGTH: 716
<212> TYPE: PRT
<213> ORGANISM: Artificial
<220> FEATURE:
<223> OTHER INFORMATION: NLS(K5E)-TPase103-807

<400> SEQUENCE: 44

Met Gly Pro Pro Glu Lys Lys Arg Lys Val Glu Met Ala Ile Val His
 1               5                  10                  15

Glu Pro Gln Pro Gln Pro Gln Pro Gln Pro Glu Pro Gln Pro Gln Pro
                20                  25                  30
```

```
Gln Pro Glu Pro Glu Glu Ala Pro Gln Lys Arg Ala Lys Lys Cys
    35                  40                  45

Thr Ser Asp Val Trp Gln His Phe Thr Lys Lys Glu Ile Glu Val Glu
50                  55                  60

Val Asp Gly Lys Lys Tyr Val Gln Val Trp Gly His Cys Asn Phe Pro
65                  70                  75                  80

Asn Cys Lys Ala Lys Tyr Arg Ala Glu Gly His His Gly Thr Ser Gly
                85                  90                  95

Phe Arg Asn His Leu Arg Thr Ser His Ser Leu Val Lys Gly Gln Leu
            100                 105                 110

Cys Leu Lys Ser Glu Lys Asp His Gly Lys Asp Ile Asn Leu Ile Glu
        115                 120                 125

Pro Tyr Lys Tyr Asp Glu Val Val Ser Leu Lys Lys Leu His Leu Ala
    130                 135                 140

Ile Ile Met His Glu Tyr Pro Phe Asn Ile Val Glu His Glu Tyr Phe
145                 150                 155                 160

Val Glu Phe Val Lys Ser Leu Arg Pro His Phe Pro Ile Lys Ser Arg
                165                 170                 175

Val Thr Ala Arg Lys Tyr Ile Met Asp Leu Tyr Leu Glu Glu Lys Glu
            180                 185                 190

Lys Leu Tyr Gly Lys Leu Lys Asp Val Gln Ser Arg Phe Ser Thr Thr
        195                 200                 205

Met Asp Met Trp Thr Ser Cys Gln Asn Lys Ser Tyr Met Cys Val Thr
    210                 215                 220

Ile His Trp Ile Asp Asp Asp Trp Cys Leu Gln Lys Arg Ile Val Gly
225                 230                 235                 240

Phe Phe His Val Glu Gly Arg His Thr Gly Gln Arg Leu Ser Gln Thr
                245                 250                 255

Phe Thr Ala Ile Met Val Lys Trp Asn Ile Glu Lys Lys Leu Phe Ala
            260                 265                 270

Leu Ser Leu Asp Asn Ala Ser Ala Asn Glu Val Ala Val His Asp Ile
        275                 280                 285

Ile Glu Asp Leu Gln Asp Thr Asp Ser Asn Leu Val Cys Asp Gly Ala
    290                 295                 300

Phe Phe His Val Arg Cys Ala Cys His Ile Leu Asn Leu Val Ala Lys
305                 310                 315                 320

Asp Gly Leu Ala Val Ile Ala Gly Thr Ile Glu Lys Ile Lys Ala Ile
                325                 330                 335

Val Leu Ala Val Lys Ser Ser Pro Leu Gln Trp Glu Glu Leu Met Lys
            340                 345                 350

Cys Ala Ser Glu Cys Asp Leu Asp Lys Ser Lys Gly Ile Ser Tyr Asp
        355                 360                 365

Val Ser Thr Arg Trp Asn Ser Thr Tyr Leu Met Leu Arg Asp Ala Leu
    370                 375                 380

Tyr Tyr Lys Pro Ala Leu Ile Arg Leu Lys Thr Ser Asp Pro Arg Arg
385                 390                 395                 400

Tyr Asp Ala Ile Cys Pro Lys Ala Glu Glu Trp Lys Met Ala Leu Thr
                405                 410                 415

Leu Phe Lys Cys Leu Lys Lys Phe Phe Asp Leu Thr Glu Leu Leu Ser
            420                 425                 430

Gly Thr Gln Tyr Ser Thr Ala Asn Leu Phe Tyr Lys Gly Phe Cys Glu
        435                 440                 445

Ile Lys Asp Leu Ile Asp Gln Trp Cys Val His Glu Lys Phe Val Ile
    450                 455                 460
```

```
Arg Arg Met Ala Val Ala Met Ser Glu Lys Phe Glu Lys Tyr Trp Lys
465                 470                 475                 480

Val Ser Asn Ile Ala Leu Ala Val Ala Cys Phe Leu Asp Pro Arg Tyr
                485                 490                 495

Lys Lys Ile Leu Ile Glu Phe Tyr Met Lys Lys Phe His Gly Asp Ser
            500                 505                 510

Tyr Lys Val His Val Asp Asp Phe Val Arg Val Ile Arg Lys Leu Tyr
        515                 520                 525

Gln Phe Tyr Ser Ser Cys Ser Pro Ser Ala Pro Lys Thr Lys Thr Thr
    530                 535                 540

Thr Asn Asp Ser Met Asp Asp Thr Leu Met Glu Asn Glu Asp Asp Glu
545                 550                 555                 560

Phe Gln Asn Tyr Leu His Glu Leu Lys Asp Tyr Asp Gln Val Glu Ser
                565                 570                 575

Asn Glu Leu Asp Lys Tyr Met Ser Glu Pro Leu Leu Lys His Ser Gly
            580                 585                 590

Gln Phe Asp Ile Leu Ser Trp Trp Arg Gly Arg Val Ala Glu Tyr Pro
        595                 600                 605

Ile Leu Thr Gln Ile Ala Arg Asp Val Leu Ala Ile Gln Val Ser Thr
    610                 615                 620

Val Ala Ser Glu Ser Ala Phe Ser Ala Gly Gly Arg Val Val Asp Pro
625                 630                 635                 640

Tyr Arg Asn Arg Leu Gly Ser Glu Ile Val Glu Ala Leu Ile Cys Thr
                645                 650                 655

Lys Asp Trp Val Ala Ala Ser Arg Lys Gly Ala Thr Tyr Phe Pro Thr
            660                 665                 670

Met Ile Gly Asp Leu Glu Val Leu Asp Ser Val Ile Ala Ala Ala Thr
        675                 680                 685

Asn His Glu Asn His Met Asp Glu Asp Glu Asp Ala Ile Glu Phe Ser
    690                 695                 700

Lys Asn Asn Glu Asp Val Ala Ser Gly Ser Ser Pro
705                 710                 715

<210> SEQ ID NO 45
<211> LENGTH: 292
<212> TYPE: DNA
<213> ORGANISM: Zea mays

<400> SEQUENCE: 45
cagggatgaa agtaggatgg gaaaatcccg taccgaccgt tatcgtataa ccgattttgt     60
tagttttatc ccgatcgatt tcgaacccga ggtaaaaaac gaaaacggaa cggaaacggg    120
atatacaaaa cggtaaacgg aaacggaaac ggtagagcta gtttcccgac cgtttcaccg    180
ggatcccgtt tttaatcggg atgatcccgt ttcgttaccg tatttttctaa ttcgggatga   240 ctgcaacaga tccctcgagc gcttaagttt aaacgcgtta acaattggcc at            292

<210> SEQ ID NO 46
<211> LENGTH: 1395
<212> TYPE: DNA
<213> ORGANISM: Artificial
<220> FEATURE:
<223> OTHER INFORMATION: pEGFP-N3 fragment

<400> SEQUENCE: 46
aatagtaatc aattacgggg tcattagttc atagcccata tatggagttc cgcgttacat     60
aacttacggt aaatggcccg cctggctgac cgcccaacga ccccgcccca ttgacgtcaa    120
```

```
taatgacgta tgttcccata gtaacgccaa tagggacttt ccattgacgt caatgggtgg      180
agtatttacg gtaaactgcc cacttggcag tacatcaagt gtatcatatg ccaagtacgc      240
cccctattga cgtcaatgac ggtaaatggc ccgcctggca ttatgcccag tacatgacct      300
tatgggactt tcctacttgg cagtacatct acgtattagt catcgctatt accatggtga      360
tgcggttttg gcagtacatc aatgggcgtg gatagcggtt tgactcacgg ggatttccaa      420
gtctccaccc cattgacgtc aatgggagtt tgttttggca ccaaaatcaa cgggactttc      480
caaaatgtcg taacaactcc gccccattga cgcaaatggg cggtaggcgt gtacggtggg      540
aggtctatat aagcagagct ggtttagtga accgtcagat ccgctagcgc taccggactc      600
agatctcgag ctcaagcttc gaattctgca gtcgacggta ccgcgggccc gggatccatc      660
gccaccatgg tgagcaaggg cgaggagctg ttcaccgggg tggtgcccat cctggtcgag      720
ctggacggcg acgtaaacgg ccacaagttc agcgtgtccg gcgagggcga gggcgatgcc      780
acctacggca agctgaccct gaagttcatc tgcaccaccg gcaagctgcc cgtgccctgg      840
cccaccctcg tgaccaccct gacctacggc gtgcagtgct tcagccgcta ccccgaccac      900
atgaagcagc acgacttctt caagtccgcc atgcccgaag gctacgtcca ggagcgcacc      960
atcttcttca aggacgacgg caactacaag acccgcgccg aggtgaagtt cgagggcgac     1020
accctggtga accgcatcga gctgaagggc atcgacttca aggaggacgg caacatcctg     1080
gggcacaagc tggagtacaa ctacaacagc cacaacgtct atatcatggc cgacaagcag     1140
aagaacggca tcaaggtgaa cttcaagatc cgccacaaca tcgaggacgg cagcgtgcag     1200
ctcgccgacc actaccagca gaacaccccc atcggcgacg gccccgtgct gctgcccgac     1260
aaccactacc tgagcaccca gtccgccctg agcaaagacc ccaacgagaa gcgcgatcac     1320
atggtcctgc tggagttcgt gaccgccgcc gggatcactc tcggcatgga cgagctgtac     1380
aagtaaagcg gccgc                                                    1395

<210> SEQ ID NO 47
<211> LENGTH: 1716
<212> TYPE: DNA
<213> ORGANISM: Artificial
<220> FEATURE:
<223> OTHER INFORMATION: pUBBSD1 plasmid fragment

<400> SEQUENCE: 47
gatatcgcta gctcgagatc gggagatctg gcctccgcgc cgggttttgg cgccccccgc       60
gggcgccccc tcctcacggc gagcgctgcc acgtcagacg aagggcgcac gagcgtcctg      120
atccttccgc ccggacgctc aggacagcgg cccgctgctc ataagactcg gccttagaac      180
cccagtatca gcagaaggac attttaggac gggacttggg tgactctagg gcactggttt      240
tctttccaga gagcggaaca ggcgaggaaa agtagtccct tctcggcgat tctgcggagg      300
gatctccgtg gggcggtgaa cgccgatgat tatataagga cgcgccgggt gtggcacagc      360
tagttccgtc gcagccggga tttgggtcgc ggttcttgtt tgtggatcgc tgtgatcgtc      420
acttggtgag tagcgggctg ctgggctggc cggggctttc gtggccgccg gccgctcgg      480 tgggacggaa gcgtgtggag agaccgccaa gggctgtagt ctgggtccgc gagcaaggtt      540
gccctgaact gggggttggg gggagcgcag caaaatggcg gctgttcccg agtcttgaat      600
ggaagacgct tgtgaggcgg gctgtgaggt cgttgaaaca aggtgggggg catggtgggc      660
ggcaagaacc caaggtcttg aggccttcgc taatgcggga aagctcttat tcgggtgaga      720
tgggctgggg caccatctgg ggaccctgac gtgaagtttg tcactgactg gagaactcgg      780
```

```
tttgtcgtct gttgcggggg cggcagttat ggcggtgccg ttgggcagtg cacccgtacc    840
tttgggagcg cgcgccctcg tcgtgtcgtg acgtcacccg ttctgttggc ttataatgca    900
gggtggggcc acctgccggt aggtgtgcgg taggctttc tccgtcgcag acgcagggt    960 tcgggcctag ggtaggctct cctgaatcga caggcgccgg acctctggtg aggggaggga   1020
taagtgaggc gtcagtttct ttggtcggtt ttatgtacct atcttcttaa gtagctgaag   1080
ctccggtttt gaactatgcg ctcggggttg gcgagtgtgt tttgtgaagt ttttaggca   1140 ccttttgaaa tgtaatcatt tgggtcaata tgtaatttc agtgttagac tagtaaattg    1200
tccgctaaat tctggccgtt tttggctttt ttgttagacc ggaccgtgtt gacaattaat   1260
catcggcata gtatatcggc atagtataat cgacaaggt gaggaactaa accatggcca    1320
agcctttgtc tcaagaagaa tccaccctca ttgaaagagc aacggctaca atcaacagca   1380
tccccatctc tgaagactac agcgtcgcca gcgcagctct ctctagcgac ggccgcatct   1440
tcactggtgt caatgtatat cattttactg ggggaccttg tgcagaactc gtggtgctgg   1500
gcactgctgc tgctgcggca gctggcaacc tgacttgtat cgtcgcgatc ggaaatgaga   1560
acaggggcat cttgagcccc tgcggacggt gccgacaggt gcttctcgat ctgcatcctg   1620
ggatcaaagc catagtgaag gacagtgatg gacagccgac ggcagttggg attcgtgaat   1680
tgctgccctc tggttatgtg tgggagggct aagcac                              1716

<210> SEQ ID NO 48
<211> LENGTH: 1062
<212> TYPE: DNA
<213> ORGANISM: Artificial
<220> FEATURE:
<223> OTHER INFORMATION: Cloning vector fragment with plasmid
      replication origin

<400> SEQUENCE: 48
ttcgtggccg aggagcagga ctgacactcg acctcgaaac ttgtttattg cagcttataa     60
tggttacaaa taaagcaata gcatcacaaa tttcacaaat aaagcatttt tttcactgca    120
ttctagttgt ggtttgtcca aactcatcaa tgtatcttat catgtctgaa ttcccgggga    180
tcctctagac tgtcagacca agtttactca tatatacttt agattgattt aaaacttcat    240
ttttaattta aaaggatcta ggtgaagatc cttttgata atctcatgac caaaatccct    300
taacgtgagt tttcgttcca ctgagcgtca gaccccgtag aaaagatcaa aggatcttct    360
tgagatcctt ttttctgcg cgtaatctgc tgcttgcaaa caaaaaaacc accgctacca    420
gcggtggttt gtttgccgga tcaagagcta ccaactcttt ttccgaaggt aactggcttc    480
agcagagcgc agataccaaa tactgttctt ctagtgtagc cgtagttagg ccaccacttc    540
aagaactctg tagcaccgcc tacatacctc gctctgctaa tcctgttacc agtggctgct    600
gccagtggcg ataagtcgtg tcttaccggg ttggactcaa gacgatagtt accggataag    660
gcgcagcggt cgggctgaac ggggggttcg tgcacacagc ccagcttgga gcgaacgacc    720
tacaccgaac tgagatacct acagcgtgag ctatgagaaa gcgccacgct tcccgaaggg    780
agaaaggcgg acaggtatcc ggtaagcggc agggtcggaa caggagagcg cacgagggag    840
cttccagggg gaaacgcctg gtatctttat agtcctgtcg ggtttcgcca cctctgactt    900
gagcgtcgat ttttgtgatg ctcgtcaggg gggcggagcc tatggaaaaa cgccagcaac    960
gcggcctttt tacggttccc ggcctttgc tggccttttg ctcacatgct gggcccagca   1020
ggccagatct gagctcgcgg ccgcgatatc gctagctcga gg                       1062
```

<210> SEQ ID NO 49
<211> LENGTH: 370
<212> TYPE: DNA
<213> ORGANISM: Zea mays

<400> SEQUENCE: 49

```
gacttatatg gcttcttatg ttagccaaga gcccaagact tatcacttat gtgctacatt      60
aaactatgtg tgctccagat ttatatggat tttatctatg tttaattaag acttgtgttt     120
acaatttttt atatttgttt ttaagttttg aatatatgtt ttcatgtgtg attttaccga     180
acaaaaatac cggttcccgt ccgatttcga ctttaacccg accggatcgt atcggttttc     240
gattaccgta tttatcccgt tcgttttcgt taccggtata tcccgttttc gtttccgtcc     300
cgcaagttaa atatgaaaat gaaacggta gaggtatttt accgaccgtt accgaccgtt     360
ttcatcccta                                                           370
```

<210> SEQ ID NO 50
<211> LENGTH: 1660
<212> TYPE: DNA
<213> ORGANISM: Artificial
<220> FEATURE:
<223> OTHER INFORMATION: Cloning vector fragment witih Amp resistance gene

<400> SEQUENCE: 50

```
tgcattctga cagttaccaa tgcttaatca gtgaggcacc tatctcagcg atctgtctat      60
ttcgttcatc catagttgcc tgactccccg tcgtgtagat aactacgata cgggagggct     120
taccatctgg ccccagtgct gcaatgatac cgcgagaccc acgctcaccg gctccagatt     180
tatcagcaat aaaccagcca gccggaaggg ccgagcgcag aagtggtcct gcaactttat     240
ccgcctccat ccagtctatt aattgttgcc gggaagctag agtaagtagt tcgccagtta     300
atagtttgcg caacgttgtt gccattgcta caggcatcgt ggtgtcacgc tcgtcgtttg     360
gtatggcttc attcagctcc ggttcccaac gatcaaggcg agttacatga tcccccatgt     420
tgtgcaaaaa agcggttagc tccttcggtc ctccgatcgt tgtcagaagt aagttggccg     480
cagtgttatc actcatggtt atggcagcac tgcataattc tcttactgtc atgccatccg     540
taagatgctt ttctgtgact ggtgagtact caaccaagtc attctgagaa tagtgtatgc     600
ggcgaccgag ttgctcttgc ccggcgtcaa tacgggataa taccgcgcca catagcagaa     660
ctttaaaagt gctcatcatt ggaaaacgtt cttcggggcg aaaactctca aggatcttac     720
cgctgttgag atccagttcg atgtaaccca ctcgtgcacc caactgatct tcagcatctt     780
ttactttcac cagcgtttct gggtgagcaa aaacaggaag gcaaaatgcc gcaaaaaagg     840
gaataagggc gacacggaaa tgttgaatac tcatactctt cctttttcaa tataattgaa     900
gcatttatca gggttattgt ctcatgagcg gatacatatt tgaatgtatt tagaaaaata     960
aacaaatagg ggttccgcgc acatttcccc gaaaagtgcc acctaaattg taagcgttaa    1020
tattttgtta aaattcgcgt taaatttttg ttaaatcagc tcatttttta accaataggc    1080
cgaaatcggc aaaatccctt ataaatcaaa agaatagacc gagatagggt tgagtgttgt    1140
tccagtttgg aacaagagtc cactattaaa gaacgtggac tccaacgtca aagggcgaaa    1200
aaccgtctat cagggcgatg gcccactacg tgaaccatca ccctaatcaa gttttttggg    1260
gtcgaggtgc cgtaaagcac taaatcggaa ccctaaaggg agcccccgat ttagagcttg    1320
acggggaaag ccggcgaacg tggcgagaaa ggaagggaag aaagcgaaag gagcgggcgc    1380
tagggcgctg gcaagtgtag cggtcacgct gcgcgtaacc accacacccg ccgcgcttaa    1440
```

```
tgcgccgcta cagggcgcgt cccattcgcc attcaggctg cgcaactgtt gggaagggcg    1500
atcggtgcgg gcctcttcgc tattacgcca gctggcgaaa gggggatgtg ctgcaaggcg    1560
attaagttgg gtaacgccag ggttttccca gtcacgacgt tgtaaaacga cggccagtga    1620
attgatacga ctcactatag ggcgaattgg gtacccgacg                          1660

<210> SEQ ID NO 51
<211> LENGTH: 33
<212> TYPE: DNA
<213> ORGANISM: Artificial
<220> FEATURE:
<223> OTHER INFORMATION: PCR Primer

<400> SEQUENCE: 51
gcgcggatcc atacgattta ggtgacacta tag                                  33

<210> SEQ ID NO 52
<211> LENGTH: 34
<212> TYPE: DNA
<213> ORGANISM: Artificial
<220> FEATURE:
<223> OTHER INFORMATION: PCR Primer

<400> SEQUENCE: 52
cgatcgatgc ggccgccttg gctaacataa gaag                                 34

<210> SEQ ID NO 53
<211> LENGTH: 665
<212> TYPE: DNA
<213> ORGANISM: Artificial
<220> FEATURE:
<223> OTHER INFORMATION: pEGFP-N1 plasmid fragment

<400> SEQUENCE: 53
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatcc gctagcgcta    600
ccggactcag atctcgagct caagcttcga attctgcagt cgacggtacc gcgggcccgg    660
gatcc                                                                665

<210> SEQ ID NO 54
<211> LENGTH: 2401
<212> TYPE: DNA
<213> ORGANISM: Artificial
<220> FEATURE:
<223> OTHER INFORMATION: Amplified fragment with NLS(K5E)-TPase ORF

<400> SEQUENCE: 54
atacgattta ggtgacacta tagaatacaa gcttgcttgt tctttttgca gaagctcaga     60
ataaacgctc aactttggca gatccgccac catgggtcct ccagagaaga agcgtaaggt    120
```

```
agaaatggct attgttcatg aaccacaacc acaaccacaa ccacaaccag aaccacaacc    180
acagccacaa cctgaacccg aagaagaagc accacagaag agggcaaaga agtgcacatc    240
ggatgtatgg cagcatttca ccaagaagga aattgaagtg gaggtcgatg gaaagaaata    300
cgttcaggta tgggggcatt gcaactttcc taattgcaag gctaagtata gggctgaggg    360
tcatcatgga acaagcggat ttcgaaatca cttgagaaca tcacatagtt tagttaaagg    420
tcagttgtgt ctaaaaagtg aaaaggatca tggcaaagac ataaatctca ttgagcctta    480
taagtacgat gaagtggtta gcctaaagaa gcttcatttg gcaataatca tgcatgaata    540 cccttttcaat attgtagaac atgagtactt tgttgagttt gttaagtctc tgcgccctca    600 cttttccaata aagtcccgtg tcactgctag aaaatatatc atggatttgt atttggaaga    660
aaaagaaaag ttgtatggaa aactaaaaga tgttcagtct cgcttcagta caactatgga    720
tatgtggaca tcttgtcaaa ataagtcata catgtgtgtc accatccatt ggattgatga    780
tgattggtgt ctccaaaaaa gaattgttgg cttttttcat gttgaagggc gccacactgg    840
ccaaaggtta tcacaaacct tcactgcaat catggttaag tggaacattg agaaaaaatt    900
gtttgccttg tctttggata tgctagtgc aaatgaagta gctgtgcacg atataattga    960
ggatttgcag gacactgatt caaatctagt ttgtgatggt gctttctttc atgtgaggtg   1020
tgcttgtcac atactgaact tggttgcaaa ggatggcttg gctgtaattg caggaacaat   1080
tgagaaaatc aaagcgattg ttcttgctgt aaaatcttct cctttgcagt gggaagaact   1140
aatgaagtgt gctagtgaat gtgacttgga taaatctaaa gggatctcat atgatgtctc   1200
aactagatgg aattcaacct atttgatgtt gagggatgcc ttatattata gcctgcact    1260 aataaggctt aaaacaagtg atcctcgcag gtacgatgca atttgtccta aagccgagga   1320
gtggaagatg gcattaactc ttttttaagtg tttgaagaag ttttttgatc tcactgaact   1380
cctatctggt actcaatatt ccactgcaaa tttattttac aaaggtttct gtgagataaa   1440
ggatttgatt gaccaatggt gtgttcatga aaaatttgtc attaggagaa tggccgttgc   1500
aatgagtgaa aagtttgaga aatattggaa agtgtctaat attgcactag ctgtagcatg   1560
cttccttgac cctaggtaca agaaaatatt gattgagttc tatatgaaaa aatttcatgg   1620
tgattcatac aaagttcatg tagatgactt tgttagggtc attagaaaat tgtatcaatt   1680
ctattctagt tgtagtcctt cagctccaaa gacaaagaca actactaatg atagtatgga   1740
tgataccttg atggaaaatg aagatgatga atttcaaaac tatttgcatg agttgaagga   1800
ttatgatcaa gtagagtcaa atgaattgga taaatatatg tctgaaccc ttttgaagca    1860 tagtggtcag tttgatattt tatcatggtg gaggggaagg gttgcagaat atcctattct   1920
cacccaaatt gcaagggatg tgctagcaat acaagtgtca actgttgctt ctgagtctgc   1980
gttcagtgct ggtggtcgtg ttgttgatcc ttaccgcaat cgtcttggtt cggagattgt   2040
tgaagctttg atatgcacaa aagattgggt agcagcatct agaaaaggtg ctacatattt   2100
tccaacaatg attggtgatc tcgaggtgct agactctgtt attgctgctg caacaaatca   2160
tgagaatcat atggatgagg atgaagacgc aatagaattt tctaagaata tgaagatgt    2220 agcaagtggc tcctctccat gagcaatgtg tcttatgttt gttgacagat gagccttggt   2280
tgtaatagtt tatgcatgct aagtgctcca gatgtgagca agtgattatg aatatgtgtt   2340
ttaaacttta tattgtgtca tgtgtgctag tagacttata tggcttctta tgttagccaa   2400
g                                                                   2401
```

<210> SEQ ID NO 55
<211> LENGTH: 3334
<212> TYPE: DNA
<213> ORGANISM: Artificial
<220> FEATURE:
<223> OTHER INFORMATION: pEGFP-N1 plasmid fragment

<400> SEQUENCE: 55

| | | | | | |
|---|---|---|---|---|---|
| gcggccgcga | ctctagatca | taatcagcca | taccacattt | gtagaggttt | tacttgcttt | 60 |
| aaaaaacctc | ccacacctcc | ccctgaacct | gaaacataaa | atgaatgcaa | ttgttgttgt | 120 |
| taacttgttt | attgcagctt | ataatggtta | caaataaagc | aatagcatca | caaatttcac | 180 |
| aaataaagca | tttttttcac | tgcattctag | ttgtggtttg | tccaaactca | tcaatgtatc | 240 |
| ttaaggcgta | aattgtaagc | gttaatattt | tgttaaaatt | cgcgttaaat | ttttgttaaa | 300 |
| tcagctcatt | ttttaaccaa | taggccgaaa | tcggcaaaat | cccttataaa | tcaaaagaat | 360 |
| agaccgagat | agggttgagt | gttgttccag | tttggaacaa | gagtccacta | ttaaagaacg | 420 |
| tggactccaa | cgtcaaaggg | cgaaaaaccg | tctatcaggg | cgatggccca | ctacgtgaac | 480 |
| catcacccta | atcaagtttt | ttggggtcga | ggtgccgtaa | agcactaaat | cggaacccta | 540 |
| aagggagccc | ccgatttaga | gcttgacggg | gaaagccggc | gaacgtggcg | agaaaggaag | 600 |
| ggaagaaagc | gaaaggagcg | ggcgctaggg | cgctggcaag | tgtagcggtc | acgctgcgcg | 660 |
| taaccaccac | acccgccgcg | cttaatgcgc | cgctacaggg | cgcgtcaggt | ggcacttttc | 720 |
| ggggaaatgt | gcgcggaacc | cctatttgtt | tatttttcta | aatacattca | aatatgtatc | 780 |
| cgctcatgag | acaataaccc | tgataaatgc | ttcaataata | ttgaaaaagg | aagagtcctg | 840 |
| aggcggaaag | aaccagctgt | ggaatgtgtg | tcagttaggg | tgtggaaagt | ccccaggctc | 900 |
| cccagcaggc | agaagtatgc | aaagcatgca | tctcaattag | tcagcaacca | ggtgtggaaa | 960 |
| gtccccaggc | tccccagcag | gcagaagtat | gcaaagcatg | catctcaatt | agtcagcaac | 1020 |
| catagtcccg | cccctaactc | cgcccatccc | gcccctaact | ccgcccagtt | ccgcccattc | 1080 |
| tccgccccat | ggctgactaa | ttttttttat | ttatgcagag | gccgaggccg | cctcggcctc | 1140 |
| tgagctattc | cagaagtagt | gaggaggctt | ttttggaggc | ctaggctttt | gcaaagatcg | 1200 |
| atcaagagac | aggatgagga | tcgtttcgca | tgattgaaca | agatggattg | cacgcaggtt | 1260 |
| ctccggccgc | ttgggtggag | aggctattcg | gctatgactg | gcacaacag | acaatcggct | 1320 |
| gctctgatgc | cgccgtgttc | cggctgtcag | cgcaggggcg | cccggttctt | tttgtcaaga | 1380 |
| ccgacctgtc | cggtgccctg | aatgaactgc | aagacgaggc | agcgcggcta | tcgtggctgg | 1440 |
| ccacgacggg | cgttccttgc | gcagctgtgc | tcgacgttgt | cactgaagcg | ggaagggact | 1500 |
| ggctgctatt | gggcgaagtg | ccggggcagg | atctcctgtc | atctcacctt | gctcctgccg | 1560 |
| agaaagtatc | catcatggct | gatgcaatgc | ggcggctgca | tacgcttgat | ccggctacct | 1620 |
| gcccattcga | ccaccaagcg | aaacatcgca | tcgagcgagc | acgtactcgg | atggaagccg | 1680 |
| gtcttgtcga | tcaggatgat | ctggacgaag | agcatcaggg | gctcgcgcca | gccgaactgt | 1740 |
| tcgccaggct | caaggcgagc | atgcccgacg | gcgaggatct | cgtcgtgacc | catggcgatg | 1800 |
| cctgcttgcc | gaatatcatg | gtggaaaatg | gccgcttttc | tggattcatc | gactgtggcc | 1860 |
| ggctgggtgt | ggcggaccgc | tatcaggaca | tagcgttggc | tacccgtgat | attgctgaag | 1920 |
| agcttggcgg | cgaatgggct | gaccgcttcc | tcgtgcttta | cggtatcgcc | gctcccgatt | 1980 |
| cgcagcgcat | cgccttctat | cgccttcttg | acgagttctt | ctgagcggga | ctctggggtt | 2040 |
| cgaaatgacc | gaccaagcga | cgcccaacct | gccatcacga | gatttcgatt | ccaccgccgc | 2100 |
| cttctatgaa | aggttgggct | tcggaatcgt | tttccgggac | gccggctgga | tgatcctcca | 2160 |

```
gcgcggggat ctcatgctgg agttcttcgc ccaccctagg gggaggctaa ctgaaacacg    2220
gaaggagaca ataccggaag gaacccgcgc tatgacggca ataaaaagac agaataaaac    2280
gcacggtgtt gggtcgtttg ttcataaacg cggggttcgg tcccagggct ggcactctgt    2340
cgatacccca ccgagacccc attggggcca atacgcccgc gtttcttcct tttccccacc    2400
ccacccccca agttcgggtg aaggcccagg gctcgcagcc aacgtcgggg cggcaggccc    2460
tgccatagcc tcaggttact catatatact ttagattgat ttaaaacttc attttttaatt   2520 taaaaggatc taggtgaaga tccttttttga taatctcatg accaaaatcc cttaacgtga    2580
gttttcgttc cactgagcgt cagacccccgt agaaaagatc aaaggatctt cttgagatcc    2640 ttttttttctg cgcgtaatct gctgcttgca acaaaaaaaa ccaccgctac cagcggtggt    2700
ttgtttgccg atcaagagc taccaactct ttttccgaag gtaactggct tcagcagagc    2760
gcagatacca aatactgtcc ttctagtgta gccgtagtta ggccaccact tcaagaactc    2820
tgtagcaccc cctacatacc tcgctctgct aatcctgtta ccagtggctg ctgccagtgg    2880
cgataagtcg tgtcttaccg ggttggactc aagacgatag ttaccggata aggcgcagcg    2940
gtcgggctga acggggggtt cgtgcacaca gcccagcttg gagcgaacga cctacaccga    3000
actgagatac ctacagcgtg agctatgaga agcgccacg cttcccgaag ggagaaaggc    3060
ggacaggtat ccggtaagcg gcagggtcgg aacaggagag cgcacgaggg agcttccagg    3120
gggaaacgcc tggtatcttt atagtcctgt cgggtttcgc cacctctgac ttgagcgtcg    3180 attttttgtga tgctcgtcag gggggcgag cctatggaaa aacgccagca acgcggcctt    3240
tttacggttc ctggccttttt gctggccttt tgctcacatg ttctttcctg cgttatcccc    3300
tgattctgtg gataaccgta ttaccgccat gcat                               3334
```

<210> SEQ ID NO 56
<211> LENGTH: 259
<212> TYPE: DNA
<213> ORGANISM: Artificial
<220> FEATURE:
<223> OTHER INFORMATION: Zea mays Ds flanked by human DNA

<400> SEQUENCE: 56

```
atcggttata cgatacggtc ggtacgggat tttcccatcc tactttcatc cctgagtgag      60
actctgacgg cctcctgctt cccccacact gtggaaggtg gggctcccca agcctgcact     120
cctacctgag atgccagtct cttttgtctac tttagacacc aggttccaaa gaccctgtgc    180
tctcagatac cttttatgtc taaagcagag gccctacccc agcactcccc atctcagtag    240
acagtaactc catttacca                                                  259
```

<210> SEQ ID NO 57
<211> LENGTH: 253
<212> TYPE: DNA
<213> ORGANISM: Artificial
<220> FEATURE:
<223> OTHER INFORMATION: Zea mays Ds flanked by human DNA

<400> SEQUENCE: 57

```
agcacagggt ctttggaacc tggtgtctaa agtagacaaa gagactggca tctcaggtag      60
gagtgcaggc ttggggagcc ccaccttcca cagtgtgggg gaagcaggag gccgtcagag     120
tctcactcag ggatgaaagt aggatgggaa aatcccgtac cgaccgttat cgtataaccg     180
attttgttag tttatcccg atcgatttcg aacccgaggt aaaaaacgaa aacggaacgg     240
aaacggatat aca                                                         253
```

<210> SEQ ID NO 58
<211> LENGTH: 260
<212> TYPE: DNA
<213> ORGANISM: Artificial
<220> FEATURE:
<223> OTHER INFORMATION: Zea mays Ds flanked by human DNA

<400> SEQUENCE: 58
gggcctctgc tttagacata aaaggtatct gagagcacag ggtctttgga acctggtgtc    60
taaagtagac aaagagactg gcatctcagg taggagtgca ggcttgggga gccccacctt   120
ccacagtgtg ggggaagcag gaggccgtca gagtctcact cagggatgaa agtaggatgg   180
gaaaatcccg taccgaccgt tatcgtataa ccgattttgt tagttttatc ccgatcgatt   240
tcgaacccga ggtaaaaacg                                               260

<210> SEQ ID NO 59
<211> LENGTH: 265
<212> TYPE: DNA
<213> ORGANISM: Artificial
<220> FEATURE:
<223> OTHER INFORMATION: Zea mays Ds flanked by human DNA

<400> SEQUENCE: 59
gctttagaca taaaggtat ctgagagcac agggtctttg gaacctggtg tctaaagtag     60
acaaagagac tggcatctca ggtaggagtg caggcttggg gagccccacc ttccacagtg   120
tgggggaagc aggaggccgt cagagtctca ctcaggatg aaagtaggat gggaaaatcc    180
cgtaccgacc gttatcgtat aaccgatttt gttagtttta tcccgatcga tttcgaaccc   240
gaggtaaaaa acgaaaacgg aacga                                         265

<210> SEQ ID NO 60
<211> LENGTH: 250
<212> TYPE: DNA
<213> ORGANISM: Artificial
<220> FEATURE:
<223> OTHER INFORMATION: Zea mays Ds flanked by human DNA

<400> SEQUENCE: 60
actggcaaca ccgcctcttg ttctcctcta tttccagcat ccagaaaagt gtctggctta    60
tccttggtgc tccataaatt tttactgaat gaatgaataa atgaattcat gaatgaacag   120
gatggctagt gagactaggg atgaaaacgg tcggtaacgg tcggtaaaat acctctaccg   180
ttttcatttt catatttaac ttgcgggacg gaaacgaaaa cgggatatac cggtaacgaa   240
aacgaacggg                                                          250

<210> SEQ ID NO 61
<211> LENGTH: 218
<212> TYPE: DNA
<213> ORGANISM: Artificial
<220> FEATURE:
<223> OTHER INFORMATION: Zea mays Ds flanked by human DNA

<400> SEQUENCE: 61
gactggcaac accgcctctt gttctcctct atttccagca tccagaaaag tgtctggctt    60
atccttggtg ctccataaat ttttactgaa tgaatgaata aatgaattca tgaatgaaca   120
ggatggctag tgagactagg gatgaaaacg gtcggtaacg gtcggtaaaa tacctctacc   180
gttttcattt tcatatttaa cttgcgggac ggaaacga                           218

```
<210> SEQ ID NO 62
<211> LENGTH: 44
<212> TYPE: DNA
<213> ORGANISM: Artificial
<220> FEATURE:
<223> OTHER INFORMATION: Insertion site of Ds construct in human DNA

<400> SEQUENCE: 62
ggaagcagga ggccgtcaga gtctcactca gggatgaaag tagg              44

<210> SEQ ID NO 63
<211> LENGTH: 44
<212> TYPE: DNA
<213> ORGANISM: Artificial
<220> FEATURE:
<223> OTHER INFORMATION: Insertion site of Ds construct in human DNA

<400> SEQUENCE: 63
accgttttca tccctagtct cactagccat cctgttcatt catg              44

<210> SEQ ID NO 64
<211> LENGTH: 479
<212> TYPE: DNA
<213> ORGANISM: Artificial
<220> FEATURE:
<223> OTHER INFORMATION: Zea mays Ds flanked by human DNA

<400> SEQUENCE: 64
aatatgaaaa tgaaaacggt agaggtattt taccgaccgt taccgaccgt tttcatccct      60
atatagatgc atgtttagag aggactgagg gggcaactga atgtgtttaa tttcaagctt     120
actatgtgat catgaaatac ccaacacatt atgctggtac aaatccagag ttctaaactg     180
agaccgaggt ggcatatgca tatttgagag ttagcagcat aaagatacta attgaagcta     240
tgaaacagat gtgattaatt tggaggagaa taattagaga aaaataatag gtcaaagaca     300
gactcctgag gaaccccaac attttaaggg acacaaaaga ggttgaaaag agacagccag     360
agaggtaaaa ggaaaaccag aaatgcttgg agtgagaaaa gccaagtaaa gagggtattt     420
caagcaaaag tagtcaacag tgtgtttcct aaacacgtgc agactgattg gaagctaga      479

<210> SEQ ID NO 65
<211> LENGTH: 501
<212> TYPE: DNA
<213> ORGANISM: Artificial
<220> FEATURE:
<223> OTHER INFORMATION: Zea mays Ds flanked by human DNA

<400> SEQUENCE: 65
ctgttgacta cttttgcttg aataccctct ttacttggct tttctcactc caagcatttc      60
tggttttcct tttacctctc tggctgtctc ttttcaacct cttttgtgtc ccttaaaatg     120
ttggggttcc tcaggagtct gtctttgacc tattattttt ctctaattat tctcctccaa     180
attaatcaca tctgtttcat agcttcaatt agtatcttta tgctgctaac tctcaaatat     240
gcatatgcca cctcggtctc agtttacaac tctggatttg taccagcata atgtgttggg     300
tatttcatga tcacatagta agcttgaaat taaacacatt cagttgcccc ctcagtcctc     360
tctaaacatg catctatata gggatgaaaa cggtcggtaa cggtcggtaa aatacctcta     420
ccgttttcat tttcatattt aacttgcggg acgaaacga aacgggata taccggtaac     480 gaaaacgaac gggataaata c                                              501

<210> SEQ ID NO 66
<211> LENGTH: 393
```

-continued

<212> TYPE: DNA
<213> ORGANISM: Artificial
<220> FEATURE:
<223> OTHER INFORMATION: Zea mays Ds flanked by human DNA

<400> SEQUENCE: 66

| tccgtcccgc aagttaaata tgaaaatgaa acggtagag gtattttacc gaccgttacc | 60 |
| gaccgttttc atccctagtg agagtctgct cttctgtaaa cagacggctg aaattgctga | 120 |
| aaatcagaca caagctgtta ctatgcaagt gattgacctg caacgaaagg tacatgctca | 180 |
| gcctcactgg atgtctactg ttaaagggag gacattgatt ggaaagagt gggaccctga | 240 |
| aagttgagat ggggacacgt cgagggggcc taatgaagct gggaatactg agataataaa | 300 |
| ttctgatgag ccttttttagc aagagggaat cgcctcccca ccccagtgg tagaaacatg | 360 |
| cccttgccca tctactgcag taccaggctt tca | 393 |

<210> SEQ ID NO 67
<211> LENGTH: 362
<212> TYPE: DNA
<213> ORGANISM: Artificial
<220> FEATURE:
<223> OTHER INFORMATION: Zea mays Ds flanked by human DNA

<400> SEQUENCE: 67

| atatgaaaat gaaacggta gaggtatttt accgaccgtt accgaccgtt ttcatcccta | 60 |
| gtgagagtct gctcttctgt aaacagacgg ctgaaattgc tgaaaatcag acacaagctg | 120 |
| ttactatgca agtgattgac ctgcaacgaa aggtacatgc tcagcctcac tggatgtcta | 180 |
| ctgttaaagg gaggacattg attggaaaag agtgggaccc tgaaagttga gatggggaca | 240 |
| cgtcgagggg ccctaatgaa gctgggaata ctgagataat aaattctgat gagcctttt | 300 |
| agcaagaggg aatcgcctcc caccccag tggtagaaac atgcccttgc ccatctactg | 360 |
| ca | 362 |

<210> SEQ ID NO 68
<211> LENGTH: 25
<212> TYPE: DNA
<213> ORGANISM: Artificial
<220> FEATURE:
<223> OTHER INFORMATION: Zea mays Ds flanked by vector DNA

<400> SEQUENCE: 68

| tggagctccc cgactaggga tgaaa | 25 |

<210> SEQ ID NO 69
<211> LENGTH: 25
<212> TYPE: DNA
<213> ORGANISM: Artificial
<220> FEATURE:
<223> OTHER INFORMATION: Zea mays Ds flanked by vector DNA

<400> SEQUENCE: 69

| tttcatccct gcgtcgggta cccaa | 25 |

<210> SEQ ID NO 70
<211> LENGTH: 6495
<212> TYPE: DNA
<213> ORGANISM: Artificial
<220> FEATURE:
<223> OTHER INFORMATION: Ds Construct

<400> SEQUENCE: 70

| cagggatgaa agtaggatgg gaaaatcccg taccgaccgt tatcgtataa ccgattttgt | 60 |

```
tagtttatc  ccgatcgatt  tcgaacccga  ggtaaaaaac  gaaaacgaaa  cggaaacggg    120
atatacaaaa  cggtaaacgg  aaacggaaac  ggtagagcta  gtttcccgac  cgtttcaccg    180
ggatcccgtt  tttaatcggg  atgatcccgt  ttcgttaccg  tattttctaa  ttcgggatga    240
ctgcaacaga  tccctcgagc  gcttaagttt  aaacgcgtta  caattggcc   ataatagtaa    300 tcaattacgg  ggtcattagt  tcatagccca  tatatggagt  tccgcgttac  ataacttacg    360
gtaaatggcc  cgcctggctg  accgcccaac  gacccccgcc  cattgacgtc  aataatgacg    420
tatgttccca  tagtaacgcc  aatagggact  ttccattgac  gtcaatgggt  ggagtattta    480
cggtaaactg  cccacttggc  agtacatcaa  gtgtatcata  tgccaagtac  gccccctatt    540
gacgtcaatg  acggtaaatg  gcccgcctgg  cattatgccc  agtacatgac  cttatgggac    600
tttcctactt  ggcagtacat  ctacgtatta  gtcatcgcta  ttaccatggt  gatgcggttt    660
tggcagtaca  tcaatgggcg  tggatagcgg  tttgactcac  ggggatttcc  aagtctccac    720
cccattgacg  tcaatgggag  tttgttttgg  caccaaaatc  aacgggactt  tccaaaatgt    780
cgtaacaact  ccgccccatt  gacgcaaatg  gcggtaggc   gtgtacggtg  gaggtctat    840 ataagcagag  ctggtttagt  gaaccgtcag  atccgctagc  gctaccggac  tcagatctcg    900
agctcaagct  tcgaattctg  cagtcgacgg  taccgcgggc  ccgggatcca  tcgccaccat    960
ggtgagcaag  ggcgaggagc  tgttcaccgg  ggtggtgccc  atcctggtcg  agctggacgg   1020
cgacgtaaac  ggccacaagt  tcagcgtgtc  cggcgagggc  gagggcgatg  ccacctacgg   1080
caagctgacc  ctgaagttca  tctgcaccac  cggcaagctg  cccgtgccct  ggcccaccct   1140
cgtgaccacc  ctgacctacg  gcgtgcagtg  cttcagccgc  taccccgacc  acatgaagca   1200
gcacgacttc  ttcaagtccg  ccatgcccga  aggctacgtc  caggagcgca  ccatcttctt   1260
caaggacgac  ggcaactaca  agacccgcgc  cgaggtgaag  ttcgagggcg  acaccctggt   1320
gaaccgcatc  gagctgaagg  gcatcgactt  caaggaggac  ggcaacatcc  tggggcacaa   1380
gctggagtac  aactacaaca  gccacaacgt  ctatatcatg  gccgacaagc  agaagaacgg   1440
catcaaggtg  aacttcaaga  tccgccacaa  catcgaggac  ggcagcgtgc  agctcgccga   1500
ccactaccag  cagaacaccc  ccatcggcga  cggccccgtg  ctgctgcccg  acaaccacta   1560
cctgagcacc  cagtccgccc  tgagcaaaga  ccccaacgag  aagcgcgatc  acatggtcct   1620
gctggagttc  gtgaccgccg  ccgggatcac  tctcggcatg  gacgagctgt  acaagtaaag   1680
cggccgcgat  atcgctagct  cgagatcggg  agatctggcc  tccgcgcggg  ttttggcgc    1740 cccccgcggg  cgcccctcc   tcacggcgag  cgctgccacg  tcagacgaag  ggcgcacgag   1800
cgtcctgatc  cttccgcccg  gacgctcagg  acagcggccc  gctgctcata  agactcggcc   1860
ttagaacccc  agtatcagca  gaaggacatt  ttaggacggg  acttgggtga  ctctagggca   1920
ctggttttct  ttccagagag  cggaacaggc  gaggaaaagt  agtcccttct  cggcgattct   1980
gcggagggat  ctccgtgggg  cggtgaacgc  cgatgattat  ataaggacgc  gccgggtgtg   2040
gcacagctag  ttccgtcgca  gccgggattt  gggtcgcggt  tcttgtttgt  ggatcgctgt   2100
gatcgtcact  tggtgagtag  cgggctgctg  ggctggccgg  ggctttcgtg  gccgccgggc   2160
cgctcggtgg  gacggaagcg  tgtggagaga  ccgccaaggg  ctgtagtctg  ggtccgcgag   2220
caaggttgcc  ctgaactggg  ggttgggggg  agcgcagcaa  aatggcggct  gttcccgagt   2280
cttgaatgga  agacgcttgt  gaggcgggct  gtgaggtcgt  tgaaacaagg  tgggggcat    2340 ggtgggcggc  aagaacccaa  ggtcttgagg  ccttcgctaa  tgcgggaaag  ctcttattcg   2400
ggtgagatgg  gctggggcac  catctgggga  ccctgacgtg  aagtttgtca  ctgactggag   2460
```

```
aactcggttt gtcgtctgtt gcggggcgg cagttatggc ggtgccgttg ggcagtgcac    2520 ccgtacctt ggagcgcgc gccctcgtcg tgtcgtgacg tcacccgttc tgttggctta    2580
taatgcaggg tgggccacc tgccggtagg tgtgcggtag gcttttctcc gtcgcaggac    2640
gcagggttcg ggcctagggt aggctctcct gaatcgacag gcgccggacc tctggtgagg    2700
ggagggataa gtgaggcgtc agtttctttg gtcggttta tgtacctatc ttcttaagta    2760
gctgaagctc cggttttgaa ctatgcgctc ggggttggcg agtgtgtttt gtgaagtttt    2820
ttaggcacct tttgaaatgt aatcatttgg gtcaatatgt aattttcagt gttagactag    2880
taaattgtcc gctaaattct ggccgttttt ggctttttg ttagaccgga ccgtgttgac    2940
aattaatcat cggcatagta tatcggcata gtataaatacg acaaggtgag gaactaaacc    3000
atggccaagc ctttgtctca agaagaatcc accctcattg aaagagcaac ggctacaatc    3060
aacagcatcc ccatctctga agactacagc gtcgccagcg cagctctctc tagcgacggc    3120
cgcatcttca ctggtgtcaa tgtatatcat tttactgggg gaccttgtgc agaactcgtg    3180
gtgctgggca ctgctgctgc tgcggcagct ggcaacctga cttgtatcgt cgcgatcgga    3240
aatgagaaca ggggcatctt gagccctcgc ggacggtgcc gacaggtgct tctcgatctg    3300
catcctggga tcaaagccat agtgaaggac agtgatggac agccgacggc agttgggatt    3360
cgtgaattgc tgccctctgg ttatgtgtgg gagggctaag cacttcgtgg ccgaggagca    3420
ggactgacac tcgacctcga acttgttta ttgcagctta taatggttac aaataaagca    3480
atagcatcac aaatttcaca aataaagcat ttttttcact gcattctagt tgtggtttgt    3540
ccaaactcat caatgtatct tatcatgtct gaattcccgg ggatcctcta gactgtcaga    3600
ccaagtttac tcatatatac tttagattga tttaaaactt catttttaat ttaaaaggat    3660
ctaggtgaag atccttttg ataatctcat gaccaaaatc ccttaacgtg agttttcgtt    3720
ccactgagcg tcagaccccg tagaaaagat caaaggatct tcttgagatc cttttttctc    3780
gcgcgtaatc tgctgcttgc aaacaaaaaa accaccgcta ccagcggtgg tttgtttgcc    3840
ggatcaagag ctaccaactc ttttttccgaa ggtaactggc ttcagcagag cgcagatacc    3900
aaatactgtt cttctagtgt agccgtagtt aggccaccac ttcaagaact ctgtagcacc    3960
gcctacatac ctcgctctgc taatcctgtt accagtggct gctgccagtg gcgataagtc    4020
gtgtcttacc gggttggact caagacgata gttaccggat aaggcgcagc ggtcgggctg    4080 aacgggggt tcgtgcacac agcccagctt ggagcgaacg acctacaccg aactgagata    4140
cctacagcgt gagctatgag aaagcgccac gcttcccgaa gggagaaagg cggacaggta    4200
tccggtaagc ggcagggtcg gaacaggaga gcgcacgagg gagcttccag ggggaaacgc    4260
ctggtatctt tatagtcctg tcgggtttcg ccacctctga cttgagcgtc gatttttgtg    4320
atgctcgtca gggggcgga gcctatggaa aaacgccagc aacgcggcct ttttacggtt    4380
cccggccttt tgctggcctt tgctcacat gctgggccca gccggccaga tctgagctcg    4440
cggccgcgat atcgctagct cgagggactt atatggcttc ttatgttagc caagagccca    4500
agacttatca cttatgtgct acattaaact atgtgtgctc cagatttata tggattttat    4560
ctatgtttaa ttaagacttg tgtttacaat tttttatatt tgtttttaag ttttgaatat    4620
atgttttcat gtgtgatttt accgaacaaa aataccggtt cccgtccgat ttcgacttta    4680
acccgaccgg atcgtatcgg ttttcgatta ccgtatttat cccgttcgtt ttcgttaccg    4740
gtatatcccg ttttcgtttc cgtcccgcaa gttaaatatg aaaatgaaaa cggtagaggt    4800
attttaccga ccgttaccga ccgttttcat ccctatgcat tctgacagtt accaatgctt    4860
```

```
aatcagtgag gcacctatct cagcgatctg tctatttcgt tcatccatag ttgcctgact    4920
ccccgtcgtg tagataacta cgatacggga gggcttacca tctggcccca gtgctgcaat    4980
gataccgcga gacccacgct caccggctcc agatttatca gcaataaacc agccagccgg    5040
aagggccgag cgcagaagtg gtcctgcaac tttatccgcc tccatccagt ctattaattg    5100
ttgccgggaa gctagagtaa gtagttcgcc agttaatagt ttgcgcaacg ttgttgccat    5160
tgctacaggc atcgtggtgt cacgctcgtc gtttggtatg gcttcattca gctccggttc    5220
ccaacgatca aggcgagtta catgatcccc catgttgtgc aaaaaagcgg ttagctcctt    5280
cggtcctccg atcgttgtca gaagtaagtt ggccgcagtg ttatcactca tggttatggc    5340
agcactgcat aattctctta ctgtcatgcc atccgtaaga tgcttttctg tgactggtga    5400
gtactcaacc aagtcattct gagaatagtg tatgcggcga ccgagttgct cttgcccggc    5460
gtcaatacgg gataataccg cgccacatag cagaacttta aaagtgctca tcattggaaa    5520
acgttcttcg gggcgaaaac tctcaaggat cttaccgctg ttgagatcca gttcgatgta    5580
acccactcgt gcacccaact gatcttcagc atcttttact ttcaccagcg tttctgggtg    5640
agcaaaaaca ggaaggcaaa atgccgcaaa aaagggaata agggcgacac ggaaatgttg    5700
aatactcata ctcttccttt ttcaatataa ttgaagcatt tatcagggtt attgtctcat    5760
gagcggatac atatttgaat gtatttagaa aaataaacaa ataggggttc gcgcacatt     5820
tccccgaaaa gtgccaccta aattgtaagc gttaatattt tgttaaaatt cgcgttaaat    5880
ttttgttaaa tcagctcatt ttttaaccaa taggccgaaa tcggcaaaat cccttataaa    5940
tcaaaagaat agaccgagat agggttgagt gttgttccag tttggaacaa gagtccacta    6000
ttaaagaacg tggactccaa cgtcaaaggg cgaaaaaccg tctatcaggg cgatggccca    6060
ctacgtgaac catcacccta atcaagtttt ttggggtcga ggtgccgtaa agcactaaat    6120
cggaacccta aagggagccc ccgatttaga gcttgacggg gaaagccggc gaacgtggcg    6180
agaaaggaag ggaagaaagc gaaaggagcg ggcgctaggg cgctggcaag tgtagcggtc    6240
acgctgcgcg taaccaccac acccgccgcg cttaatgcgc cgctacaggg cgcgtcccat    6300
tcgccattca ggctgcgcaa ctgttgggaa gggcgatcgg tgcgggcctc ttcgctatta    6360
cgccagctgg cgaaaggggg atgtgctgca aggcgattaa gttgggtaac gccagggttt    6420
tcccagtcac gacgttgtaa aacgacggcc agtgaattga tacgactcac tatagggcga    6480
attgggtacc cgacg                                                     6495
```

<210> SEQ ID NO 71
<211> LENGTH: 6400
<212> TYPE: DNA
<213> ORGANISM: Artificial
<220> FEATURE:
<223> OTHER INFORMATION: Ac-TPase Construct

<400> SEQUENCE: 71

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
```

```
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatcc gctagcgcta    600
ccggactcag atctcgagct caagcttcga attctgcagt cgacggtacc gcgggcccgg    660
gatccatacg atttaggtga cactatagaa tacaagcttg cttgttcttt ttgcagaagc    720
tcagaataaa cgctcaactt tggcagatcc gccaccatgg gtcctccaga gaagaagcgt    780
aaggtagaaa tggctattgt tcatgaacca caaccacaac cacaaccaca accagaacca    840
caaccacagc cacaacctga acccgaagaa gaagcaccac agaagagggc aaagaagtgc    900
acatcggatg tatggcagca tttcaccaag aaggaaattg aagtggaggt cgatggaaag    960
aaatacgttc aggtatgggg gcattgcaac tttcctaatt gcaaggctaa gtatagggct   1020
gagggtcatc atggaacaag cggatttcga aatcacttga aacatcaca tagtttagtt   1080 aaaggtcagt tgtgtctaaa aagtgaaaag gatcatggca aagacataaa tctcattgag   1140
ccttataagt acgatgaagt ggttagccta aagaagcttc atttggcaat aatcatgcat   1200
gaatacccct tcaatattgt agaacatgag tactttgttg agtttgttaa gtctctgcgc   1260
cctcactttc aataaagtc ccgtgtcact gctagaaaat atatcatgga tttgtatttg   1320
gaagaaaaag aaaagttgta tggaaaacta aaagatgttc agtctcgctt cagtacaact   1380
atggatatgt ggacatcttg tcaaaataag tcatacatgt gtgtcaccat ccattggatt   1440
gatgatgatt ggtgtctcca aaaagaatt gttggcttt tcatgttga agggcgccac   1500 actggccaaa ggttatcaca aaccttcact gcaatcatgg ttaagtggaa cattgagaaa   1560
aaattgtttg ccttgtcttt ggataatgct agtgcaaatg aagtagctgt gcacgatata   1620
attgaggatt tgcaggacac tgattcaaat ctagtttgtg atggtgcttt ctttcatgtg   1680
aggtgtgctt gtcacatact gaacttggtt gcaaaggatg gcttggctgt aattgcagga   1740
acaattgaga aaatcaaagc gattgttctt gctgtaaaat cttctccttt gcagtgggaa   1800
gaactaatga agtgtgctag tgaatgtgac ttggataaat ctaaagggat ctcatatgat   1860
gtctcaacta gatggaattc aacctatttg atgttgaggg atgccttata ttataagcct   1920
gcactaataa ggcttaaaac aagtgatcct cgcaggtacg atgcaatttg tcctaaagcc   1980
gaggagtgga agatggcatt aactcttttt aagtgtttga agaagttttt tgatctcact   2040
gaactcctat ctggtactca atattccact gcaaatttat tttacaaagg tttctgtgag   2100
ataaaggatt tgattgacca atggtgtgtt catgaaaaat ttgtcattag gagaatggcc   2160
gttgcaatga gtgaaaagtt tgagaaatat tggaaagtgt ctaatattgc actagctgta   2220
gcatgcttcc ttgaccctag gtacaagaaa atattgattg agttctatat gaaaaaattt   2280
catggtgatt catacaaagt tcatgtagat gactttgtta gggtcattag aaaattgtat   2340
caattctatt ctagttgtag tccttcagct ccaaagacaa agacaactac taatgatagt   2400
atggatgata ccttgatgga aaatgaagat gatgaatttc aaaactattt gcatgagttg   2460
aaggattatg atcaagtaga gtcaaatgaa ttggataaat atatgtctga accccttttg   2520
aagcatagtg gtcagtttga tattttatca tggtggaggg gaagggttgc agaatatcct   2580
attctcaccc aaattgcaag ggatgtgcta gcaatacaag tgtcaactgt tgcttctgag   2640
tctgcgttca gtgctggtgg tcgtgttgtt gatccttacc gcaatcgtct tggttcggag   2700
attgttgaag ctttgatatg cacaaaagat tgggtagcag catctagaaa aggtgctaca   2760 tatttttccaa caatgattgg tgatctcgag gtgctagact ctgttattgc tgctgcaaca   2820
```

```
aatcatgaga atcatatgga tgaggatgaa gacgcaatag aatttctaa gaataatgaa   2880 gatgtagcaa gtggctcctc tccatgagca atgtgtctta tgtttgttga cagatgagcc   2940
ttggttgtaa tagtttatgc atgctaagtg ctccagatgt gagcaagtga ttatgaatat   3000
gtgttttaaa ctttatattg tgtcatgtgt gctagtagac ttatatggct tcttatgtta   3060
gccaaggcgg ccgcgactct agatcataat cagccatacc acatttgtag aggttttact   3120
tgctttaaaa aacctcccac acctcccccT gaacctgaaa cataaaatga atgcaattgt   3180
tgttgttaac ttgtttattg cagcttataa tggttacaaa taaagcaata gcatcacaaa   3240
tttcacaaat aaagcatttt tttcactgca ttctagttgt ggtttgtcca aactcatcaa   3300
tgtatcttaa ggcgtaaatt gtaagcgtta atattttgtt aaaattcgcg ttaaatttt   3360 gttaaatcag ctcattttt aaccaatagg ccgaaatcgg caaaatccct tataaatcaa   3420
aagaatagac cgagataggg ttgagtgttg ttccagtttg gaacaagagt ccactattaa   3480
agaacgtgga ctccaacgtc aaagggcgaa aaaccgtcta tcagggcgat ggcccactac   3540
gtgaaccatc accctaatca agttttttgg ggtcgaggtg ccgtaaagca ctaaatcgga   3600 acccataaagg gagcccccga tttagagctt gacggggaaa gccggcgaac gtggcgagaa   3660
aggaagggaa gaaagcgaaa ggagcgggcg ctagggcgct ggcaagtgta gcggtcacgc   3720
tgcgcgtaac caccacaccc gccgcgctta atgcgccgct acaggcgcg tcaggtggca   3780 cttttcgggg aaatgtgcgc ggaaccccta tttgtttatt tttctaaata cattcaaata   3840
tgtatccgct catgagacaa taaccctgat aaatgcttca ataatattga aaaaggaaga   3900
gtcctgaggc ggaaagaacc agctgtggaa tgtgtgtcag ttagggtgtg gaaagtcccc   3960
aggctcccca gcaggcagaa gtatgcaaag catgcatctc aattagtcag caaccaggtg   4020
tggaaagtcc ccaggctccc cagcaggcag aagtatgcaa agcatgcatc tcaattagtc   4080
agcaaccata gtcccgcccc taactccgcc catcccgccc ctaactccgc ccagttccgc   4140
ccattctccg ccccatggct gactaattt ttttatttat gcagaggccg aggccgcctc   4200
ggcctctgag ctattccaga agtagtgagg aggctttttt ggaggcctag cttttgcaa   4260 agatcgatca agagacagga tgaggatcgt ttcgcatgat tgaacaagat ggattgcacg   4320
caggttctcc ggccgcttgg gtggagaggc tattcggcta tgactgggca acagacaa    4380 tcggctgctc tgatgccgcc gtgttccggc tgtcagcgca ggggcgcccg gttcttttg    4440 tcaagaccga cctgtccggt gccctgaatg aactgcaaga cgaggcagcg cggctatcgt   4500
ggctggccac gacgggcgtt ccttgcgcag ctgtgctcga cgttgtcact gaagcgggaa   4560
gggactggct gctattgggc gaagtgccgg ggcaggatct cctgtcatct caccttgctc   4620
ctgccgagaa agtatccatc atggctgatg caatgcggcg gctgcatacg cttgatccgg   4680
ctacctgccc attcgaccac caagcgaaac atcgcatcga gcgagcacgt actcggatgg   4740
aagccggtct tgtcgatcag gatgatctgg acgaagagca tcaggggctc gcgccagccg   4800
aactgttcgc caggctcaag gcgagcatgc ccgacggcga ggatctcgtc gtgacccatg   4860
gcgatgcctg cttgccgaat atcatggtgg aaaatggccg cttttctgga ttcatcgact   4920
gtggccggct gggtgtggcg gaccgctatc aggacatagc gttggctacc cgtgatattg   4980
ctgaagagct tggcggcgaa tgggctgacc gcttcctcgt gctttacggt atcgccgctc   5040
ccgattcgca gcgcatcgcc ttctatcgcc ttcttgacga gttcttctga gcgggactct   5100
ggggttcgaa atgaccgacc aagcgacgcc caacctgcca tcacgagatt tcgattccac   5160
cgccgccttc tatgaaaggt tgggcttcgg aatcgttttc cgggacgccg gctggatgat   5220
```

```
cctccagcgc ggggatctca tgctggagtt cttcgcccac cctaggggga ggctaactga    5280
aacacggaag gagacaatac cggaaggaac ccgcgctatg acggcaataa aaagacagaa    5340
taaaacgcac ggtgttgggt cgtttgttca taaacgcggg gttcggtccc agggctggca    5400
ctctgtcgat accccaccga gaccccattg gggccaatac gcccgcgttt cttccttttc    5460
cccaccccac cccccaagtt cgggtgaagg cccagggctc gcagccaacg tcggggcggc    5520
aggccctgcc atagcctcag gttactcata tatactttag attgatttaa aacttcattt    5580
ttaatttaaa aggatctagg tgaagatcct ttttgataat ctcatgacca aaatccctta    5640
acgtgagttt tcgttccact gagcgtcaga ccccgtagaa aagatcaaag gatcttcttg    5700
agatcctttt tttctgcgcg taatctgctg cttgcaaaca aaaaaaccac cgctaccagc    5760
ggtggtttgt ttgccggatc aagagctacc aactcttttt ccgaaggtaa ctggcttcag    5820
cagagcgcag ataccaaata ctgtccttct agtgtagccg tagttaggcc accacttcaa    5880
gaactctgta gcaccgccta catacctcgc tctgctaatc ctgttaccag tggctgctgc    5940
cagtggcgat aagtcgtgtc ttaccgggtt ggactcaaga cgatagttac cggataaggc    6000
gcagcggtcg ggctgaacgg ggggttcgtg cacacagccc agcttggagc gaacgaccta    6060
caccgaactg agatacctac agcgtgagct atgagaaagc gccacgcttc ccgaagggag    6120
aaaggcggac aggtatccgg taagcggcag ggtcggaaca ggagagcgca cgagggagct    6180
tccaggggga aacgcctggt atctttatag tcctgtcggg tttcgccacc tctgacttga    6240
gcgtcgattt ttgtgatgct cgtcaggggg gcggagccta tggaaaaacg ccagcaacgc    6300 ggcctttta cggttcctgg ccttttgctg gccttttgct cacatgttct ttcctgcgtt    6360
atcccctgat tctgtggata accgtattac cgccatgcat                          6400
```

TRANSPOSITION OF MAIZE AC/DS ELEMENTS IN VERTEBRATES

CROSS-REFERENCE TO RELATED APPLICATIONS

The present application is a national stage filing under 35 U.S.C. §371 of PCT/SG2006/000121, filed on 11 May 2006, and claims the benefit of priority to U.S. Provisional Patent Application Ser. No. 60/681,447, filed 17 May 2005, each application is incorporated herein by reference in its entirety.

BACKGROUND OF THE INVENTION

The present invention is directed to the use of the maize Ac/Ds transposable elements in vertebrates, including fish, birds, and other animals including mammals and humans.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Transgenic animals, including fish, provide an excellent vertebrate model for studying many facets of development, physiology and disease. A wide variety of fish may be utilized for this purpose. Exemplary fish include teleost fish, such as zebrafish (*Danio rerio*), medaka (*Oryzias latipes*), mummichog (*Fundulus heteroclitus*), killifish (Genus *Fundulus*), catfish (Genus *Ictalurus*), such as channel catfish; carp (Genus *Cyprinus*), such as common carp; and trout or salmon (e.g., Genus *Salvelinus, Salmo,* and *Oncorhynchus*). Zebrafish have become an established model for investigating many facets of development, physiology and disease.

Zebrafish are particularly useful for studying many facets of development, physiology and disease. They are small, develop ex utero, and have a short generation time. At 5 days of age each fish is a free swimming/feeding organism complete with most of the organ systems employed by mammals, such as heart, brain, blood, and pancreas. Within the last 10 years, mutant zebrafish lines isolated from large-scale mutagenesis screens have led to a greater understanding of vertebrate development (Driever et al., 1996; Haffter et al., 1996; Golling et al., 2002). Although these studies have shown that zebrafish mutants can serve as good models for human diseases, zebrafish have not been widely used in this capacity. So far the biggest limitation in zebrafish research has been determining the identity of causative genes disrupted from these mutagenesis screens, as the vast majority of mutants have been created using the chemical mutagen N-Ethyl-N-nitrosourea (ENU). Identification of ENU-derived point mutations requires laborious and slow positional cloning efforts. Insertional mutagenesis using retrovirus, on the other hand, is effective, and a gene mutated in this way can take as little as 2 weeks to identify with minimal resources (Golling et al., 2002). By creating a bank of retroviral insertions in zebrafish sperm, a library can be created where at least one insert into roughly every gene is housed in a small freezer space. Characterization and determination of the genomic location of all the inserts will make it possible to easily perform reverse genetics in the zebrafish by using the sperm sample with the mutation of interest to fertilize eggs in vitro. In this way, researchers could save a great deal of time and money by ordering mutations of interest instead of random screening. An even more powerful use of the library would lie in forward genetic screens.

To date, the number of cloned ENU mutants in zebrafish remains extraordinarily low considering the number of labs currently working on the hundreds of mutant lines. About 100 genes mutated with ENU have been published since the completion of two large-scale ENU mutagenesis screens in 1996. In fact, many of these genes were not identified using strictly positional cloning efforts. Rather, they were found by recognizing that certain mutant phenotypes were similar to known *Drosophila* or mouse mutants whose genes and pathways had already been decoded (Talbot and Hopkins, 2000). In these instances a "candidate gene" approach was taken whereby each gene in the presumed developmental pathway was examined individually for mutations to correctly isolate the disruption. While this method has proven extremely successful in cloning mutant genes, it has not led to the discovery of novel genes/pathways and has mainly recapitulated that which is known about development from other organisms.

A more successful approach to cloning mutant genes in zebrafish has been to use pseudo-typed mouse retroviruses as the mutagen. These retroviruses have the vesicular stomatitis virus G coat protein that allows infection of a broad range of host cells including zebrafish (Yee et al., 1994; Emi et al., 1991; Burns et al., 1993). The viral DNA inserts into the genome as a single-copy entity in a mostly random fashion without altering its junctional sequence, although retroviruses have been seen to prefer 5' ends of genes as their insertion site (Vijaya et al., 1986; Rohdewohld et al., 1987; Mooslehner et al., 1990; Scherdin et al., 1990). Further, the retroviral insert serves as a molecular beacon, making it a rather simple process to link a mutant phenotype to a disrupted gene. One drawback is that the virus needs to be injected into zebrafish embryos at the 1000- to 2000-cell stage when the germ cells are still dividing (a necessary event for retrovirus integration). This requires more work up front than the traditional ENU mutagenesis method to create mutagenized founder fish. Since there are, on average, fewer retroviral insertions than ENU lesions per gamete, the mutagenic frequency of the retrovirus is less than that of chemical mutagens (1/1 ENU mutagenized F2 families produce a visible recessive mutation compared to 1/7 retroviral F2 families (Golling et al., 2002).

Recently, the retroviral method of mutagenesis has been used to conduct a large-scale developmental screen. That screen generated more than 500 mutants affecting zebrafish development; more than half of these disrupted genes were cloned (Golling et al., 2002; Amsternam et al., 1999). Results of this work have shown that all of the identified disrupted genes have homologues in human, but approximately 20% of these disrupted genes do not contain any obvious motifs or features that would allow one to classify the biochemical function of the resultant protein (Golling et al., 2002). In contrast, the genes so far cloned from ENU mutants show little degree of novelty.

One approach which has shown a great deal of promise for reverse genetics in zebrafish is the generation of gene knockdowns using morpholino based oligonucleotides (Heasman, 2002; Nasevicius and Ekker, 2000; Ekker, 2000). This technique relies on generating a short (24mer) morpholino oligonucleotide that is complimentary to the translation start site of the gene of interest (Summerton et al., 1997, Summerton and Weller, 1997). Injection of a morpholino oligonucleotide at the 1-2 cell stage inhibits translation of the endogenous target gene's mRNA. In this way many ENU derived mutant phenotypes have been phenocopied by injecting morpholino oligonucleotides specific to the mutated gene, establishing the proof in principle of the technique (Heasman, 2002; Nasevicius and Ekker, 2000; Ekker, 2000). These oligonucleotides have also been successfully used to examine unknown gene function of genes identified from in situ hybridization screens (Sakaguchi et al., 2001; Tsang et al., 2002).

While morpholino antisense technology is widely used in the zebrafish community it has some severe limitations. For instance, the window of opportunity for studying a knockdown of a favorite gene is only 2-3 days, thus limiting the technique primarily to the study of early development. Since the morpholino is not a stable, heritable element the amount of morpholino oligonucleotides in each cell is diminished by degradation and dilution with every round of division. Hence, if the desired gene is not expressed within this time period, which may presumably be the case with many disease genes, then this method will not work. The ability to perform suppressor or enhancer modifier screens would also be limited with morpholino oligonucleotides as each embryo in the screen would need to be injected with the oligonucleotide, a very time consuming effort.

Recent advances in producing high-titer retrovirus have greatly simplified its use in zebrafish. Some of the first retroviral constructs used for insertional mutagenesis in zebrafish generated injected (founder) fish that transmitted proviral integrations to only 5% of their F1 progeny (Lin et al., 1994). The number of inserts carried by these $F_1$ fish was also low, usually one insert per gamete and fewer than 5 total insertions per germ-line (Lin et al., 1994). To do any meaningful mutagenesis screens with these constructs one would have to inject zebrafish embryos for a period of many years to generate 500,000 inserts. As seen in Chen et al. (2002), new retroviral vectors have significantly reduced this time frame. Now two people injecting retrovirus could make enough founder fish to harbor a half-million inserts in two months time (Chen et al., 2002). Furthermore, the efficiency of the retroviral system now allows more than 25 different insertions on average for each founder fish. These fish can easily be raised, tagged for individual identification system with a novel marking system, and stored in approximately 200 fish tanks, which is a small sized aquatic facility for a researcher.

Insertional mutagenesis is now the quickest method for cloning mutated genes in the zebrafish. Not only does the retroviral insert serve as a molecular tag for the disrupted gene, it also serves as a valuable marker to establish genetic linkage with the mutant phenotype. Chemical mutagenesis methods must rely on establishing tight linkage of the disrupted gene to a marker, thereby narrowing the genomic region of interest to a size small enough that it can be managed by sequencing of a BAC or PAC clone. The complication with chemical mutagenesis derives from the fact that there are hundreds of markers to test and they must be tested on a significant number (a few thousand) of recombinant fish to show that the linked marker does not segregate from the mutant locus. In screening for embryonic mutations, generating a few thousand mutant embryos is not usually a problem. However, if one were to look for adult phenotypes, such as those particular to certain diseases (diabetes, Parkinson's, obesity, etc.), it would take an inordinate amount of time, space, and resources to raise all of the required recombinants to find a linked locus. With insertional mutagenesis, linkage is established simply by running a Southern blot of the restriction enzyme digested DNA from the mutant fish and the pairs of adult fish that generated the mutants. Using a labeled portion of the retrovirus as a probe, one would expect all of the mutant fish and their parents to have one band migrating at the same molecular size, while pairs of fish that did not produce phenotypic clutches would not have the same insert (i.e., both fish would not have the linked band). In this way one would only have to look at a handful of affected fish to generate a probable lead on the disrupted gene.

The most time consuming aspect of cloning genes disrupted by insertional mutagenesis has been in cases where the genomic DNA flanking the retroviral insert does not contain exonic or known gene sequences. Usually when the candidate linked insertion is identified and its flanking sequence is cloned, it is no longer than a few kilobases in length due to the ineffectiveness of PCR to amplify larger fragments. In previous work, it was found that about one-third of the flanking DNA cloned in this way did not have useful information in that their sequences did not reveal any homology or identity in database searches (G. Golling, unpublished result). This will no longer be a problem as the first draft of the zebrafish genome will be completed soon and it should be possible to identify which gene is disrupted by sequencing less than 50 bases of DNA flanking the retroviral insert.

Reverse genetic approaches in mouse have provided many insights into human diseases. Researchers have been able to take a gene of interest and disrupt its expression by homologous recombination in ES cells, then re-introduce those cells back into an embryo to create targeted transgenic knock-outs. While this approach has not yet proven successful in zebrafish or other vertebrate model organisms other than the mouse and rat, another method, called target-selected mutagenesis, has been developed to create targeted disruptions in specific genes of interest. Target-selected mutagenesis is accomplished by first mutagenizing germ-line DNA of an organism and then using PCR to amplify the gene of interest. Sequencing the PCR product for comparison to the wild type gene then identifies samples containing mutations in the gene of interest. Wienholds et al. have recently used this technique in zebrafish to isolate mutations in the Rag1 gene. By sequencing two exons of Rag1 from a sperm library consisting of nearly 2700 randomly ENU mutagenized males, the researchers found 15 mutations, one of which was a premature stop codon (Wienholds et al., 2002). While the methodology does in fact work, it may be cumbersome for large-scale screening. To identify the single stop mutation approximately 12,500 sequencing reactions were carried out over a period of two months (Wienholds et al., 2002). Extrapolating this method to the entire zebrafish genome (~40,000 genes) would take approximately 500 million sequencing reactions. A more efficient method would be to create a mutant sperm library from retroviral insertions. Since the retrovirus can serve as a tag for the disrupted locus many fewer sequencing reactions would be needed. The actual number of bases to be sequenced would also be smaller given the imminent completion of the zebrafish genome. Over a period of 4-5 months, three injectors could routinely generate the approximately 40,000 male founders necessary to harbor more than 1 million inserts. This would give an insert density on average of 1 every 1800 bp, essentially at least one insertion for every gene. Space requirements for housing the frozen library would be smaller than what is needed for most cDNA or genomic library arrays.

Forward genetics has been an invaluable approach in many model organisms; however, almost all of the forward and reverse genetics taking place in zebrafish are in the form of loss-of-function alleles. Forward genetic approaches based on the proposed retroviral zebrafish library would be enhanced with the addition of functional genetic elements. Retroviruses can provide additional functions aside from the obvious loss-of-function gene disruptions. For instance, in one large scale screen the predominant retroviral vector used had a gene-trapping cassette (Golling et al., 2002; Amsterdam et al., 1999). Of the founders injected with this construct, Chen et al. (2002) found there was at least one trapping event in the germ-line of each fish. While the trap vector itself did not prove to be more mutagenic than the previous non-trapping vectors (Chen et al., 2002), it did show the possibilities for other creative screens in the zebrafish that have previously been performed in *Drosophila*. Among these are enhancer trap constructs where fish could be screened for particular gene expression patterns, and promoter-containing vectors for mis-expression/over-expression screens. This latter approach has been used successfully in flies where Gal4 binding sites within a P-element drive expression of genes located downstream of the randomly located insert (Rorth et al., 1998; Hay et al., 1997). Transgenic fly lines expressing Gal4 protein in a controlled manner, for example under the control of an eye specific enhancer or tetracycline operator, would cause the gene downstream of the P-element to be mis-expressed according to the researcher's preference. A function such as this would provide a valuable resource for studying the function of genes that do not display obvious loss-of-function phenotype. It is estimated that such genes constitute more than two-thirds of genes in flies, worm, and yeast (Sulston et al., 1992; Dujon et al., 1994; Miklos and Rubin, 1996). It is likely that an even higher percentage of vertebrate genes have no obvious loss of function phenotype. These genes are often biologically important. For example, although loss of either NPY and/or AGRP function in mice display no detectable abnormalities (Qian et al., 2002; Erickson et al., 1996), NPY and AGRP have been found to play a key role in regulation of food-intake by gain-of-function studies (Levine and Morley, 1984); Clark et al., 1984; Graham et al., 1997; Ollmann et al., 1997). Furthermore, their pathways have been drug discovery targets for obesity and diabetes in several pharmaceutical and biotech companies (Halford, 2001).

It is estimated that half of the genes identified in the first draft of the human genome have no function ascribed to them (Lander et al., 2001; Venter et al, 2001). The ability to rapidly examine the biological roles of these unknown genes is the goal of many research institutions and pharmaceutical companies. Currently, the best vertebrate model organism for conducting these genetic studies is the mouse. Homologous recombination and random retroviral mutagenesis have made the mouse a viable resource for functional genomics research. However, several drawbacks inherent in the mouse's biology have stymied the development of quick, large-scale approaches towards gene and gene function identification. These include significantly large space requirements, small litter sizes, development in utero, high cost of breeding and maintenance, and vast regulatory/animal handling requirements. In zebrafish nearly the opposite is the case concerning these issues. Zebrafish have the added advantage of being transparent through most of their development, allowing easy visualization of the morphology and function of internal organs by light microscopy using a variety of techniques involving fluorescent, luminescent or colorimetric labeling. Thus, developing zebrafish as a forward genetic model would significantly enhance the understanding of vertebrate gene and protein function.

Recently an effort has been made by at least two companies to generate a zebrafish sperm library and, in fact, one loss-of-function gene has been published from this library (Nasevicius, and Ekker, 2000). Since the library was made from fish mutagenized with ENU, several thousand PCR and sequencing reactions were required to isolate the lone mutant. Using retroviral insertional mutagens would vastly improve the speed with which a zebrafish library could be generated and then used by researchers. Stored as sperm samples and/or as approximately 20,000 or fewer fish, possibly as few as 2,000 fish or fewer, this insertional library occupies little space. The sperm samples can easily be reconstituted into living fish for studies of gene and/or protein function. The fish can easily be reproduced for studies of gene and/or protein function. A large repository of cloned retroviral mutations in the zebrafish would be a valuable resource for the study of the function of a specific gene of interest, for screening the library for phenotypes relevant to disease so as to identify putative drug targets, for screening the library for fish that do not respond to significant drugs, toxins or other chemicals so as to identify the gene and protein that are the site(s) of action of such compounds, and for screening for compounds that might alter the expression or activity of known disease genes, or other genes/proteins of interest.

DNA transposons are mobile elements that can move from one position in a genome to another. Naturally, transposons play roles in evolution as a result of their movements within and between genomes. Geneticists have used transposons as tools for both gene delivery and insertional mutagenesis or gene tagging in lower animals (Shapiro, 1992) but not, until recently, in vertebrates. Transposons are relatively simple genetic systems, consisting of some genetic sequence bounded by inverted terminal repeats and a transposase enzyme that acts to cut the transposon out of one source of DNA and paste it into another DNA sequence (Plasterk, 1993). Autonomous transposons carry the transposase gene inside the transposon whereas non-autonomous transposons require another source of transposase for their mobilization.

One well known transposable element is the maize Ac/Ds element (Shure et al., 1983; Fedoroff et al., 1983; Pohhnan et al., 1984). Maize Ac/Ds elements can transpose in a wide variety of plant species (Osborne and Baker, 1995). Moreover, successful Ds transposition catalyzed by modified transposase was demonstrated in *Saccharomyces cerevisiae* (Weil and Kunze, 2000), implying that plant-specific proteins were not essential for transposition. Transposition in heterologous animal hosts has been reported for a number of other transposons e.g. mariner element from *Drosophila mauritiana* in zebrafish (Fadool et al., 1998), nematode *Caenorhabditis elegans* Tc3 element (Raz et al., 1998) in zebrafish, synthetic transposon Sleeping Beauty in mammalians and zebrafish (Horie et al, 2001; Davidson et al, 2003; Balciunas et al., 2004), Tol2 from *Oryzias latipes* in zebrafish, *Xenopus* and mouse (Kawakami et al., 2000; Kawakami et al., 2004; Kawakami and Noda 2004) etc. However, none of the known transposons has yet been demonstrated to transpose in both plants and animals.

The use of heterologous transposons has been a powerful tool for genetic research in a number of model species (Parinov et al., 1999; Spradling et al., 1995). The advantage of using heterologous elements is that there is no transposase in a new host once inserted a genomic copy of non-autonomous element is immobile but can be mobilized if transposase is delivered into the cells.

Methods for introducing DNA into a cell are known. These include, but are not limited to, DNA condensing reagents such as calcium phosphate, polyethylene glycol, and the like), lipid-containing reagents, such as liposomes, multi-lamellar vesicles, and the like, and virus-mediated strategies. These methods all have their limitations. For example, there are size constraints associated with DNA condensing reagents and virus-mediated strategies. Further, the amount of nucleic acid that can be introduced into a cell is limited in virus strategies. Not all methods facilitate integration of the delivered nucleic acid into cellular nucleic acid and while DNA condensing methods and lipid-containing reagents are relatively easy to prepare, the incorporation of nucleic acid into viral vectors can be labor intensive. Moreover, virus-mediated strategies can be cell-type or tissue-type specific and the use of virus-mediated strategies can create immunologic problems when used in vivo.

There remains a need for new methods for introducing DNA into a cell, particularly methods that promote the efficient integration of nucleic acid fragments of varying sizes into the nucleic acid of a cell, particularly the integration of DNA into the genome of a cell. There also remains a need to develop a vertebrate (e.g., a zebrafish, mouse, etc.) insertional mutation library that could be used to screen for genetic defects, to study genes of interest, to screen for drugs useful for treating or preventing a disease condition associated with a gene of interest.

SUMMARY OF THE INVENTION

The present invention is directed to the use of the modified maize Ac/Ds transposable elements in vertebrates, including fish, birds, and other animals, including mammals and humans. The transposon system of this invention has applications to many areas of biotechnology. Development of transposable elements for vectors in animals permits the following: 1) efficient insertion of genetic material into animal chromosomes using the methods given in this application; 2) identification, isolation, and characterization of genes involved with growth and development through the use of transposons as insertional mutagens; 3) identification, isolation and characterization of transcriptional regulatory sequences controlling growth and development; 4) use of marker constructs for quantitative trait loci (QTL) analysis; 5) identification of genetic loci of economically important traits, besides those for growth and development, i.e., disease resistance; and 6) nonviral vectors for gene therapy.

Thus, in a first aspect, the present invention provides modified Ac and Ds transposable elements for transposition in vertebrates. In one embodiment, a modified Ds element contains a polynucleotide of interest and can be used to prepare transgenic vertebrates having the polynucleotide of interest stably integrated in its genome. In a second embodiment, a modified Ds element can be used to prepare insertional mutations in vertebrates. In one aspect, the modified Ds element (also known as a Ds construct) comprises the polynucleotide of interest positioned between the 5'- and 3'-ends of the Ds element.

In a second aspect, the present invention provides transgenic vertebrates that contain either a modified Ac transposase or a modified Ds element stably integrated in their genome.

In a third aspect, the present invention provides methods for transposition in vertebrates using modified maize Ac/Ds transposable elements. In one embodiment, the modified Ds element or a vector containing the modified Ds element is introduced into a vertebrate. In one facet of this embodiment, the modified Ds element or a vector containing the modified Ds element is introduced into a vertebrate along with the RNA for the modified Ac transposase. In a second facet, the modified Ds element or a vector containing the modified Ds element is introduced into a transgenic vertebrate containing a modified Ac transposase gene as described herein stably incorporated into its genome. In a third facet, the modified Ds element or a vector containing the modified Ds element is introduced into a vertebrate along with the modified Ac transposase protein. In a fourth facet, the modified Ds element or a vector containing the modified Ds element is introduced into a vertebrate along with a vector containing a modified transposase gene. In each instance, the modified Ac transposase protein drives transposition of the modified Ds element in the vertebrate.

In a second embodiment of this third aspect, the modified Ds element is stably incorporated into the vertebrate genome to make a transgenic vertebrate. Transgenic vertebrates are prepared as described herein using the modified Ds elements described herein. In one facet of this embodiment, the RNA for the modified Ac transposase is introduced into the transgenic vertebrate containing the modified Ds element. In a second facet, a transgenic vertebrate containing a coding sequence for the modified Ac transposase stably incorporated in its genome is crossed with a transgenic vertebrate containing the modified Ds element. In a third facet, the modified Ac transposase protein is introduced into the transgenic vertebrate containing the modified Ds element. In a fourth facet, a vector containing a modified transposase gene is introduced into the transgenic vertebrate containing the modified Ds element. In each instance, the modified Ac transposase protein drives transposition of the modified Ds element in the vertebrate.

In a fourth aspect, the present invention provides insertional mutations in genes of the target vertebrate to provide an indexed library of genetically altered cells and animals. The present invention also provides methods of organizing the cells and animals into an easily manipulated and characterized library. In one embodiment, the genetically altered cells are a vertebrate, such as zebrafish, that are produced by treating vertebrate embryos, growing the embryos to adults and collecting the adult vertebrates. The adult vertebrates containing insertional mutations are termed founder vertebrates. In a second embodiment, the genetically altered cells are vertebrate sperm cells that are produced by treating vertebrate embryos, growing the embryos to adults and collecting sperm from adult males. Male vertebrate containing insertional mutations are also termed founder males. In a third embodiment, the original sperm from a founder male is thawed and then used for in vitro fertilization on eggs from wild type females to generate vertebrates that harbor the desired inserts. Secondary sperm samples are collected from all of the newly created males once they have reached adulthood. Using these methods the library allows for the completion of numerous genetic screens. The library comprises a set in which each member of the set possesses at least one mutation in at least one gene, and the set collectively comprises at least 15% of the genes In a fifth aspect, the present invention provides for the characterization of the inserts, e.g. by sequencing of the DNA flanking the inserts.

In a sixth aspect, the present invention provides a sequence database. The sequence database subsequently serves as an index for the library. In essence, every sperm cell line and/or founder vertebrates or offspring thereof in the library is individually catalogued using the sequence information. The resulting sequence is specific for the insertional mutation. From this database, a gene of interest can be identified. Once identified, the corresponding mutant sperm cell or fish may be withdrawn from the library based on cross reference to the sequence data.

In a seventh aspect, the present invention provides methods for rapidly identifying the function of genes. Vertebrates containing mutations of genes of interest, generated as described above, may be examined for specific phenotypes, much as knockout mice are studied to determine the same. As used herein, "phenotype" denotes a definable detectable heritable trait of a cell or organism that is caused by the presence and action of at least one gene or mutant gene.

In an eighth aspect, the present invention provides methods for carrying out genetic screens. As a first step in the methods, vertebrates (or vertebrates encompassing the library), or their offspring, may be used, or alternatively, sperm is thawed and then used for in vitro fertilization on eggs from wild type females to generate vertebrates that harbor the desired inserts. Diploid vertebrates may be screened from offspring of the injected females with the mutations in either the homozygous or heterozygous state, or screening may be performed in haploid embryos, known to survive and develop for three days post fertilization. Vertebrates homozygous for the mutation may be created by conventional breeding methods, creation of haploid embryos, or creation of gynogenetic diploid embryos. These methods are all well described in the prior art (for example, see Westerfield (2000) with respect to zebrafish). The vertebrates harboring the desired inserts, prepared using any of the methods described above, are used to study gene function by studying the effects of the insertional mutation in vivo. In this manner, phenotypes can be associated with the insertional mutation and the sequence data, thus allowing the identification, for example, of novel collections of putative drug targets. The sequence data also identifies the gene of interest and is used to search for homologs or orthologs in other organisms, including humans.

In a ninth aspect, the present invention provides methods for screening candidate compounds. Vertebrates that harbor a desired insert, i.e., vertebrates that have a desired mutation, are generated as described above. These transgenic vertebrates can be exposed to compounds to assess the effect of the compound on a phenotype or assay outcome of interest. For example, test compounds can be administered to transgenic vertebrates harboring the desired insert or representing all the inserts. By screening and subsequently identifying vertebrates that, by virtue of a specific mutation or mutation(s), no longer respond to a compound, one will have identified a gene encoding the protein required for the action of said compound. Test compounds may act as either inhibitors or activators of a protein encoded by the gene of interest. In this manner, compounds which are useful as drugs for treating or preventing disease conditions associated with the gene of interest are identified.

In a tenth aspect, the present invention provides the use of modified maize Ac/Ds transposable elements for gene therapy in vertebrates.

BRIEF DESCRIPTION OF THE FIGURES

FIG. 1A shows a Ds donor construct carrying 3.1 kb reporter fragment (EGFP gene under the zebrafish keratin 8 promoter), inserted between 5'- and 3'-Ds cis-sequences (250 bp and 370 bp correspondingly). Black arrowheads indicate the primers for excision PCR, gray arrowheads—specific primers for TAIL-PCR. FIG. 1B shows a TPase construct containing SP6 promoter for in vitro transcription, coding sequence for a truncated Ac transposase (TPase$_{103-807}$) fused to a synthetic nuclear localization signal. Dashed lines represent 5'- and 3'-UTRs of *Xenopus* β-globin gene. FIG. 1C shows the N-terminal amino acid sequences of the NLS-, NLS$^{K5E}$ and NoNLS-TPase. NLS signals are shown in bold and highlighted. The sequence for NLS is SEQ ID NO:2. The full amino acid sequence shown for NLS is shown by amino acid residues 1-15 of SEQ ID NO:20. The sequence for NLS$^{K5E}$ is SEQ ID NO:9. The full amino acid sequence shown for NLS$^{K5E}$ is shown by amino acid residues 1-15 of SEQ ID NO:44. The sequence for NoNLS is SEQ ID NO:31, and represents the first four amino acid residues of TPase$_{103-807}$, e.g., amino acid residues 12-15 of SEQ ID NO:20.

FIGS. 2A-2C show the TPase-specific excision and insertion of Ds element. FIG. 2A shows a Ds excision assay. Zebrafish embryos were injected with Ds construct and NoNLS-, NLS$^{K5E}$ and NLS-TPase RNA (lanes 2, 3 and 4 correspondingly) and Ds construct only (lane 1). DNA was isolated from injected embryos at 10 hours post injection and subjected to PCR using primers flanking the Ds donor site. (M) 1 kb DNA Ladder (NEB). FIG. 2B shows predominant excision footprints from two different donor vectors. Missing and changed nucleotides of the flanking donor vector are in bold or underlined respectively. Lower case letters indicates the borders of the Ds sequence. For before excision of Donor 1, the nucleotide sequence is the sequence shown in SEQ ID NO:1 from nucleotide 29 to 3917, inclusive. For after excision for Donor 1, the top line sequence is the sequence shown in SEQ ID NO:3 and the bottom line sequence is the sequence shown in SEQ ID NO:4. For before excision of Donor 2, the nucleotide sequence 5' of Ds is SEQ ID NO:68, and the nucleotide sequence 3' of Ds is SEQ ID NO:69. The "Ds" sequence is the sequence shown in SEQ ID NO:1 from nucleotide 54 to nucleotide 3892, inclusive. For after excision for Donor 2, the top line sequence is the sequence shown in SEQ ID NO:5 and the bottom line sequence is the sequence shown in SEQ ID NO:6. FIG. 2C shows representative examples of sequences flanking the Ds insertion sites from two different transgenic F$_1$ fish, demonstrating specific transposition mechanism. Ds end sequences are shown in lower case, flanking sequences—in upper case. Classic 8 bp direct target duplication is in bold and underlined. The sequence 5' of Ds in the top line is the sequence shown in SEQ ID NO:32 and the sequence 3' of Ds in the top line is the sequence shown in SEQ ID NO:33. The sequence 5' of Ds in the bottom line is the sequence shown in SEQ ID NO:34 and the sequence 3' of Ds in the bottom line is the sequence shown in SEQ ID NO:35. The "Ds" sequence is the sequence shown in SEQ ID NO:1 from nucleotide 54 to 3892, inclusive.

FIGS. 3A-3C show subcellular localization of the GFP-tagged versions of NoNLS-TPase, NLS$^{K5E}$-TPase and NLS-TPase zebrafish epithelial cells. Photographs were overexposed to highlight the cellular outline. FIGS. 3D-3F show intracellular localization of NoNLS-, NLS$^{K5E}$ and NLS-EGFP fusion proteins in zebrafish epithelial cells.

FIGS. 6A-6C show the results of the analysis of Ds in three examples of transposed HEK293 cells. The "Ds" sequence shown in FIG. 6B is the sequence shown in SEQ ID NO:70 from nucleotide 17 to nucleotide 4819, inclusive. The Ds (lower case letters) in these three examples is flanked by human DNA (upper case letters) (not the vector DNA of the donor) starting from the first nucleotide immediately adjacent to the Ds end sequence. This demonstrates that Ds integrated into human genome via transposase-mediated mechanism. In case of DNA 2, the insertion site is surrounded by classic 8 bp direct repeat that is often created when hAT transposons integrate into new locations.

DETAILED DESCRIPTION OF THE INVENTION

Figure 1:
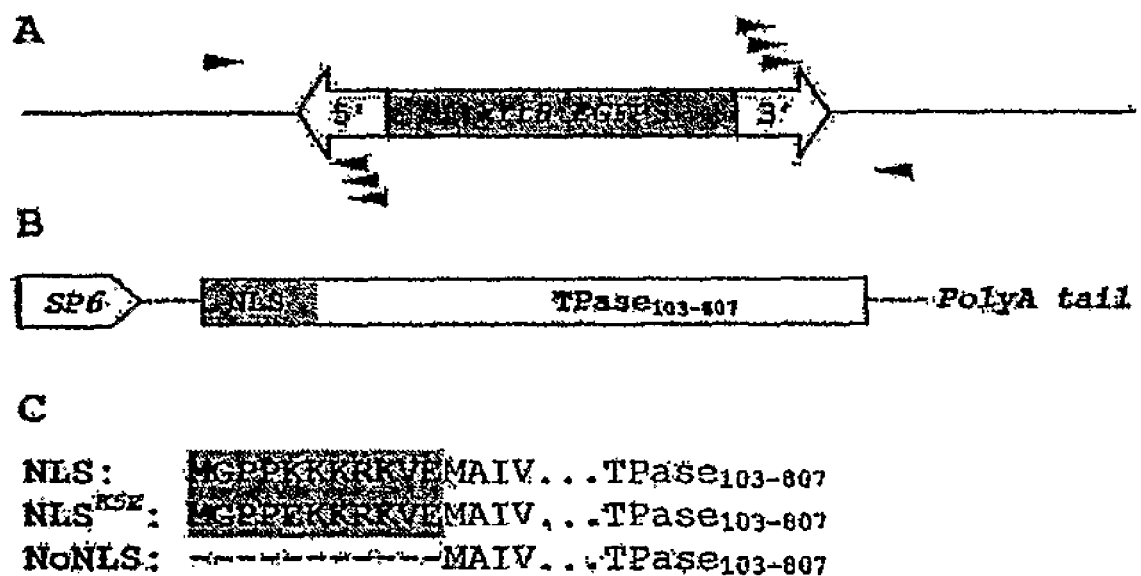
FIGS. 1A-1C show constructs made in accordance with the present invention.

The present invention describes the use of the modified maize Ac/Ds transposable elements in vertebrates, including fish, birds, and other animals including mammals. As used herein, fish refers to any member of the classes collectively referred to as Pisces. It is preferred that fish belonging to species and varieties of fish of commercial or scientific interest be used. Such fish include, but are not limited to, salmon, trout, tuna, halibut, catfish, zebrafish, medaka, carp, tilapia, goldfish, and loach. Mammals include, but are not limited to rodents, such as rats and mice, ungulates, such as cows, goats, sheep or pigs, and primates, such as monkeys, apes and humans.

The use of the modified maize Ac/Ds transposable elements in accordance with the present invention has a significant advantage for the production of stable genomic integration, i.e., eliminating the risk of re-transposition or recombination due to transposase activity produced by the host. For example, insertions of the Tol2 element originally extracted from medaka fish will be unstable in the same fish because of the host transposase (Koga et al.). Maize Ac/Ds elements have no significantly similar homologs in vertebrates.

In the description which follows, the aspects of the invention are described with reference to zebrafish for convenience only. It is understood that other fish and other animals can be used in place of zebrafish. As demonstrated in the Examples, the present invention is applicable for all vertebrates ranging from fish to humans. Thus, the modified maize Ac/Ds transposable element of the present invention can be used to introduce DNA into both pluripotent (i.e., a cell whose descendants can differentiate into several restricted cell types, such as hematopoietic stem cells or other stem cells) and totipotent cells (i.e., a cell whose descendants can become any cell type in an organism, e.g., embryonic stem cells). Suitable cells include oocytes, eggs, and one or more cells of an embryo are also considered in this invention. For gene transfer, the modified maize Ac/Ds transposable element of the present invention can be used to introduce DNA into mature cells from a variety of organs or tissues. Suitable cells include, but are not limited to, lymphocytes, hepatocytes, neural cells, muscle cells, a variety of blood cells, and a variety of cells of an organism.

The most preferred fish for use with the present invention is zebrafish, *Danio rerio*. Zebrafish are an increasingly popular experimental animal since they have many of the advantages of popular invertebrate experimental organisms, and include the additional advantage that they are vertebrates. Another significant advantage of zebrafish is that, like *Caenorhabditis*, they are largely transparent (Kimmel, 1989). General zebrafish care and maintenance are described by Streisinger (1984) and Westerfield (2000).

In accordance with the present invention, Ds transposition in fish is driven by a modified Ac transposase. It has been demonstrated earlier that a truncated form of Ac transposase lacking 102 N-terminal amino acids (TPase$_{103-807}$) (SEQ ID NOs:7 and 8) is highly active (Houba-Herin et al., 1990). In one embodiment of the present invention, this modified Ac transposase is further modified to contain a synthetic nuclear localization signal (NLS). The synthetic NLS is added to the N-terminus of TPase$_{103-807}$. The synthetic NLS is added in order to localize the transposition reaction to the nucleus. In one embodiment, the synthetic NLS is analogous to that of the SV40 large T antigen. In a preferred embodiment, this synthetic NLS has the amino acid sequence MGPPKKKRKVE (SEQ ID NO:2). Other synthetic NLSs can be used in place of the synthetic NLS analogous to the SV40 antigen. In one embodiment, the synthetic NLS is a modified NLS. One embodiment of a modified NLS is NLS$^{K5E}$ that has the amino acid sequence MGPPEKKRKVE (SEQ ID NO:9). A nucleotide sequence coding for the synthetic NLS is added to the 5' end of the coding sequence for TPase$_{103-807}$ to produce a coding sequence for the modified Ac transposase. One embodiment of a coding sequence for NLS-TPase$_{103-807}$ is set forth in SEQ ID NO:10. One embodiment of a coding sequence for NLS$^{K5E}$-TPase$_{103-807}$ is set forth in SEQ ID NO:36.

In a further embodiment of the present invention, the modified Ac transposase utilized in the invention may have a nucleotide sequence that has at least about 60%, preferably at least about 70%, more preferably at least about 80%, and most preferably at least about 90% identity to the nucleotide sequence of the modified Ac transposase discussed herein when optimally aligned (with appropriate nucleotide insertions or deletions). A skilled artisan recognizes that the nucleotide sequence can be modified on the basis of the genetic code to produce a different nucleotide sequences that encode the identical protein. Alternatively, the modified Ac transposase utilized in the invention may have an amino acid sequence that is at least about 75%, preferably at least about 85%, more preferably at least about 90% and most preferably at least about 95% identity to the amino acid sequence disclosed herein for the modified Ac transposase.

Identity means the degree of sequence relatedness between two polypeptides or two polynucleotides sequences as determined by the identity of the match between two strings of such sequences. Identity can be readily calculated. While there exist a number of methods to measure identity between two polynucleotide or polypeptide sequences, the term "identity" is well known to skilled artisans (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). Methods commonly employed to determine identity between two sequences include, but are not limited to those disclosed in *Guide to Huge Computers*, Martin J. Bishop, ed., Academic Press, San Diego, 1994, and Carillo, H., and Lipman, D., *SIAM J Applied Math.* 48:1073 (1988). Preferred methods to determine identity are designed to give the largest match between the two sequences tested. Such methods are codified in computer programs. Preferred computer program methods to determine identity between two sequences include, but are not limited to, GCG (Genetics Computer Group, Madison Wis.) program package (Devereux, J., et al., *Nucleic Acids Research* 12:387 (1984)), BLASTP, BLASTN, FASTA (Altschul et al. (1990); Altschul et al. (1997)). The well-known Smith Waterman algorithm may also be used to determine identity.

As an illustration, by a polynucleotide having a nucleotide sequence having at least, for example, 95% "identity" to a reference nucleotide sequence of is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

Additionally, the modified Ac transposase gene may include nucleotide sequences having substantial similarity to the modified Ac transposase nucleotide sequence discussed herein. By "substantial similarity", it is meant herein that the nucleotide sequence is sufficiently similar to a reference nucleotide sequence that it will hybridize therewith under moderately stringent conditions. This method of determining similarity is well known in the art to which the invention pertains. Briefly, moderately stringent conditions are defined in Sambrook et al. (*Molecular Cloning: A Laboratory Manual*, $2^{nd}$ Ed., Vol. 1, pp. 101-104, Cold Spring Harbor Laboratory Press (1989)) as including the use of a prewashing solution of 5×SSC (a sodium chloride/sodium citrate solution), 0.5% sodium dodecyl sulfate (SDS), 1.0 mM ethylene diaminetetracetic acid (EDTA) (pH 8.0) and hybridization and washing conditions of 55° C., 5×SSC.

The modified Ac transposase may be either synthesized in vitro or isolated from a biological source. Such methods of synthesis and isolation are well known to the skilled artisan.

The modified Ac transposase is introduced into fish. In one embodiment, a modified Ac transposase protein is introduced into fish. The protein is introduced into fish using conventional techniques, such as microinjection.

In a second embodiment, RNA for the modified Ac transposase is introduced into fish. In accordance with this embodiment, the modified Ac transposase transcript may be synthesized in vitro or isolated from a biological source. In one aspect, a nucleic acid construct is prepared which contains an RNA polymerase promoter and the coding sequence for the modified Ac transposase. The RNA polymerase promoter is preferably the SP6 promoter. However, other RNA polymerase promoters can be used, including the T7 promoter. The nucleic acid construct further comprises 5'- and 3'-UTRs and a polyA tail. Any 5'- and 3'-UTRs may be used, although it is preferred to use the 5'- and 3'-UTRs and polyA tail of the *Xenopus* β-globin gene. Alternatively, 5'- and 3'-UTRs native to fish may be used in place of the 5'- and 3'-UTRs of the *Xenopus* β-globin gene. Similarly, a polyA tail native to fish may be used in place of the polyA tail of the *Xenopus* β-globin gene. One embodiment of such a nucleic acid construct is set forth in SEQ ID NO:11. A second embodiment of such a nucleic acid is set forth in SEQ ID NO:37.

In a third embodiment, the modified Ac transposase gene is stably incorporated into the fish genome to make a transgenic fish. As used herein, transgenic fish refers to fish, or progeny of a fish, into which an exogenous construct has been introduced. A fish into which a construct has been introduced includes fish which have developed from embryonic cells into which the construct has been introduced. As used herein, an exogenous construct is a nucleic acid that is artificially introduced, or was originally artificially introduced, into an animal. The term artificial introduction is intended to exclude introduction of a construct through normal reproduction or genetic crosses. That is, the original introduction of a gene or trait into a line or strain of animal by cross breeding is intended to be excluded. However, fish produced by transfer, through normal breeding, of an exogenous construct (that is, a construct that was originally artificially introduced) from a fish containing the construct are considered to contain an exogenous construct. Such fish are progeny of fish into which the exogenous construct has been introduced. As used herein, progeny of a fish are any fish which are descended from the fish by sexual reproduction or cloning, and from which genetic material has been inherited. In this context, cloning refers to production of a genetically identical fish from DNA, a cell, or cells of the fish. The fish from which another fish is descended is referred to as a progenitor or founder fish. As used herein, development of a fish from a cell or cells (embryonic cells, for example), or development of a cell or cells into a fish, refers to the developmental process by which fertilized egg cells or embryonic cells (and their progeny) grow, divide, and differentiate to form an adult fish.

A transgene construct containing a coding sequence for the modified Ac transposase is used to prepare transgenic fish. Transgene constructs are the genetic material that is introduced into fish to produce a transgenic fish. Such constructs are artificially introduced into fish. The manner of introduction, and, often, the structure of a transgene construct, render such a transgene construct an exogenous construct. Although a transgene construct can be made up of any nucleic acid sequences, for use in the disclosed transgenic fish it is preferred that the transgene constructs combine expression sequences operably linked to a sequence encoding an expression product. The transgenic construct also preferably includes other components that aid expression, stability or integration of the construct into the genome of a fish. As used herein, components of a transgene construct referred to as being operably linked or operatively linked refer to components being so connected as to allow them to function together for their intended purpose. For example, a promoter and a coding region are operably linked if the promoter can function to result in transcription of the coding region.

In a one aspect, the transgene construct is the RNA polymerase promoter construct described above. In a second aspect, a transgene construct containing a coding sequence for the modified Ac transposase is prepared to include expression sequences. The expression sequences are used to mediate expression of an expression product encoded by the construct. As used herein, expression sequences include promoters, upstream elements, enhancers, and response elements. It is preferred that the expression sequences used in the disclosed constructs be homologous expression sequences. As used herein, in reference to components of transgene constructs used in the disclosed transgenic fish, homologous indicates that the component is native to or derived from the species or type of fish involved. Conversely, heterologous indicates that the component is neither native to nor derived from the species or type of fish involved.

As used herein, expression sequences are divided into two main classes, promoters and enhancers. A promoter is generally a sequence or sequences of DNA that function when in a relatively fixed location in regard to the transcription start site. A promoter contains core elements required for basic interaction of RNA polymerase and transcription factors, and may contain upstream elements and response elements. Enhancer generally refers to a sequence of DNA that functions at no fixed distance from the transcription start site and can be in either orientation. Enhancers function to increase transcription from nearby promoters. Enhancers also often contain response elements that mediate the regulation of transcription. Promoters can also contain response elements that mediate the regulation of transcription.

For expression of encoded peptides or proteins, a transgene construct also needs sequences that, when transcribed into RNA, mediate translation of the encoded expression products. Such sequences are generally found in the 5' untranslated region of transcribed RNA. This region corresponds to the region on the construct between the transcription initiation site and the translation initiation site (that is, the initiation codon). The 5' untranslated region of a construct can be derived from the 5' untranslated region normally associated with the promoter used in the construct, the 5' untranslated region normally associated with the sequence encoding the expression product, the 5' untranslated region of a gene unrelated to the promoter or sequence encoding the expression product, or a hybrid of these 5' untranslated regions. Preferably, the 5' untranslated region is homologous to the fish into which the construct is to be introduced. Preferred 5' untranslated regions are those normally associated with the promoter used.

Transgene constructs for use in the disclosed transgenic fish may encode a reporter protein (for detection and quantitation of expression). As used herein, a reporter protein is any protein that can be specifically detected when expressed. Reporter proteins are useful for detecting or quantitating expression from expression sequences. For example, operatively linking nucleotide sequence encoding a reporter protein to a tissue specific expression sequences allows one to carefully study lineage development. In such studies, the reporter protein serves as a marker for monitoring developmental processes, such as cell migration. Many reporter proteins are known and have been used for similar purposes in other organisms. These include enzymes, such as β-galactosidase, luciferase, and alkaline phosphatase, that can produce specific detectable products, and proteins that can be directly detected. Virtually any protein can be directly detected by using, for example, specific antibodies to the protein.

The use of reporter proteins that are directly detectable without requiring the addition of exogenous factors are preferred for detecting or assessing gene expression during zebrafish embryonic development. A transgenic zebrafish embryo, carrying a construct encoding a reporter protein and a tissue-specific expression sequences, can provide a rapid real time in vivo system for analyzing spatial and temporal expression patterns of developmentally regulated genes.

The disclosed transgene constructs preferably include other sequences which improve expression from, or stability of, the construct. For example, including a polyadenylation signal on the constructs encoding a protein ensures that transcripts from the transgene is processed and transported as mRNA. The identification and use of polyadenylation signals in expression constructs is well established. It is preferred that homologous polyadenylation signals be used in the transgene constructs.

In accordance with the above principles, the coding sequence for the modified Ac transposase is operably linked to a promoter. Any promoter active in the fish species may be used. Since most mammalian promoters are found not to work well in fish, then the genomic regulatory sequences of the zebrafish, fugu or other fish species often must be specifically cloned upstream, within, and downstream of the coding sequence of interest, which may be accomplished by procedures routine to those skilled in the art.

As defined herein, a nucleotide sequence is "operably linked" to another nucleotide sequence when it is placed in a functional relationship with another nucleotide sequence. For example, if a coding sequence is operably linked to a promoter sequence, this generally means that the promoter may promote transcription of the coding sequence. Operably linked means that the DNA sequences being linked are typically contiguous and, where necessary join two protein coding regions, contiguous and in reading frame. Since enhancers may function when separated from the promoter by several kilobases and intron sequences may be of variable lengths, some nucleotide sequences may be operably linked but not contiguous.

The construct further preferably comprises a marker or a reporter gene. In a preferred embodiment, the oncogene is preceded by a reporter gene, such as a fluorescent protein gene (e.g., EGFP, GFP, RFP, BFP, YFP, or dsRED2) or a luciferase protein gene. In a most preferred embodiment, the marker is enhanced green fluorescent protein (EGFP) (Zhang et al., 1996). EGFP is preferred because of the high sensitivity of the reporter protein. In the preferred embodiment, a fusion of the marker and the oncogene is prepared such that the fused gene is under control of the promoter.

Although, the use of specific markers has been disclosed and discussed herein, the present invention is in no way limited to the specifically disclosed markers. Many additional reporter proteins are known and have been used for similar purposes. These include enzymes, such as β-galactosidase, luciferase, chloramphenicol acyltransferase, β-glucuronidase and alkaline phosphatase, that can produce specific detectable products, and proteins that can be directly detected. Virtually any protein can be directly detected by using, for example, specific antibodies to the protein. Any reporter which can be readily detected may be used in place of the EGFP. Additional markers (and associated antibiotics) that are suitable for either positive or negative selection of eukaryotic cells are disclosed, inter alia, in Sambrook and Russell (2001), *Molecular Cloning*, 3$^{rd}$ Ed., Cold Spring Harbor Laboratory Press, Cold Spring Harbor, N.Y., and Ausubel et al. (1992), *Current Protocols in Molecular Biology*, John Wiley & Sons, including periodic updates. Any of the disclosed markers, as well as others known in the art, may be used to practice the present invention.

Transgenic fish are prepared using the constructs described herein. In one embodiment, a method includes introducing the nucleic acid, i.e., construct or vector described herein, into a fertilized fish egg (i.e., including a fish embryo) or an unfertilized fish egg nucleic acid. When a fertilized fish egg is used, the method includes developing the fish embryo into a transgenic fish. When the nucleic acid is introduced into a non-fertilized egg, the method includes fertilizing the egg and developing the fish embryo into a transgenic fish. The nucleic acid may be introduced into the egg by a variety of methods known to the art, including mechanical methods, chemical methods, lipophilic methods, retroviral infection methods, and electroporation. Exemplary mechanical methods include, for example, microinjection. Exemplary chemical methods include, for example, use of calcium phosphate or DEAE-Dextran. Exemplary lipophilic methods include use of liposomes and other cationic agents for lipid-mediated transfection. Such methods are generally well known to the art and many of such methods are described in, for example, *Gene Transfer Methods: Introducing DNA into Living Cells and Organisms*, (P. A. Norton and L. F. Steel, eds., Biotechniques Press, 2000); and *Current Protocols in Molecular Biology* (Ausubel et al., eds., John Wiley & Sons). Microinjection techniques involving fish are further more fully described in, for example, Chen and Powers (1990) and Fletcher and Davis (1991). Electroporation techniques involving fish are further more fully described in, for example, Powers et al. (1992) and Lu et al. (1992). Techniques for introducing DNA into fish eggs or embryos by infection with retroviral vectors, such as pantropic retroviral vectors, are further described in, for example, Burns et al. (1993).

The vector or other nucleic acid comprising the transgene may be introduced into an unfertilized egg or a fertilized egg at a desired stage of development. Multiple vectors, each encoding different transgenes as described herein may be used. When using a fertilized egg, or embryo, it is preferred to introduce the nucleic acid into the embryo (i.e., at the one-cell stage of development). However, the nucleic acid may also be administered at later stages of development, including the two-cell stage, four-cell stage, etc. Therefore, the nucleic acid may be introduced into the morula, blastula, etc. At least one isolated nucleic acid molecule incorporating the above-described transgenic construct is introduced into the zygote. Additionally, when the nucleic acid is introduced into an egg at later stages of development, at least one isolated nucleic acid molecule incorporating the above-described transgenic construct is introduced into at least one cell of the, for example, morula, blastula, etc.

Fish eggs may be obtained from the appropriate fish by standard methods. Many of the fish may be purchased commercially from, for example, pet stores. Fertilized eggs may be obtained by methods known to the art. For example, a desired number of appropriately aged fish, such as about three to about twelve month old fish, with a desired ratio of females to males (such as about 2:1) may be placed in an appropriately sized container, such as a tank. Eggs may be collected by, for example, placing the fish in a nuptial chamber in the tank for an appropriate time after mating, such as about 10 to 60 minutes. Such methods are described in, for example, Culp et al. (1991). Alternatively, fish eggs may be artificially fertilized by methods known to the skilled artisan. One skilled in the art is familiar with other methods of obtaining such fertilized fish eggs.

After introducing the nucleic acid construct into the fish egg or embryo, the fish egg or embryo is provided with an environment conducive to development into an adult fish. Such an environment may include, for example, growth at 28.5° C. in E3 egg water for 15 days followed by introduction into circulating system water by day 16 (Westerfield, 2000).

Fish harboring a transgene can be identified by any suitable means. The use of reporter proteins that, like fluorescent proteins (such as EGFP, GFP, RFP, BFP, YFP, or dsRED2), are directly detectable without requiring the addition of exogenous factors are preferred for detecting or assessing gene expression during zebrafish embryonic development. A transgenic zebrafish embryo, carrying a construct encoding a reporter protein can provide a rapid real time in vivo system for analyzing spatial and temporal expression patterns of developmentally regulated genes. Alternatively, the genome of potential transgenic fish can be probed for the presence of construct sequences. To identify transgenic fish actually expressing the transgene, the presence of an expression product can be assayed. Several techniques for such identification are known and used for transgenic animals and most can be applied to transgenic fish. Probing of potential or actual transgenic fish for nucleic acid sequences present in or characteristic of a transgene construct is preferably accomplished by Southern or Northern blotting. Also preferred is detection using polymerase chain reaction (PCR) or other sequence-specific nucleic acid amplification techniques. Preferred techniques for identifying transgenic zebrafish are described in the examples.

The transgene may be included in a vector for delivery. A vector, as used herein and as known in the art, refers to a nucleic acid construct that includes genetic material designed to direct transformation (i.e., the process whereby genetic material of an individual cell is altered by incorporation of exogenous DNA into its genome) of a targeted cell. A vector may contain multiple genetic elements positionally and sequentially oriented, i.e., operably linked with other necessary or desired elements such that the nucleic acid in a cassette can be transcribed and, if desired, translated in the microinjected, single-cell fertilized embryo.

Recombinant expression vectors may be constructed by incorporating the above-recited nucleotide sequences within a vector according to methods well known to the skilled artisan and as described, for example, in references cited herein. A wide variety of vectors are known that have use in the invention. Suitable vectors include plasmid vectors, viral vectors, including retrovirus vectors (e.g., see Miller et al., 1993), adenovirus vectors (e.g., see Erzurum et al., 1993; Zabner et al., 1994; Davidson et al., 1993) adeno-associated virus vectors (e.g., see Flotte et al., 1993), herpesvirus vectors (e.g., see Anderson et al., 1993), and lentivirus vectors (e.g., see Lever, 2000).

The disclosed constructs and methods can be used with any type of fish. As used herein, fish refers to any member of the classes collectively referred to as Pisces. It is preferred that fish belonging to species and varieties of fish of commercial or scientific interest be used. Such fish include, but are not limited to, salmon, trout, tuna, halibut, catfish, zebrafish, medaka, carp, tilapia, goldfish, and loach.

The most preferred fish for use with the disclosed constructs and methods is zebrafish, *Danio rerio*. Zebrafish are an increasingly popular experimental animal since they have many of the advantages of popular invertebrate experimental organisms, and include the additional advantage that they are vertebrates. Another significant advantage of zebrafish is that, like *Caenorhabditis*, they are largely transparent (Kimmel, 1989). General zebrafish care and maintenance are described by Streisinger (1984) and Westerfield (2000).

Zebrafish embryos are easily accessible and nearly transparent. Given these characteristics, a transgenic zebrafish embryo, carrying a construct encoding a reporter protein and tissue-specific expression sequences, can provide a rapid real time in vivo system for analyzing spatial and temporal expression patterns of developmentally regulated genes. In addition, embryonic development of the zebrafish is extremely rapid. In 24 hours an embryo develops rudiments of all the major organs, including a functional heart and circulating blood cells (Kimmel, 1989). Other fish with some or all of the same desirable characteristics are also preferred.

Identifying the pattern of expression in the disclosed transgenic fish can be accomplished by measuring or identifying expression of the transgene in different tissues (tissue-specific expression), at different times during development (developmentally regulated expression or developmental stage-specific expression), in different cell lineages (cell lineage-specific expression). These assessments can also be combined by, for example, measuring expression (and observing changes, if any) in a cell lineage during development. The nature of the expression product to be detected can have an effect on the suitability of some of these analyses. On one level, different tissues of a fish can be dissected and expression can be assayed in the separate tissue samples. Such an assessment can be performed when using almost any expression product. This technique is commonly used in transgenic animals and is useful for assessing tissue-specific expression. Expression can be determined biochemically, enzymatically, phenotypicallly or in a model fish.

This technique can also be used to assess expression during the course of development by assaying for the expression product at different developmental stages. Where detection of the expression product requires fixing of the sample or other treatments that destroy or kill the developing embryo or fish, multiple embryos must be used. This is only practical where the expression pattern in different embryos is expected to be the same or similar. This is the case when using the disclosed transgenic fish having stable and predictable expression. A more preferred way of assessing the pattern of expression of a transgene during development is to use an expression product that can be detected in living embryos and animals.

In zebrafish, the nervous system and other organ rudiments appear within 24 hours of fertilization. Since the nearly transparent zebrafish embryo develops outside its mother, the origin and migration of lineage progenitor cells can be monitored by following expression of an expression product in transgenic fish. In addition, the regulation of a specific gene can be studied in these fish.

In a fourth embodiment, a vector containing a gene encoding a modified Ac transposase is introduced into fish. In one aspect, the gene encoding a modified Ac transposase is a transgene construct such as described above. Any suitable vector, e.g., a plasmid vector, a viral vector, and the like can be used to introduce the modified Ac transposase gene into fish using conventional techniques, such as by microinjection.

Ds transposition in fish is accomplished by introducing a modified Ds element carrying DNA (also referred to as a polynucleotide) of interest and the modified Ac transposase into fish. In one embodiment, the modified Ds element or a vector containing the modified Ds element is introduced into fish. In one aspect of this embodiment, the modified Ds element or a vector containing the modified Ds element is introduced into fish along with the RNA for the modified Ac transposase. In a second aspect, the modified Ds element or a vector containing the modified Ds element is introduced into a transgenic fish containing a coding sequence for a modified Ac transposase gene as described herein stably incorporated into its genome. In a third aspect, the modified Ds element or a vector containing the modified Ds element is introduced into fish along with the modified Ac transposase protein. In a fourth aspect, the modified Ds element or a vector containing the modified Ds element is introduced into fish along with a vector containing a modified transposase gene. In each instance, the modified Ac transposase protein drives transposition of the modified Ds element in fish.

In a second embodiment, the modified Ds element is stably incorporated into the fish genome to make a transgenic fish. Transgenic fish are prepared as described herein using the modified Ds elements described herein. In one aspect of this embodiment, the RNA for the modified Ac transposase is introduced into the transgenic fish containing the modified Ds element. In a second aspect, a transgenic fish containing a coding sequence for the modified Ac transposase is crossed with a transgenic fish containing the modified Ds element. In a third aspect, the modified Ac transposase protein is introduced into the transgenic fish containing the modified Ds element. In a fourth aspect, a vector containing a modified transposase gene is introduced into the transgenic fish containing the modified Ds element. In each instance, the modified Ac transposase protein drives transposition of the modified Ds element in fish.

The Ds element is modified to contain a polynucleotide of interest. The modified Ds element (also referred to as a Ds construct) comprises the polynucleotide of interest positioned between the 5'- and 3'-ends of a native Ds element. The Ds 5'- and 3'-ends contain sequences required for transposition including two short terminal inverted repeat sequences and sequences that can bind the modified Ac transposase. Following transposition, the polynucleotide that is incorporated into the fish DNA comprises both Ds 3'- and 5'-ends and the polynucleotide of interest that was placed between them. In one embodiment, the short terminal repeat sequences are: 5'-terminal repeat: TTTCATCCCTG (SEQ ID NO:12) and 3'-terminal repeat: TTTCATCCCTA (SEQ ID NO:13). In other embodiments, modifications of the 5'- and 3'-ends of the wildtype Ds element are made that are useful for transposition with the modified Ac transposase or native Ac transposase. The polynucucleotide of interest may contain another transposable element, for example, Tol2, Sleeping Beauty and the like.

In one embodiment, the Ds 5' end cis-required sequence is shown in SEQ ID NO:45. In a second embodiment, the Ds 5' end cis-required sequence is shown as nucleotides 3657-3903 of SEQ ID NO:1. In one embodiment, the Ds 3' end cis-required sequence is shown in SEQ ID NO:49. In a second embodiment, the Ds 3' end cis-required sequence is shown as nucleotides 43-412 of SEQ ID NO:1.

In a further embodiment of the present invention, the Ds 5' and 3' ends utilized in the invention may have a nucleotide sequence that has at least about 60%, preferably at least about 70%, more preferably at least about 80%, and most preferably at least about 90%, 95% or 98% identity to the nucleotide sequence of the modified Ds 5' and 3' ends discussed herein when optimally aligned (with appropriate nucleotide insertions or deletions). Additionally, the sequences of the Ds 5' and 3' ends may include nucleotide sequences having substantial similarity to the Ds 5' and 3' ends nucleotide sequences discussed herein. The Ds 5' and 3' ends are capable of being recognized by the modified Ac transposase described herein. The modified Ac transposase binds to the Ds 5' and 3' ends and catalyzes the integration of the nucleic acid located between the Ds 5' and 3' ends into the genome of the fish cell.

The Ds 5' and 3' ends may be either synthesized in vitro or isolated from a biological source. Such methods of synthesis and isolation are well known to the skilled artisan.

The polynucleotide of interest may be a marker or reporter gene, such as described herein. Alternatively, the polynucleotide of interest may be any gene or nucleic acid that is desired to be inserted into the genome of the target fish. Such polynucleotide of interest can be selected for use in promoter-trapping, enhancer-trapping, gene-trapping, activation tagging, RNA or protein expression and the like, as well known to persons skilled in the art. For example, the polynucleotide of interest may be a coding sequence operatively linked to a promoter for expression of a protein in the target transgenic fish made in accordance with the present invention, i.e., a target fish subjected to transposition of the coding sequence from the Ds construct using the modified Ac transposase.

Alternatively, the polynucleotide of interest could be a marker sequence operatively linked to a weak promoter for enhancer-trapping. Alternatively, the polynucleotide of interest gene could be a marker sequence without a promoter for identifying a previously uncharacterized promoter element (the technique referred to as promoter trapping). Alternatively, the polynucleotide of interest could be a 3-frame His-tag DNA sequence that can be used for activation tagging such as disclosed in U.S. Pat. No. 6,709,863.

A Ds construct useful for insertional mutations contains the necessary features required for making a functional transposable element, such as the 5'- and 3'-ends of the Ds element, and a selectable marker, such as those described herein. Additional functional elements are included as desired for specific mutagenic capabilities, such as inducible over-expression of downstream genes. Such additional functional elements may include a cell or tissue specific promoter, Gal4 operators, tetracycline operators, *Xenopus* basal promoter, such as the efl-α gene, a rabbit β-globin intron, MAZ transcriptional pause site, loxP homologous recombination site T7 RNA polymerase promoter, basal TATA box. The use of a cell or tissue specific promoter results in the mis-expression of genes in specific cells or tissue.

Mis-expression can be regulated through the use of a Gal4/VP16 transactivator, a Tet-on (rtTA) transactivator that would activate transcription upon doxycycline induction, or a Tet-off (tTA) transactivator whose constitutive activation could be shut off by addition of tetracycline. Yeast and bacterial derived enhancers are used not only because these modules provide versatility, but also because enhancers that can be recognized by vertebrate transcription factors may decrease the titer of the virus. However, in appropriate circumstances, vertebrate transcription factors may also be utilized. The second intron of the rabbit β-globin gene is included to enhance the expression of the downstream genes and to splice out any endogenous intron where the virus may integrate. In a preferred aspect, these gene products are expressed under different zebrafish promoters or under homologs or orthologs of these zebrafish promoters, as they may be in any of the other vectors described herein. As used herein, a "homolog" is a nucleic acid or polypeptide similar in sequence to other nucleic acids or polypeptides among a single species, and an "ortholog" is a nucleic acid or polypeptide obtained from one species that is the functional counterpart of a nucleic acid or polypeptide from a different species. One example, among many, is the zebrafish tyrosine hydroxylase promoter or its orthologs. By expressing Gal4 protein under this promoter it is possible to mis-express genes, in combination with the sperm library, only in those tyrosine hydroxylase expressing neurons, allowing the examination of tissue-specific effects in the fish while excluding other areas that may complicate phenotypic analysis.

The inclusion of a loxP site for targeted homologous recombination may be very useful in characterizing genes from the insertional library. For example, a gene that is disrupted by a transposable insert could have its expression restored by using the wild type gene flanked by loxP sites and Cre recombinase. It is also possible to examine expression patterns of the gene by inserting a loxP flanked GFP reporter. As described previously, in a preferred aspect, these gene products are expressed under different zebrafish promoters or under orthologs of these zebrafish promoters.

It may also be useful to include a transcriptional pause site and a synthetic, strong polyadenylation site in the opposite orientation of transcription. Although a spectrum of alleles varying in strength is desirable in some situations, it is desirable to construct a library with complete loss-of-function mutations. The addition of transcriptional pause sites and a polyadenylation signal should stop the transcription at the insertion site and result in truncated transcripts, even if the insertions are in introns. In this manner, all essential genes should be included in the library. As described previously, in a preferred aspect, these gene products are expressed under different zebrafish promoters or under orthologs of these zebrafish promoters.

Enhancers often determine the regulation of expression of a gene. This effect has been seen in so-called enhancer trap constructs where introduction of a construct containing a reporter gene operably linked to a promoter is expressed only when the construct inserts into the domain of an enhancer (O'Kane et al., 1987; Allen et al., 1988; Kothary et al., 1988; Gossler et al., 1989). In such cases, the expression of the construct is regulated according to the pattern of the newly associated enhancer. Thus, a Ds construct having only a minimal promoter, such as a carp β-actin promoter, and a reporter gene can be used to identify enhancers in the target fish. The Sleeping Beauty transposon has been used for exon trapping in zebrafish (Balciunas et al., 2004).

Simple microinjection of nucleic acids into fish embryos is generally ineffective in order to produce stable transgenic fish. The use of transposon vector for transgene delivery facilitates germ-line integration of the polynucleotide of interest. Moreover, unlike the unspecific integrations (simple nucleic acid microinjection) that occur at random positions within vector sequences and are usually concatemeric, transposon insertions into host DNA are usually single and have specific boundaries. It simplifies identification of their surrounding regions (using TAIL-PCR, inversed PCR, and other suitable techniques) and is optimal for stable expression of the transposon-transmitted transgenes.

The present invention can be used for insertional mutagenesis. Ds can produce somatic and heritable germ-line mutations upon insertion into the fish genome. Unlike retroviral or non-specific insertions, transposons can be remobilized if the modified Ac transposase is supplied. It can be used to produce insertions into surrounding genes or deletions. The Ds element can carry various constructs for use in RNA or protein expression, promoter-trapping, enhancer-trapping, gene-trapping or activation tagging. Such methods are well known to skilled artisans.

A Ds element can integrate into either of two types of chromatin, functional DNA sequences where it may have a deleterious effect due to insertional mutagenesis or non-functional chromatin where it may not have much of a consequence. This power of "transposon tagging" has been exploited in simpler model systems for nearly two decades (Bingham et al., 1981; Bellen et al., 1989). Transposon tagging is an old technique in which transgenic DNA is delivered to cells so that it will integrate into genes, thereby inactivating them by insertional mutagenesis. In the process, the inactivated genes are tagged by the transposable element which then can be used to recover the mutated allele. Insertion of a transposable element may disrupt the function of a gene which can lead to a characteristic phenotype. Because insertion is approximately random, the same procedures that generate insertional, loss-of-function mutants can often be used to deliver genes that will confer new phenotypes to cells. Gain-of-function mutants can be used to understand the roles that gene products play in growth and development as well as the importance of their regulation.

There are several ways of isolating the tagged gene. In all cases genomic DNA is isolated from cells from one or more tissues of the mutated animal by conventional techniques (which vary for different tissues and animals). The DNA is cleaved by a restriction endonuclease that may or may not cut in the transposon tag (more often than not it does cleave at a known site). The resulting fragments can then either be directly cloned into plasmids or phage vectors for identification using probes to the transposon DNA (for references, see Kaiser et al., 1995). Alternatively, the DNA can be PCR amplified in any of many ways; we have used the LM-PCR procedure of Izsvak and Ivics (1993) and a modification by Devon et al. (1995) and identified by its hybridization to the transposon probe. Alternative methods include inverse-PCR (e.g., Allende et al., 1996) TAIL-PCR (Liu & Whittier, 1995), etc. Alternatively, other methods of amplification can be used in place of PCT. Regardless of method for cloning, the identified clone is then sequenced. The sequences that flank the transposon (or other inserted DNA) can be identified by their non-identity to the insertional element. The sequences can be combined and then used to search the nucleic acid databases for either homology with other previously characterized gene(s), or partial homology to a gene or sequence motif that encodes some function. In some cases the gene has no homology to any known protein. It becomes a new sequence to which others will be compared. The encoded protein will be the center of further investigation of its role in causing the phenotype that induced its recovery.

The presently described invention allows for large-scale genetic analysis of the genome of zebrafish. The library is constructed by transfecting embryos by standard techniques, or preferably, by injecting embryos with the Ds elements described herein. The injected embryos also receive proper care and feeding once they have fully consumed their yolk at day 5. This approach generates enough fish to harbor, on average, more than one Ds element per gene in the zebrafish.

Characterization of the inserts, in terms of where in the genome (i.e., specific sequence) they have landed, takes place once the founder males have reached adulthood and can produce significant quantities of sperm (about 4 months). Briefly, two days before sperm collection, each injected male is mated with wild-type females. Successfully mated males are kept individually for two days in disposable 16 oz cups while the overall health of their clutch is examined. Fecund males then have their testes removed for sperm freezing and storage. DNA from the 5-day old offspring of each male is extracted and analyzed using conventional techniques, such as TAIL-PCR, inversed PCR and the like.

Completion of sequencing the DNA flanking the inserts for all the founder fish, yields a library of the inserts. These samples are easily contained in cryovials in a liquid nitrogen storage unit. For safety purposes, each sample is split for storage in multiple liquid nitrogen units. When a sample is needed for testing it is thawed and then used for in vitro fertilization on eggs from wild type females to generate fish that harbor the desired inserts. Since multiple freeze/thaw cycles can decrease the viability of the sperm sample, secondary sperm samples are generated from all of the newly created males once they have reached adulthood. The library allows for the completion of numerous genetic screens. The library comprises a set or population of zebrafish sperm in which each member of the set possesses at least one mutation in at least one gene, and the set or population of zebrafish sperm collectively comprises at least 15% of the genes, or at least 20% of the genes, or at least 25% of the genes, or at least 30% of the genes, or at least 35% of the genes, or at least 40% of the genes, or at least 45%, or at least 50%, or at least 55% of the genes, or at least 60% of the genes, or at least 65% of the genes, or at least 70%, at least 75% of the genes, or at least 80% of the genes, or at least 85% of the genes, or at least 90% of the genes, or at least 95% of the genes, or at least 98% of the genes, or at least 99% of the genes, or 100% of the genes contain a mutation.

Alternatively, a set or population of fish is generated from the founder fish or their progeny, in which the set of fish collectively comprises a substantially comprehensive library of the inserts. The fish and their progeny are easily maintained in an automated aquarium system. These fish can easily be raised, tagged for individual identification system, and stored in approximately 200 fish tanks, which is a small sized aquatic facility for a researcher. The library allows for the completion of numerous genetic screens. The library comprises a set or population of zebrafish in which each member of the set possesses at least one mutation in at least one gene, and the set or population of zebrafish collectively comprises at least 15% of the genes, or at least 20% of the genes, or at least 25% of the genes, or at least 30% of the genes, or at least 35% of the genes, or at least 40% of the genes, or at least 45%, or at least 50%, or at least 55% of the genes, or at least 60% of the genes, or at least 65% of the genes, or at least 70%, at least 75% of the genes, or at least 80% of the genes, or at least 85% of the genes, or at least 90% of the genes, or at least 95% of the genes, or at least 98% of the genes, or at least 99% of the genes, or 100% of the genes contain a mutation.

On the basis of the draft of the zebrafish genome, it should be possible to identify which gene is disrupted by sequencing less than 50 bases of DNA flanking the insert. The sequences produced during the characterization of the inserts, provide a means to identify and catalogue the genes mutated in each sperm sample or in each fish of the library. Such a database provides both an index for the presently disclosed libraries, and a resource for using the library. The library can be used to (a) identify the function(s) of genes of interest, (b) screen for genes that may encode useful or putative drug targets, (c) screen for genes that may encode the proteins acting as site(s) of action of drugs, toxins and other chemicals, and (d) screen compounds for modulating effects on proteins encoded by genes of interest. Alternatively, various comparisons can be made between the library database sequences and any other sequence database as would be familiar to those practiced in the art.

The novel utility of the library lies in the ability to search the library database for a gene of interest based upon some knowledge of the nucleic acid or amino acid sequence. Alternatively, the database could be searched for a gene of interest on the basis of knowledge of desired phenotype. With library of insertional mutations, it is possible to identify a sperm sample or a fish containing an insertion in any gene which is known or thought to produce a disease condition. The identified sperm can be used to breed progeny fish bearing the mutation and thereby enabling a means to study the gain-of-function or loss-of-function of the encoded gene product. Alternatively, the identified fish can be used to study the gain-of-function or loss-of-function of the encoded gene product. The library can be surveyed for mutations in specific genes by polymerase chain reaction methods using an oligonucleotide primer specific for the designated gene with another oligonucleotide specific for the insertion sequence. Alternatively the library can be searched by sequence homology using a standard BLAST query of the database composed of all library insertions. Alternately, the library can be screened to recover all insertions within a gene family for which one member is known to contribute to a disease condition. In addition, the library can be used to generate site-specific deletions using irradiation, for example, where the identified retroviral insertion is located near the gene, but is not disrupting the gene. Once a sequence is identified, the specific sperm or the specific fish in the library can be accessed and used to (a) identify the function(s) of genes of interest, (b) screen for genes that may encode useful or putative drug targets, (c) screen for genes that may encode the proteins acting as site(s) of action of drugs, toxins and other chemicals, and (d) screen compounds for modulating effects on proteins encoded by genes of interest. These studies are accomplished by means familiar to those practiced in the art. Transgenic zebrafish are directly generated from the sperm found in the library as is familiar to those practiced in the art.

Genetic mutations often correlate with disease (e.g., breast cancer, Parkinson's, obesity, ataxia telangiectasia, etc.). Given that the present invention allows for directed gene discovery, additional embodiments of the present invention include methods for identifying the genetic basis of disease. For example, genetic mutations can often contribute to the disease state by altering the normal regulatory processes of the cell. As such, once a given transcription factor or regulatory protein has been associated with a given disease, the entire protein, or a relevant domain therefrom, may be used to identify genes directly or indirectly regulated by the protein or which interact with the protein. Consequently, the present invention may be used to identify the various proteins involved in a given disease or disease pathway. Diseases of particular interest include, but are not limited to: autoimmune disease, systemic lupus erythematosus, rheumatoid arthritis, inflammatory response, post-angioplasty vascular inflammatory response, bacterial or viral infection, inflammatory bowel disease, diabetes, multiple sclerosis, cancer, asthma, muscular dystrophy, Alzheimer's disease, dementia and other neuropathologies, hypertension, hemochromatosis, porphyrias, galactosemia, hyperlipoproteinemia, gout, interstitial lung disease, platelet disorders, myasthenia gravis, congenital heart disease, cystic fibrosis, and obesity. In addition, given that the present invention allows for directed gene discovery, additional embodiments of the present invention include methods for identifying gene function.

In addition to disease, the presently described methods and libraries are equally well suited for identifying the molecular basis for genetically determined advantages such as prolonged life-span, low cholesterol, low blood pressure, low cancer risk, low diabetes, low obesity, and attenuation of severity or prevention of all inflammatory disorders, including, but not limited to coronary artery disease, multiple sclerosis, rheumatoid arthritis, systemic lupus erythematosus, and inflammatory bowl disease.

Additionally, the sequence information may be used to generate a highly specific probe for isolating both genomic clones from existing databases, as well as a full length cDNA or promoters or other regulatory sequences. Additionally, the probe may be used to isolate the homologous gene from sufficiently related species, including humans. Once isolated, the gene may be over expressed, or used to generate a targeted knock-out vector that may be used to generate cells and animals that are homozygous for the mutation of interest. Such animals and cells are deemed to be particularly useful as disease models (i.e., cancer, genetic abnormalities, AIDS, etc.), for developmental study, to assay for toxin susceptibility or the efficacy of therapeutic agents, and as hosts for gene delivery and therapy experiments (e.g., experiments designed to correct a specific genetic defect in vivo).

With a library of insertional mutations, it is possible to identify a sperm sample or a fish containing an insertion in any gene which is known to produce a disease condition. The identified sperm can be used to breed progeny fish bearing the mutation, thereby enabling a means to study the gain-of-function or loss-of-function of the encoded gene product. The fish can be used directly to study the gain-of-function or loss-of-function of the encoded gene product. The library can be surveyed for mutations in specific genes by polymerase chain reaction methods using an oligonucleotide primer specific for the designated gene with another oligonucleotide specific for the insertion sequence. Alternatively the library can be searched by sequence homology using a sequence alignment analysis of the database composed of all library insertions. For example, humans bearing mutations is ferrochelatase, an enzyme in the heme biosynthesis pathway, experience erythropoietic protoporphyria, a condition which shows light-dependent hemolysis and liver disease. While it is difficult to study damage initiated indirectly by light to non-cutaneous organ in mammals, it is possible to use zebrafish to study this condition in a non-invasive manner. Further it is possible to identify similarly acting mutations in paralogous genes and to study the resulting disease phenotypes in zebrafish. (Childs et al., 2000).

Transgenic animals produced using the information available from the presently described library are useful to (a) identify the function(s) of genes of interest, (b) screen for genes that may encode useful or putative drug targets, (c) screen for genes that may encode the proteins acting as site(s) of action of drugs, toxins and other chemicals, and (d) screen compounds for modulating effects on proteins encoded by genes of interest. These animals are also useful for the study of basic biological processes and diseases including, but not limited to, aging, cancer, autoimmune disease, immune disorders, alopecia, glandular disorder, inflammatory disorders, diabetes, arthritis, high blood pressure, atherosclerosis, cardiovascular disease, pulmonary disease, degenerative diseases of the neural or skeletal systems, Alzheimer's disease, Parkinson's disease, asthma, developmental disorders or abnormalities, infertility, epithelial ulcerations, and microbial pathogenesis.

One use of the library of the present invention is to rapidly identify the function of genes. Fish containing mutations of genes of interest, generated as described herein, may be examined for specific phenotypes, much as knockout mice are studied to determine the same. In accordance with this aspect of the invention, this use of the library is capable of identifying the function of genes that have been or can be missed using conventional and currently available cloning techniques. By using the library described herein, unknown and/or uncharacterized genes and their function can be rapidly identified. The proteins encoded by these genes have use as, among other things, human therapeutics and diagnostics and as targets for drug discovery.

A "known" gene is directed to the level of characterization of a gene. The invention allows identification of genes that have been characterized, as well as identification of genes that have not been characterized. Different levels of characterization are possible. These include detailed characterization, such as cloning, DNA, RNA, and/or protein sequencing, and relating the regulation and function of the gene to the cloned sequence (e.g., recognition of promoter and enhancer sequences, functions of the open reading frames, introns, and the like). Characterization can be less detailed, such as having mapped a gene and related function, or having a partial amino acid or nucleotide sequence, or having purified a protein and ascertained a function. Characterization may be minimal, as when a nucleotide or amino acid sequence is known or a protein has been isolated but the function is unknown. Alternatively, a function may be known but the associated protein or nucleotide sequence is not known or is known but has not been correlated to the function. Finally, there may be no characterization in that both the existence of the gene and its function are not known. The invention allows identification of any gene at any of these or other specific degrees of characterization.

A gene of interest can be identified based on a phenotype conferred by the gene having the insert. Examples of selectable phenotypes include cellular proliferation, growth factor independent growth, colony formation, cellular differentiation (e.g., differentiation into a neuronal cell, muscle cell, epithelial cell, etc.), anchorage independent growth, activation of cellular factors (e.g., kinases, transcription factors, nucleases, etc.), expression of cell surface receptors/proteins, gain or loss of cell-cell adhesion, migration, cellular activation and phenotypes of disease conditions. Identification of gene function is important because the protein encoded by the gene or the gene itself is presumably responsible for the observed phenotype. Thus, the protein encoded by the gene or the gene itself may be an important therapeutic drug or drug target for treating or inducing the observed phenotype. In addition, this use of the library can identify all of the genes and proteins involved with a particular pathway or disease condition of interest, e.g., diabetes. The identification of such genes provides a collection of genes and/or proteins which are putative drug targets for the pathway or disease of interest. Since these genes are associated with specific zebrafish sperm or fish in the library, transgenic fish prepared as described herein can be used to screen potential drugs for use in treating or preventing the disease of interest.

For such screens and other screening methods described herein, the transgenic fish harboring the desired insert or representing all inserts can be screened using a number of assays. Depending on the characteristics of the protein(s) of interest (e.g., secreted versus intracellular proteins), the library can be screened for biochemical activity, enzymatic activity, gene regulation, phenotypic characteristic(s) and activity of a disease models, e.g., is the cell or organism resistant to an inserted transgene associated with a disease model. Other assay formats can also be used as known in a skilled artisan. In addition, the screening can be performed on different genetic states of the fish. In one embodiment, screening may be performed on fish produced by fertilizing zebrafish eggs with at least one sperm cell of the zebrafish sperm insertional library. In a second embodiment, screening may be performed on at least one founder fish or its progeny of the zebrafish insertional library. In one aspect of this embodiment, the progeny are heterozygote. In a second aspect of this embodiment, the progeny have been bred to be homozygote. In third embodiment, the screening may be performed on at least one haploid embryo. Haploid embryos may be prepared as described by, for example, Westerfield (2000). In a fourth embodiment, the screening may be performed on at least one gynogenetic diploid embryo. Gynogenetic diploid embryos may be prepared as described by, for example, Westerfield (2000). As used herein, screening is intended to include each of these embodiments, as well as isolated cells or secreted or excreted products as described further herein, and is intended to include in vivo and in vitro screening methods as described herein and as well known to skilled artisans.

A transgenic fish having a gene of interest can be exposed to compounds to assess the effect of the compound on the modulation of the protein encoded by the gene of interest and the biochemical pathway in which the protein encoded by the gene of interest is involved. For example, test compounds can be administered to transgenic fish harboring the gene of interest. Alternatively and preferably, the compound can be dosed in the water holding the transgenic fish, with the fish taking up substances via their gills. The compounds can also be dosed in the water holding the haploid embryos or the gynogenetic diploid embryos. By comparing the expression of the gene or protein encoded by the gene in fish exposed to a test compound to those that are not exposed, the effect of the compound on the modulation of the protein encoded by the gene of interest can be assessed. Test compounds can act as either inhibitors or activators of the gene. In this manner, compounds which are useful as drugs for treating or preventing disease conditions associated with gene of interest are identified. Similarly, toxins, potential therapeutic products or other chemicals can be screened using the present library to identify the site of action of these compounds and to effect of these compounds on the genes or proteins of the library. By identifying fish that, by virtue of a specific mutation or mutation(s), no longer respond to a compound, a gene encoding the protein required for the action of said compound is identified.

The invention also encompasses zebrafish model-based assays for the identification of compounds exhibiting the ability to alter or correct phenotypes associated with the various genotypes identified and constructed using the present methods. Such model-based assays can also be used as a standard to assay for purity and potency of the compounds, including recombinantly or synthetically produced proteins or compounds.

In addition to the zebrafish based systems for identifying compounds of interest, other in vitro systems can also be used to identifying compounds that inhibit, activate or bind to proteins encoded by a gene of interest. The identified compounds may be useful, for example, in modulating the activity of wild type and/or mutant gene products. In vitro systems may also be utilized to screen for compounds that disrupt normal regulatory interactions.

The assays used to identify compounds that bind to proteins involve preparing a reaction mixture of a given protein and the test compound under conditions and for a time sufficient to allow the two components to interact and bind, thus forming a complex which can be removed and/or detected in the reaction mixture. The protein used can vary depending upon the goal of the screening assay. For example, where agonists of the natural ligand are sought, a full length protein, or a fusion protein containing a protein or polypeptide that affords advantages in the assay system (e.g., labeling, isolation of the resulting complex, etc.) can be utilized. In addition, in vitro assays may involve substances, enzymes, ant the like which are secreted from the fish, which are then assayed.

The screening assays can be conducted in a variety of ways. For example, one method to conduct such an assay would involve anchoring the protein, polypeptide, peptide or fusion protein or the test substance onto a solid phase and detecting binding between the protein and test compound or mutant cell. In one embodiment of such a method, the receptor protein reactant may be anchored onto a solid surface, and the test compound, which is not anchored, may be labeled, either directly or indirectly. In another embodiment of the method, the test protein is anchored on the solid phase and is complexed with labeled antibody (and where a monoclonal antibody is used, it is preferably specific for a given region of the protein). Then, a test compound could be assayed for its ability to disrupt the association of the protein/antibody complex.

Alternatively, a reaction can be conducted in a liquid phase, the reaction products separated from unreacted components, and complexes detected; e.g., using an immobilized antibody specific for the test protein, polypeptide, peptide or fusion protein, or the test compound to anchor any complexes formed in solution, and a labeled antibody specific for the other component of the possible complex to detect anchored complexes.

The basic principle of the assay systems used to identify compounds that interfere with the interaction between a protein and its binding partner or partners involves preparing a reaction mixture containing the test protein, polypeptide, peptide or fusion protein as described above, and the binding partner under conditions and for a time sufficient to allow the two to interact and bind, thus forming a complex. In order to test a compound for inhibitory activity, the reaction mixture is prepared in the presence and absence of the test compound. The test compound can be initially included in the reaction mixture, or may be added at a time subsequent to the addition of the test protein and its binding partner. Control reaction mixtures are incubated without the test compound or with a placebo. The formation of any complexes between the test protein and the binding partner is then detected. The formation of a complex in the control reaction, but not in the reaction mixture containing the test compound, indicates that the compound interferes with the interaction of the test protein and the binding partner.

Further details concerning the above described in vitro systems and additional in vitro systems can be found in U.S. Pat. No. 6,080,576.

A variety of test compounds can be evaluated in accordance with the present invention. In certain embodiments, the compounds to be tested can be derived from libraries (i.e., are members of a library of compounds). While the use of libraries of peptides is well established in the art, new techniques have been developed which have allowed the production of mixtures of other compounds, such as benzodiazepines (Bunin and Ellman, 1992; DeWitt et al., 1993), peptoids (Zuckermann, 1994), oligocarbamates (Cho et al., 1993), and hydantoins (DeWitt et al., 1993). An approach for the synthesis of molecular libraries of small organic molecules with a diversity of 104-105 as been described (Carell et al., 1994a; Carell et al., 1994b).

The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, 1997). Other exemplary methods for the synthesis of molecular libraries can be found in the art, for example in Erb et al. (1994), Horwell et al. (1996) and Gallop et al. (1994).

Libraries of compounds may be presented in solution (e.g., Houghten et al., 1992), or on beads (Lam et al., 1991), chips (Fodor et al., 1993), bacteria (U.S. Pat. No. 5,223,409), spores (U.S. Pat. No. 5,223,409), plasmids (Cull et al., 1992) or on phage (Scott and Smith, 1990; Devlin et al., 1990; Cwirla et al., 1990; Felici et al., 1991). In still another embodiment, the combinatorial polypeptides are produced from a cDNA library.

Exemplary compounds which can be screened for activity include, but are not limited to, peptides, nucleic acids, carbohydrates, small organic molecules, and natural product extract libraries.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. Several approaches for use in rational drug design include analysis of three-dimensional structure, alanine scans, molecular modeling and use of anti-id antibodies. These techniques are well known to those skilled in the art. Such techniques may include providing atomic coordinates defining a three-dimensional structure of a protein complex formed by said first polypeptide and said second polypeptide, and designing or selecting compounds capable of interfering with the interaction between a first polypeptide and a second polypeptide based on said atomic coordinates.

Following identification of a substance which modulates or affects polypeptide activity, the substance may be further investigated. Furthermore, it may be manufactured and/or used in preparation, i.e., manufacture or formulation, or a composition such as a medicament, pharmaceutical composition or drug. These may be administered to individuals.

A substance identified as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This approach might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process. Such techniques include those disclosed in U.S. Pat. No. 6,080,576.

A template molecule is then selected, onto which chemical groups that mimic the pharmacophore can be grafted. The template molecule and the chemical groups grafted thereon can be conveniently selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent it is exhibited. Further optimization or modification can then be carried out to arrive at one or more final mimetics for in vivo or clinical testing.

With regard to intervention, any compounds which reverse any aspect of a given phenotype or expression of any gene in vivo and which modulates protein activity or binding with binding partner in vitro should be considered as candidates for further development or potential use in humans. Dosages of test agents may be determined by deriving dose-response curves using methods well known in the art.

As previously noted, the present invention has been described with reference to zebrafish for convenience. It is understood that other fish and other animals can be used in place of zebrafish. Thus, it is understood that the present invention pertains to the use of the maize Ac/Ds transposable elements in vertebrates, including fish, birds, and other animals including mammals. Vertebrate cells can also incorporate the modified Ds element of this invention in the presence of the modified Ac transposase protein. Cells from fish, birds and other animals can be used, as can cells from mammals including, but not limited to, rodents, such as rats or mice, ungulates, such as cows, goats, sheep and pigs or cells from a human.

In the gene transfer system of this invention the modified Ac transposase protein can be introduced into the cell as a protein or as nucleic acid encoding the protein. In one embodiment the nucleic acid encoding the protein is RNA and in another, the nucleic acid is DNA. Further, nucleic acid encoding the modified Ac transposase protein can be incorporated into a cell through a viral vector, cationic lipid, or other standard transfection mechanisms including electroporation or particle bombardment used for eukaryotic cells. Following introduction of nucleic acid encoding modified Ac transposase, the modified Ds element of this invention can be introduced into the same cell. Alternatively, the modified Ds element of this invention can be introduced into the cell simultaneously with the modified Ac transposase protein or nucleic acid encoding the modified Ac transposase protein.

In a further aspect, the modified maize Ac/Ds transposable elements described above are useful for gene therapy in vertebrates, such as through the use of the above described gene transfer system for gene therapy. Gene therapy has the potential to improve the clinical outcome of many diseases, including cancers, by transferring therapeutic genes into diseased cells, including tumor cells, or normal host tissue. Gene transfer into tumor cells or tumor-associated stroma is being employed to induce tumor cell death, stimulate anti-tumor immune response, inhibit angiogenesis, and control tumor cell growth. Viral vectors have been used to achieve this proof of principle in animal models and, in select cases, in human clinical trials. Nevertheless, there has been considerable interest in developing nonviral vectors for cancer gene therapy. Nonviral vectors are simpler, more amenable to large-scale manufacture, and potentially safer for clinical use. Nonviral vectors were once limited by low gene transfer efficiency and transient or steadily declining gene expression. However, recent improvements in plasmid-based vectors and delivery methods are circumventing these obstacles. Nonviral vector technology for use in gene therapy includes transposons (Liu et al., 2006; Ohlfest et al., 2005; Essner et al., 2005; Hackett et al., 2005; Converse et al., 2004; Liu et al., 2004; Izsvak and Ivics, 2004; Kaminski et al., 2002; Richardson et al., 2002). Thus, the gene transfer system with the modified maize Ac/Ds transposable elements described herein is useful for gene therapy in vertebrates.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Anand, 1992; Guthrie and Fink, 1991; Harlow and Lane, 1988, *Antibodies*, (Cold Spring Harbor Laboratory Press, Cold Spring Harbor, N.Y.); Jakoby and Pastan, 1979; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Hogan et al., *Manipulating the Mouse Embryo*, (Cold Spring Harbor Laboratory Press, Cold Spring Harbor, N.Y., 1986); Westerfield, M., *The zebrafish book. A guide for the laboratory use of zebrafish (Danio rerio)*, (4th Ed., Univ. of Oregon Press, Eugene, 2000).

EXAMPLES

The present invention is described by reference to the following Examples, which are offered by way of illustration and are not intended to limit the invention in any manner. Standard techniques well known in the art or the techniques specifically described below were utilized. The Examples demonstrate that the invention is applicable to and functions in all vertebrates as shown by studies utilizing zebrafish and a human cell line.

Example 1

Materials and Methods

Plasmid Constructs

The construct containing EGFP (Clontech Laboratories, USA) under 2.25 kb promoter of keratin 8 (krt8) gene (GenBank accession number AF440690) was obtained from Dr. Zhiyuan Gong from the National University of Singapore. The 30.1 kb krt8:EGFP fragment was placed into a 0.6 kb miniDs construct (Weil and Kunze, 2000).

The NLS-TPase cDNA was PCR-amplified using primers "Ac5'-1": CCAAAGAAG AAGCGTAAGGTAGAAATG-GCTATTGTTCATGAACCACA (SEQ ID NO:14) and "Ac3": GTATCGAT AAGCTTGATATCGAATTCC (SEQ ID NO:15) and pWL80 plasmid (Weil and Kunze, 2000) as a template. The product was used as a template in the secondary PCR using primers "Ac5'-2": CGCGGATCCGCCAC-CATGGGTCCTCCAAAGAAGAAGCGTAAGGT AG (SEQ ID NO:16) and "Ac3": GTATCGATAAGCT-TGATATCGAATTCC (SEQ ID NO:17). The product containing nuclear localization sequence (NLS) (MGPP-KKKRKVE (SEQ ID NO:2)) fused to a truncated Ac TPase$_{103-807}$ and Kozak sequence was digested with BamHI and cloned into BglII site of the pSP64T vector (Krieg and Melton. 1984). The NLS$^{K5E}$-TPase was obtained by chance during cloning of the NLS-TPase construct due to a random mismatch in the primer. To produce the NoNLS construct, the corresponding NLS sequence was removed using QuikChange™ Site Directed Mutagenesis Kit (Stratagene) and primers: CTCAACTTTG GCAGATCCGCCACCATG- GCTATTGTTCATGAACCACAACC (SEQ ID NO:38) and GGT TGTGGTTCATGAACAATAGCCATGGTG-GCGGATCTGCCAAAGTTGAG (SEQ ID NO:39).

To produce NLS-TPase-EGFP and NLS$^{K5E}$-TPase-EGFP fusion constructs PCR amplified NLS-TPase and NLS$^{K5E}$-TPase fragments using primers AGAGGGATCCAGCTCA GAATAAACGCTCAAC (SEQ ID NO:40) and AGAGAC-CGGTCCTGGAGAGGAGCCAC TTGCTA (SEQ ID NO:41) and cloned it into krt8-EGFP plasmid (Gong et al., 2002) using AgeI and BamHI. To produce NLS-EGFP and NLS$^{K5E}$-EGFP constructs the Ac TPase$_{103-807}$ CDS sequence was deleted from the NLS-TPase-EGFP and NLS$^{K5E}$-TPase-EGFP constructs correspondingly using QuikChange™ Site Directed Mutagenesis Kit (Stratagene) and primers: AGAA-GAAGCGTAAGGTAGAAATGGTGAG-CAAGGGCGAGGAGC (SEQ ID NO:42) and GCTC-CTCGCCCTTGCTCACCATTTCTACCTTACGCTTCTTCT (SEQ ID NO:43).

RNA Preparation and Injections

The TPase plasmid were linearized with BamHI (cut downstream of the polyA tail) and used for in vitro transcription of capped transposase RNA. The mMESSAGE mMA-CHINE SP6 kit (Ambion) was used. The product was purified using RNeasy Mini Kit (QIAGEN, Germany). 5-10 pg of plasmid DNA with 25-50 pg of in vitro synthesized transposase mRNA were co-injected into zebrafish embryos at the 1-2-cell stage. The actual amount of injected RNA was empirically adjusted to produce 50% embryo survival rate.

Zebrafish

Zebrafish was maintained according to established protocols (Westerfield, 2000).

Analysis of the Ds Excision Sites

Two primers flanking the Ds donor site that enclosed 3.7 kb long Ds and 120 bp of the flanking sequences were designed. The primers have the following sequences: GAGAATTT CACTTGTTGACTAGA (SEQ ID NO:18) and GCGCAT-GAACTCCTTGATGAC (SEQ ID NO:19). The PCR conditions without extension and with a short annealing time were used to prevent amplification of the long donor product: 94° C. for 30 sec and 55° C. for 10 sec for 35 cycles. Under these conditions only the 120 bp Ds-excision product could amplify but not 3.7 kb-long donor site that was present in excess. Products were separated using 1.8% agarose gel. The bands were cut from the gel, purified using QIAquick Gel Extraction Kit (QIAGEN, Germany), and sequenced using ABI Cycle Sequencing chemistry (PE Applied Biosystems, CA) and an ABI Prism 310 Genetic Analyzer with Data Collection Software (PE Applied Biosystems, USA) supplied by the producer.

Analyses of Ds Flanking Sequences

TAIL-PCR (thermal asymmetric interlaced PCR) was performed as described previously (Liu and Whittier, 1995; Parinov et al., 2004) using the following set of primers: Ds5'-1: CCGTTTACCGTTTTGTATATCCCG (SEQ ID NO:21); Ds5'-2: CGTTCCGTTTTC GTTTTTTACC (SEQ ID NO:22); Ds5'-3: CGGTCGGTACGGGATTTTCC (SEQ ID NO:23); Ds3'-1: CGATTACCGTATTTATCCCGTTCG (SEQ ID NO:24); Ds3'-2: CCGGTATATCCC GTTTTCG (SEQ ID NO:25); Ds3'-3: GAAATTGAAAACCGTA-GAGGT (SEQ ID NO:26); AD-1: WGTGNAGNAN-CANAGA (SEQ ID NO:27); AD-2: WCAGNTGWTNGT-NCTG (SEQ ID NO:28); AD-3: STTGNTASTNCTNTGC (SEQ ID NO:29); AD-4: NCASGAWAGNCSW CAA (SEQ ID NO:30). Products of the secondary and tertiary reactions were separated using 1.8% agarose gel. The individual bands from the "band shift" pairs were cut from the gel and purified using QIAquick Gel Extraction Kit (QIAGEN, Germany), and sequenced with Ds5'-3 and Ds3'-3 primers using ABI Cycle Sequencing chemistry (PE Applied Biosystems, CA) and an ABI Prism 310 Genetic Analyzer with Data Collection Software (PE Applied Biosystems, USA) supplied by the producer.

Southern Blot Hybridization

EcoRI-digested genomic DNA was fractionated by gel electrophoresis transferred to positively charged nylon membrane (Roche Applied Science, USA) by capillary blotting (Sambrook et al., 1989) and crosslinked by UV irradiation. The DNA probe for EGFP was labeled with digoxigenin (Roche Applied Science, USA) using PCR DIG synthesis kit. We used DIG EasyHyb DIG Wash and Block Buffer Set for hybridization, alkaline phosphatase labeled anti-DIG antibody and CDP-Star chemiluminescent substrate (Roche Applied Science, USA) for detection of the hybridized probe. Hybridization and detection was carried out as described in the manufacture user's guide.

Example 2

Experimental Design

A two-component system consisting of a donor construct with a non-autonomous Ds element, and a messenger RNA encoding a modified Ac transposase was utilized with an aim to produce Ds insertions in the zebrafish genome. The Ds construct carried EGFP gene under the zebrafish 2.25 kb keratin 8 (kat8) promoter (Gong et al., 2002), confined between 5'- and 3'-end cis-required sequences of miniDs element (Weil and Kunze, 2000) (FIG. 1A). The second construct harbored the coding sequence of a truncated Ac transposase (TPase$_{103-807}$) (Houba-Herin et al., 19990) fused to an animal-specific synthetic nuclear localization signal (NLS; MGPPKKKRKVE (SEQ ID NO:2)) analogous to that of SV40 large T antigen (FIG. 1B). The gene encoding such a chimeric NLS-TPase$_{103-807}$ fusion (NLS-TPase) was cloned into the pSP64T plasmid (Krieg and Melton, 1984) containing the SP6 promoter for in vitro transcription. This plasmid also contained the 5'- and 3'-UTRs of the *Xenopus* β-globin gene and a dA$_{32}$ polyA tail. Two similar TPase constructs were additionally made (FIGS. 1B and 1C): one containing only the TPase$_{103-807}$ sequence without NLS (NoNLS-TPase) and the other containing an amino acid substitution (K to E) at the 5th position of the NLS (NLS$^{K5E}$-TPase).

Table 1 shows the nucleotide sequence of the modified Ac transposase constructs. Table 1A shows the NLS-containing construct and Table 1B shows the NLS$^{K5E}$-containing construct. Plasmid sequences are shown in lower case. The SP6 promoter (nucleotides 70-89 of SEQ ID NO:11 or 37) is shown in lower case bold italics. The Kozak sequence (nucleotides 152-157 of SEQ ID NO:11 or 37) is shown in caps preceding the coding sequence for the synthetic NLS (upper case, bolded and underlined; nucleotides 158-190 of SEQ ID NO:11 or 37). The coding sequence for truncated Ac TPase$_{103-807}$ is shown in upper case and bolded (nucleotides 191-2305 of SEQ ID NO:11 or 37) and the stop codon and 3'-UTR of Ac transposase is shown in upper case (nucleotides 2306-2477 of SEQ ID NO:11 or 37). The 5'-UTR of β-globin is represented by nucleotides 89-150 of SEQ ID NO:11 or 37. The 3'-UTR of globin is represented by nucleotides 2478-2624 of SEQ ID NO:11 or 37.

Table 2 shows the amino acid sequence of the modified Ac TPase. Table 2A shows the NLS-Ac TPase and Table 2B shows the NLS$^{K5E}$-Ac TPase. The synthetic NLS (bolded; amino acids 1-11 of SEQ ID NO:20) or NLS$^{K5E}$ (bolded; amino acids 1-11 of SEQ ID NO:44) is fused to truncated Ac TPase$_{103-807}$ (Weil and Kunze, 2000; Houba-Herin et al., 1990; amino acids 12-716 of SEQ ID NO:20 or 44).

TABLE 1

Nucleotide Sequence of the Modified Ac Transposase Construct

A. NLS-Containing Construct

. . . attaggcttgtacatatgtngttagaacgcggctacaattaata cataaccttatgtatcatacacata*cgatt taggtga cactatagaatac aagcttgcttgttcttttttgcagaagctcagaataaacgctcaactttgg cagatccGCCACC<u>ATGGGTCCTCCAAAGAAGAAGCGTAAGGTAGAAATGG
CTATTGTTCATGAACCACAACCACAACCACAACCACAACCAGAACCACAA
CCACAGCCACAACCTGAACCCGAAGAAGAAGCACCACAGAAGAGGGCAAA
GAAGTGCACATCGGATGTATGGCAGCATTTCACCAAGAAGGAAATTGAAG
TGGAGGTCGATGGAAAGAAATACGTTCAGGTATGGGGGCATTGCAACTTT
CCTAATTGCAAGGCTAAGTATAGGGCTGAGGGTCATCATGGACAAGCGGA
TTTCGAAATCACTTGAGAACATCACATAGTTTAGTTAAAGGTCAGTTGTG
TCTAAAAAGTGAAAAGGATCATGGCAAAGACATAAATCTCATTGAGCCTT
ATAAGTACGATGAAGTGGTTAGCCTAAAGAAGCTTCATTTGGCAATAATC
ATGCATGAATACCCTTTCAATATTGTAGAACATGAGTACTTTGTTGAGTT
TGTTAAGTCTCTGCGCCCTCACTTTCCAATAAAGTCCCGTGTCACTGCTA
GAAAATATCATGGATTTGTATTTGGAAGAAAAAGAAAAGTTGTATGGA
AAACTAAAAGATGTTCAGTCTCGCTTCAGTACAACTATGGATATGTGGAC
ATCTTGTCAAAATAAGTCATACATGTGTGTCACCATCCATTGGATTGATG
ATGATTGGTGTCTCCAAAAAAGAATTGTTGGCTTTTTTCATGTTGAAGGG
CGCCACACTGGCCAAAGGTTATCACAAACCTTCACTGCAATCATGGTTAA
GTGGAACATTGAGAAAAAATTGTTTGCCTTGTCTTTGGATAATGCTAGTG
CAAATGAAGTAGCTGTGCACGATATATTGAGGATTTGCAGGACACTGATT
CAAATCTAGTTTGTGATGGTGCTTTCTTTCATGTGAGGTGTGCTTGTCAC
ATACTGAACTTGGTTGCAAAGGATGGCTTGGCTGTAATTGCAGGAACAAT
TGAGAAAATCAAAGCGATTGTTCTTGCTGTAAAATCTTCTCCTTTGCAGT
GGGAAGAACTAATGAAGTGTGCTAGTGAATGTGACTTGGATAAATCTAAA
GGGATCTCTATGATGTCTCAACTAGATGGAATTCAACCTATTTGATGTT
GAGGGATGCCTTATATTATAAGCCTGCACTAATAAGGCTTAAAACAAGTG
ATCCTCGCAGGTACGATGCAATTTGTCCTAAAGCCGAGGAGTGGAAGATG
GCATTAACTCTTTTTAAGTGTTTGAAGGAAGTTTTTTGATCTCACTGAAC
TCCTATCTGGTACTCAATATTCCACTGCAAATTTATTTTACAAAGGTTTC
TGTGAGATAAAGGATTTGATTGACCAATGGTGTGTTCATGAAAAATTTGT
CATTAGGAGAATGGCCGTTGCAATGAGTGAAAAGTTTGAGAAATATTGGA
AAGTGTCTAATATTGCACTAGCTGTAGCATGCTTCCTTGACCCTAGGTAC
AAGAAAATATTGATTGAGTTCTATATGAAAAAATTTCATGGTGATTCATA
CAAAGTTCATGTAGATGACTTTGTTAGGGTCATTAGAAAATTGTATCAAT
TCTATTCTAGTTGTAGTCCTTCAGCTCCAAAGACAAAGACAACTACTAAT
GATAGTATGGATGATACCTTGATGGAAAATGAAGATGATGAATTTCAAAA
CTATTTGCATGAGTTGAAGGATTATGATCAAGTAGAGTCAAATGAATTGG
ATAAATATATGTCTGAACCCCTTTTGAAGCATAGTGGTCAGTTTGATATT
TTATCATGGTGGAGGGGAAGGGTTGCAGAATATCCTATTCTCACCCAAAT
TGCAAGGGATGTGCTAGCAATACAAGTGTCAACTGTTGCTTCTGAGTCTG
CGTTCAGTGCTGGTGGTCGTGTTGTTGATCCTTACCGCAATCGTCTTGGT
TCGGAGATTGTTGAAGCTTTGATATGCACAAAAGATTGGGTAGCAGCATC
TAGAAAAGGTGCTACATATTTTCCAACAATGATTGGTGATCTCGAGGTGC
TAGACTCTGTTATTGCTGCTGCAACAAATCATGAGAATCATATGGATGAG
GATGAAGACGCAATAGAATTTTCTAAGAATAATGAAGATGTAGCAAGTGG
CTCCTCTCCATGAGCAATGTGTCTTATGTTTGTTGACAGATGAGCCTTGG
TTGTAATAGTTTATGCATGCTAAGTGCTCCAGATGTGAGCAAGTGATTAT
GAATATGTGTTTTAAACTTTATATTGTGTCATGTGTGCTAGTAGACTTAT
ATGGCTTCTTATGTTAGCCAAGGGGGCCCCGG</u>gatctggttaccactaaa ccagcctcaagaacacccgaatggagtctctaagctacataataccaact tacactttacaaaatgttgtccccaagatgtagccattcgtatctgctc ctaataaaagaaagtttcttcacattctaaaaaaaaaaaaaaaaaaaaa aaaaaaaaaaaaacccccccccccccccctgcaggtcgac . . .
(SEQ ID NO: 11)

B. NLS$^{KSE}$-ContaiNing Construct

. . . attaggcttgtacatatgtngttagaacgcggctacaattaata cataaccttatgtatcatacacata*cgatt taggtgacactatag*aatac aagcttgcttgttcttttttgcagaagctcagaataaacgctcaactttgg cagatccGCCACC<u>ATGGGTCTCCAGAGAAGAAGCGTAAGGTAGAAATGGC
TATTGTTCATGAACCACAACCACAACCACAACCACAACCAGAACCACAAC
CACAGCCACAACCTGAACCCGAAGAAGAAGCACCACAGAAGAGGGCAAAG
AAGTGCACATCGGATGTATGGCAGCATTTCACCAAGAAGGAAATTGAAGT
GGAGGTCGATGGAAAGAAATACGTTCAGGTATGGGGGCATTGCAACTTTC
CTAATTGCAAGGCTAAGTATAGGGCTGAGGGTCATCATGGAACAAGCGGA
TTTCGAAATCACTTGAGAACATCACATAGTTTAGTTAAAGGTCAGTTGTG
TCTAAAAAGTGAAAAGGATCATGGCAAAGACATAAATCTCATTGAGCCTT
ATAAGTACGATGAAGTGGTTAGCCTAAAGAAGCTTCATTTGGCAATAATC
ATGCATGAATACCCTTTCAATATTGTAGAACATGAGTACTTTGTTGAGTT
TGTTAAGTCTCTGCGCCCTCACTTTCCAATAAAGTCCCGTGTCACTGCTA
GAAAATATCATGGATTTGTATTTGGAAGAAAAAGAAAAGTTGTATGGA
AAACTAAAAGATGTTCAGTCTCGCTTCAGTACAACTATGGATATGTGGAC
ATCTTGTCAAAATAAGTCATACATGTGTGTCACCATCCATTGGATTGATG
ATGATTGGTGTCTCCAAAAAAGAATTGTTGGCTTTTTTCATGTTGAAGGG
CGCCACACTGGCCAAAGGTTATCACAAACCTTCACTGCAATCATGGTTAA
GTGGAACATTGAGAAAAAATTGTTTGCCTTGTCTTTGGATAATGCTAGTG</u>

TABLE 1-continued

Nucleotide Sequence of the Modified Ac Transposase Construct

CAAATGAAGTAGCTGTGCACGATATAATTGAGGATTTGCAGGACACTGAT

TCAAATCTAGTTTGTGATGGTGCTTTCTTTCATGTGAGGTGTGCTTGTCA

CATACTGAACTTGGTTGCAAAGGATGGCTTGGCTGTAATTGCAGGAACAA

TTGAGAAAATCAAAGCGATTGTTCTTGCTGTAAAATCTTCTCCTTTGCAG

TGGGAAGAACTAATGAAGTGTGCTAGTGAATGTGACTTGGATAAATCTAA

AGGGATCTCATATGATGTCTCAACTAGATGGAATTCAACCTATTTGATGT

TGAGGGATGCCTTATATTATAAGCCTGCACTAATAAGGCTTAAAACAAGT

GATCCTCGCAGGTACGATGCAATTTGTCCTAAAGCCGAGGAGTGGAAGAT

GGCATTAACTCTTTTTAAGTGTTTGAAGAAGTTTTTTGATCTCACTGAAC

TCCTATCTGGTACTCAATATTCCACTGCAAATTTATTTTACAAAGGTTTC

TGTGAGATAAAGGATTTGATTGACCAATGGTGTGTTCATGAAAAATTTGT

CATTAGGAGAATGGCCGTTGCAATGAGTGAAAAGTTTGAGAAATATTGGA

AAGTGTCTAATATTGCACTAGCTGTAGCATGCTTCTTGACCCTAGGTACA

AGAAAATATTGATTGAGTTCTATATGAAAAAATTTCATGGTGATTCATAC

AAAGTTCATGTAGATGACTTTGTTAGGGTCATTAGAAATTGTATCAATTC

TATTCTAGTTGTAGTCCTTCAGCTCCAAAGACAAAGACAACTACTAATGA

TAGTATGGATGATACCTTGATGGAAAATGAAGATGATGAATTTCAAAACT

ATTTGCATGAGTTGAAGGATTATGATCAAGTAGAGTCAAATGAATTGGAT

AAATATATGTTGAACCCCTTTTGAAGCATAGTGGTCAGTTTGATATTTTA

TCATGGTGGAGGGGAAGGGTTGCAGAATATCCTATTCTCACCCAAAATTG

CAAGGGATGTGCTAGCAATACAAGTGTCAACTGTTGCTTCTGAGTCTGCG

TTCAGTGCTGGTGGTCGTGTTGTTGATCCTTACCGCAATCGTCTTGGTTC

GGAGATTGTTGAAGCTTTGATATGCACAAAAGATTGGGTAGCAGCATCTA

GAAAAGGTGCTACATATTTTCCAACAATGATTGGTGATCTCGAGGTGCTA

GACTCTGTTATTGCTGCTGCAACAAATCATGAGAATCATATGGATGAGGA

TGAAGACGCAATAGAATTTTCTAAGAATAATGAAGATGTAGCAAGTGGCT

CCTCTCCATGAGCAATGTGTCTTATGTTTGTTGACAGATGAGCCTTGGTT

GTAATAGTTTATGCATGCTAAGTGCTCCAGATGTGAGCAAGTGATTATGA

ATATGTGTTTTAAACTTTATATTGTGTCATGTGTGCTAGTAGACTTATAT

GGCTTCTTATGTTAGCCAAGGGGGCCCCGgatctggttaccactaaacc agcctcaagaacacccgaatggagtctctaagctacataataccaactta cactttacaaaatgttgtcccccaagatgtagccattcgtatctgctcct aataaaaagaaagtttcttcacattctaaaaaaaaaaaaaaaaaaaaaa aaaaaaaaaaacccccccccccccccctgcaggtcgac . . .
(SEQ ID NO: 37)

TABLE 2

Amino Acid Sequence of the Modified Ac TPase

A. KLS-Containing Modified Ac TPase
MGPPKKKKRKVEMAIVHEPQPQPQPQPEPQPQPQPEPEEEAPQKRAKKCT

SDVWQHFTKKEIEVEVDGKKYVQVWGHCNFPNCKAKYRAEGHHGTSGFRN

HLRTSHSLVKGQLCLKSEKHGKDINLIEPYKYDEVVSLKKLHLAIIMHEY

PFNIVEHEYFVEFVKSLRPHFPIKSRVTARKYIMDLYLEEKEKLYGKLKD

VQSRFSTTMDMWTSCQNKSYMCVTIHWIDDDWCLQKRIVGFFHVEGRHTG

QRLSQTFTAIMVKWNIEKKLFALSLDNASANEVAVHDIIEDLQDTDSNLV

CDGAFFHVRCACHILNLVAKDGLAVIAGTIEKIKAIVLAVKSSPLQWEEL

MKCASECDLDKSKGISYDVSTRWNSTYLMLRDALYYKPALIRLKTSDPRR

YDAICPKAEEWKMALTLFKCLKKFFDLTELLSGTQYSTANLFYKGFCEIK

DLIDQWCVHEKFVIRRMAVAMSEKFEKYWKVSNIALAVACFLDPRYKKIL

IEFYMKKFHGDSYKVHVDDFVRVITKLYQFYSSCSPSAPKTKTTTNDSMD

DTLMENEDDEFQNYLHELKDYDQVESNELDKYMSEPLLKHSGQFDILSWW

RGRAVAEYPILTQIARDVLAIQVSTVASESAFSAGGRVVDPYRNRLGSEI

VEALICTKDWVAASRKGATYFPTMIGDLEVLDSVIAAATNHENHMDEDED

AIEFSKNNEDVASGSSP
(SEQ ID NO: 20)

B. NLS$^{KSE}$-Containing Modified Ac TPase
MGPPEKKRKVEMAIVHEPQPQPQPQPEPQPQPQPEPEEEAPQKRAKKC

TSDVWQHFTKKEIEVEVDGKKYVQVWGHCNFPNCKAKYRAEGHHGTSGFR

NHLRTSHSLVKGQLCLKSEKDHGKDINLIEPYKYDEVVSLKKLHLAIIMH

EYPFNIVEHEYFVEFVKSLRPHFPIKSRVTARKYIMDLYLEEKKLYGKLK

DVQSRFSTTMDMWTSCQNKSYMCVTIHWIDDDWCLQKRIVGFFHVEGRHT

GQRLSQTFTAIMVKWNIEKKLFALSLDNASANEVAVHDIIEDLQDTDSNL

VCDGAFFHVRCACHILNLVAKDGLAVIAGTIEKIKAIVLAVKSSPLQWEE

LMKCASECDLDKSKGISYDVSTRWNSTYLMLRDALYYKPALIRLKTSDPR

RYDAICPKAEEWKMALTLFKCLKKFFDLTELLSGTQYSTANLFYKGFCEI

KDLIDQWCVHEKFVIRRMAVAMSEKFEKYWKVSNIALAVACFLDPRYKKI

LIEFYMKKFHGDSYKVHVDDFVRVIRKLYQFYSSCSPSAPKTKTTTNDSM

DDTLMENEDDEFQNYLHELKDYDQVESNELDKYMSEPLLKHSGQFDILSW

WRGRVAEYPILTQIARDVLAIQVSTVASESAFSAGGRVVDPYRNRLGSEI

VEALICTKDWVAASRKGATYFPTMIGDLEVLDSVIAAATNHENEMDEDED

AIEFSKNNEDVASGSSP
(SEQ ID NO: 44)

Table 3 shows the nucleotide sequence of the modified Ds construct. The EGFP gene under zebrafish keratin 8 (krt8) promoter was confined between 247 bp of 5'-Ds end sequence (nucleotides 3657-3903 of SEQ ID NO:1) and 370 bp of 3'-Ds end sequence (nucleotides 43-412 of SEQ ID NO:1) (Weil and Kunze, 2000), shown in bolded, underlined upper case letters. These two Ds end sequences are also called "minimal Ds" implying that shortening it even further will negatively affect transposition efficiency. The enhanced green fluorescent protein (EGFP) gene was used for selection of transgenic fish. The krt8-promoter—EGFP (lower case) was confined between Ds 5'- and 3'-end sequences. The krt8 promoter includes nucleotides 436-2674 of SEQ ID NO:1. The coding sequence for EGFP includes nucleotides 2669-3644 of SEQ ID NO:1.

TABLE 3

The Ds Construct Carrying krt8-promoter-EGFP.

CCATGGTGGCGACCGGTGCTCGACTCTAGAGGATCCCCGACATAGGGATG
AAAACGGTCGGTAACGGTCGGTAAAATACCTCTACCGTTTTCATTTTCAT
ATTTAACTTGCGGGACGGAAACGAAAACGGGATATACCGGTAACGAAAAC
GAACGGGATAAATACGGTAATCGAAAACCGATACGATCCGGTCGGGTTAA
AGTCGAAATCGGACGGGAACCGGTATTTTTGTTCGGTAAAATCACACATG
AAAACATATATTCAAAACTTAAAAACAAATATAAAAAATTGTAAACACAA
GTCTTAATTAAACATAGATAAAATCCATATAAATCTGGAGCACACATAGT
TTAATGTAGCACATAAGTGATAAGTCTTGGGCTCTTGGCTAACATAAGAA
GCCATATAAGTccctcgacctctagcttcgaattcccttcccttctactt
ttgacgtccttttaagagcttgtgcatgaaagcagatttggagctgatta
ctcatctcaaacacccatacaaagggatgattgccgtaccatgatctcac
acctttcacacctggtttatactatgatagttgtagacgattgcgtaatg
ctattaaatgcccatcagtgctggctgtgacacccaactgctgccatttc
gtgttgacttgcacgagaaatgagaaattgtctgactatgcagggtgtct
atgcgtgggaacatttatcagtggtcattaaatactatagtttacagtta
gaccaaagtgtgctgtattttgtgttagcttagctgcagttttgtgtg
tgaagtaacaaatgacaaatactcaaactattgtaattaagtagttttc
tcagaaattgtaatttactaagtagtttaaaaatgtgtacttttactttc
ccttgagtacattttagtgcagtgttggtacttttatttcacttccttc
cttcaacctgcagtcactactttatttattcttgtctatgtggattagac
aaatcagtcctgtgattcctgtccaatcaaattgcacatagaaggtaaat
cacatcataatgaactaccttaagacatgggccatttataattgcagcaa
actgtttgccagcattaaaagaagatgtcaaaaatatttacacgcattaa
cccagagactgcttagatgcatgtcactgatgagaagatgatggatgttt
actgtatgatgaccgaaataaacttaaacgcacacaagacggcacaagac
gtcaacatggcgttaggttgacgttgtaccccaacgcagtggggacgttg
catttgtttagaaatgaaaattaggttgacgtcagaactcaacgtcagg
tcgatgtcaatgttcaacatccaatctaaaatcatatatcaatgtctaat
gatgttacagcctgatgttatgcggatgttaccctatgacgtctatcag
cgttggattatggttgccatacctgatgaaataaatgtcattatttgacg
ttggtttaagatgttggttcgacattggatttttggtcgctttccaacaca
acctaaatccaccaaatattaacttcctatgacatcgttattggacgtca
aaataacaatatccttagatgctggctagactttgaatttaggtcaccac
aacctatatttaacctaatattaacatcttatgatgttgtgtgcctgctg
ggcaataactaaatgcactacagaatgttacgtttacacacatgtaaatt
acatgtaaatgcatcagcttttcacagcataatactcactacttactact
cttgagtacttttaaaaaagctacttttcactcatactttgagtaatatt TABLE 3-continued The Ds Construct Carrying krt8-promoter-EGFP.

tacaactgatactttactcgcactacattttaggcatgtattgatatt
tttactatgatttttcagtactctttccactactgcagccctccccatac
ataatcgtatgtttacacatatggtggagtttagagccataatctacatt
agctttgttagccgctagcattactgtgcagaattgtgtgtgtgcacatt
ttccaatatcaatacagaaggaaactgtgttccctgttcccttgtaaatc
tcaacaatgcaactgttcagctcaggggggaaaaatgccctgccagatcca
aacggctggcaaaagtgaatggaaaaaagccttcattaatgtgaaagtt
gctgcgcgccccacccagataaaagagcagaggttaacatgctctctac
ggctgtccagccaaccagatactgaggcagaaacacaccgctggcagat
ggtgagagctacactgtcttttccagagtttccactggaatgcctgtcct
caagtctcaagcctctccttgcattctctcattccacctggggcaaagcc
ccaggctgggtgtgacaacatttatcttaccactttctctctgtacctgt
ctaacaggtagggtgtgtgtgagagtgcgtatgtgtgcaagtgcgtgtgt
gtgtgagagcagtcagctccaccctctcaagagtgtgtataaaattggtc
agccagctgctgagagacacgcagagggactttgactctccttttgtgagc
aacctcctccactcactcctctctcagagagcactctcgtacctccttct
cagcaactcaaagacacaggatccaccggtcgccaccatggtgagcaagg
gcgaggagctgttcaccggggtggtgcccatcctggtcgagctggacggc
gacgtaaacggccacaagttcagcgtgtccggcgagggcgagggcgatgc
cacctacggcaagctgaccctgaagttcatctgcaccaccggcaagctgc
ccgtgccctggcccaccctcgtgaccaccctgacctacggcgtgcagtgc
ttcagccgctaccccgaccacatgaagcagcacgacttcttcaagtccgc
catgcccgaaggctacgtccaggagcgcaccatcttcttcaaggacgacg
gcaactacaagacccgcgccgaggtgaagttcgagggcgacaccctggtg
aaccgcatcgagctgaagggcatcgacttcaaggaggacggcaacatcct
ggggcacaagctggagtacaactacaacagccacaacgtctatatcatgg
ccgacaagcagaagaacggcatcaaggtgaacttcaagatccgccacaac
atcgaggacggcagcgtgcagctcgccgaccactaccagcagaacacccc
catcggcgacggccccgtgctgctgcccgacaaccactacctgagcaccc
agtccgccctgagcaaagaccccaacgagaagcgcgatcacatggtcctg
ctggagttcgtgaccgccgcgggatcactctcggcatggacgagctgta
caagtaaagcggccgcgactctagatcataatcagccataccacatttgt
agaggttctacttgcttaaaaaacctcccacacctcccctgaacctga
aacataaaatgaatgcaattgttgttgttaacttgtttattgcagcttat
aatggttacaaataaagcaatagcatcacaaatttcacaaataaagcatt
ttttcactgcattctagttgtggtttgtccaaactcatcaatggtcgag
ggatctgTTGCAGTCATCCCGAATTAGAAAATACGGTAACGAAACGGGAT
CATCCCGATTAAAAACGGGATCCCGGTGAAACGGTCGGGAAACTAGCTCT
ACCGTTTCCGTTTCCGTTTACCGTTTTGTATATCCCGTTTCCGTTCCGTT

TABLE 3-continued

The Ds Construct Carrying krt8-promoter-EGFP.

TTCGTTTTTTACCTCGGGTTCGAAATCGATCGGGATAAAACTAACAAAAT

CGGTTATACGATAACGGTCGGTACGGGATTTTCCCATCCTACTTTCATCC

CTGCGTCGGGTATCGAGCTCGAATTAAGCTTGATATCGAATTCCTGCAGG

AAAAAAAAACAATTAGAATTAATTTTATATTTATACAATTTATGGTGC
(SEQ ID NO: 1)

Example 3

Co-Injection of Ds Donor Construct with TPase mRNA Causes Specific Ds Excision

In vitro transcribed, capped and polyadenylated TPase mRNA was microinjected together with the non-linearized Ds donor plasmid, into zebrafish embryos at the one-cell stage. The embryos were incubated for 10 hours at 28° C. and the genomic DNA was analyzed by excision PCR with primers flanking the Ds sequence (see methods for description). The excision products were detected only in the embryos injected with both the TPase mRNA ($NLS^{K5E}$-TPase or NoNLS-TPase) and the Ds construct, whereas the control embryos injected with the Ds construct alone produced no PCR fragments of the expected lengths (FIG. 2A). Surprisingly the NLS-TPase failed to produce Ds excision products in contrast to the $NLS^{K5E}$-TPase that produced the highest yield. The NoNLS-TPase required 5 times more RNA to induce excision at a level similar to the $NLS^{K5E}$-TPase. Based on these preliminary excision data the $NLS^{K5E}$-TPase was selected as the most productive, and it was used in the majority of the experiments. The TPase-mediated excision of the Ds element from its donor site was further confirmed by nucleotide sequencing of the PCR-amplified excision derivatives. Analysis of these sequences revealed that excision occurred specifically at the Ds-termini consistent with transposition. Since excision PCR products were expected to contain a mixture of various excision-repair events, we anticipated mixed sequencing patterns beginning at the junction of the Ds and the adjacent vector. However, dominant sequence patterns were observed in products from two vectors with different Ds flanking sequence, indicative of preferential excision (FIG. 2B). The predominant excision footprints involved deletion of a flanking nucleotide immediately adjacent to one Ds-end accompanied by change or deletion of a flanking nucleotide at the other Ds-end.

Example 4

Nuclear Localization Signals Affect

Intracellular Localization of Ac TPase and Aggregation

Figure 3:
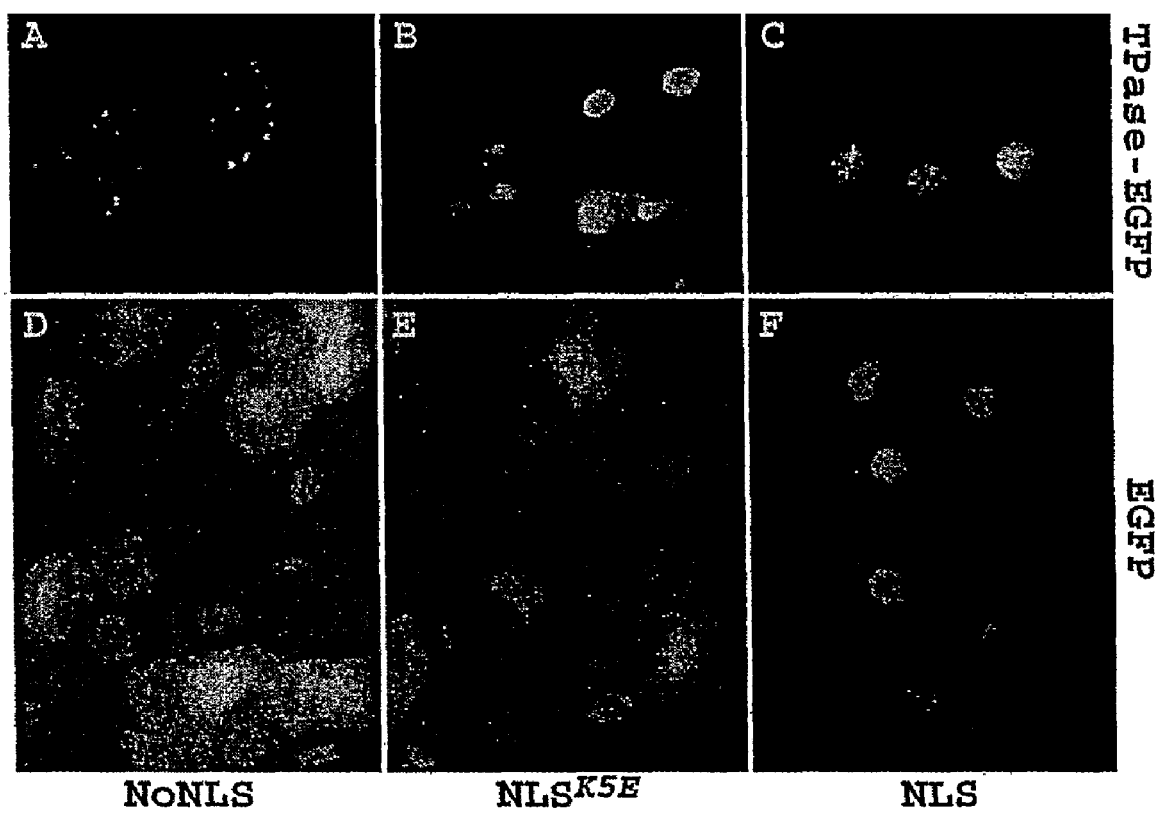
FIGS. 3A-3F show the effects of different NLS sequences on the intracellular localization of TPase.

To investigate the effects of different NLSs on intracellular localization, krt8:TPase-EGFP fusion constructs for all three TPases (NoNLS-, NLS- and $NLS^{K5E}$-TPase) were produced. Promoter krt8 drives expression into single layer of epithelial tissue that consists of large and flat cells that are very convenient model to observe cellular localization. These constructs were injected into zebrafish embryo at 1 cell stage and GFP fluorescence was observed at 24 hpf stage. High level of expression of any of the three TPase constructs was toxic to the embryos. Injection of 15 pg of plasmid caused over 50% lethality during the first 24 hours of development and the surviving embryos were mostly devoid of krt8-specific GFP expression. Injection of 3 pg of plasmid produced mainly GFP-negative embryos. We assumed that expression of high (easily visible by GFP fluorescence) amount of the TPase fusion proteins was toxic for the cells. Nevertheless, in each case we found a small proportion of GFP-positive cells that retained their epithelial shape, thus allowing the identification of the intracellular localization of the GFP-tagged TPase therein (FIGS. 3A-3C). The NoNLS-TPase-EGFP was found to localize mainly to the cytoplasm, whereas NLS-TPase-EGFP and $NLS^{K5E}$-TPase-EGFP were predominantly nuclear. The NoNLS-TPase-EGFP and NLS-TPase-EGFP showed a strong tendency to form aggregates in the cytoplasm and nucleus respectively (FIGS. 3A-3C), that resembled the Activator TPase aggregates reported in plants (Boehm et al., 1995; Heinlein et al., 1994). On the contrary, the $NLS^{K5E}$ rarely gave rise to aggregates even at visibly higher expression levels. To confirm that both NLS and $NLS^{K5E}$ are functional in zebrafish cells, we analyzed subcellular localization of NLS-EGFP and $NLS^{K5E}$-EGFP fusion proteins in the similar experiments (FIGS. 3D-3F). We observed a gradual increase in the nucleus to cytoplasm ratio in the distribution of NoNLS-EGFP, $NLS^{K5E}$-EGFP and NLS-EGFP respectively.

Example 5

Modified Ac Transposase Induces High Rates of Germinal Ds Insertions That Require Nuclear Localization The injected embryos were raised to adulthood and outcrossed to the wt fish. We made absolutely no selection based on intensity and/or abundance of the GFP signal in the injected embryos: all the injected embryos were raised regardless of their GFP expression. Approximately 60% of the founders ($F_0$) injected with NLS-TPase or $NLS^{K5E}$-TPase produced offspring ($F_1$) containing GFP-fluorescent embryos (Table 4). The ratios of EGFP-positive embryos among the progeny was also striking: 10% of positive founders produced progenies containing more than 50% of GFP-positives with multiple expression patterns including one $F_0$ fish which produced 100% GFP-positive progeny. The ratios were counted at 4 dpf to avoid possible maternal expression (Parinov et al., 2004). This was also considered as an indication of high transposition activity and it also suggested that Ac/Ds transposition probably occurred early in development. Founders injected with NoNLS-TPase produced significantly lower transgenesis rate. We did not observe any GFP-positive offspring in the control population injected with the Ds construct alone (integration of circular DNA being ineffective in zebrafish).

TABLE 4

Transgenesis Efficiencies of Different TPase Constructs.

|  | No NLS | $NLS^{K5E}$ | NLS |
| --- | --- | --- | --- |
| $F_0$ screened: | 26 | 91 | 20 |
| $F_0$ producing GFP-positive $F_1$: | 2 | 52 | 12 |
| Transgenesis rate: | 8% | 57% | 60% |
| Highest $F_1$ GFP ratio: | 14/67 (21%) | 133/138 (96%) | 250/250 (100%) |

Transgenesis rates are calculated as percent of founders producing GFP-positive offspring among the total number of screened founders. The last row shows the highest ratios of GFP-positive embryos among the $F_1$ progenies.

Example 6

Integration of Dissociation Element into Zebrafish Genome

We isolated DNA sequences flanking Ds insertions in the $F_1$ fish using thermal asymmetric interlaced PCR "TAIL-PCR" (Liu and Whittier, 1995). Twenty-eight nonredundant flanking sequences thus obtained perfectly matched zebrafish nucleotide sequences from GenBank or Ensembl databases. The match in each instance started from the first nucleotide adjacent to Ds 5'- or 3'-termini. Moreover, Ds insertions were flanked by the classic 8 bp direct duplication of the target site, typically accompanying Ac/Ds insertions in plants and other hAT transposons (FIG. 2C). Therefore, Ds integrated into the zebrafish genome through a specific TPase-mediated transposition mechanism. In a few $F_1$ fish, we isolated flanking sequences corresponding to the original Ds donor vector that were, however, accompanied by additional non-vector flanking sequence in the same $F_1$ fish. Twenty-one out of twenty eight identified Ds insertion sites were found within genes, suggestive of a potential preference for actively transcribed regions.

Figure 4:
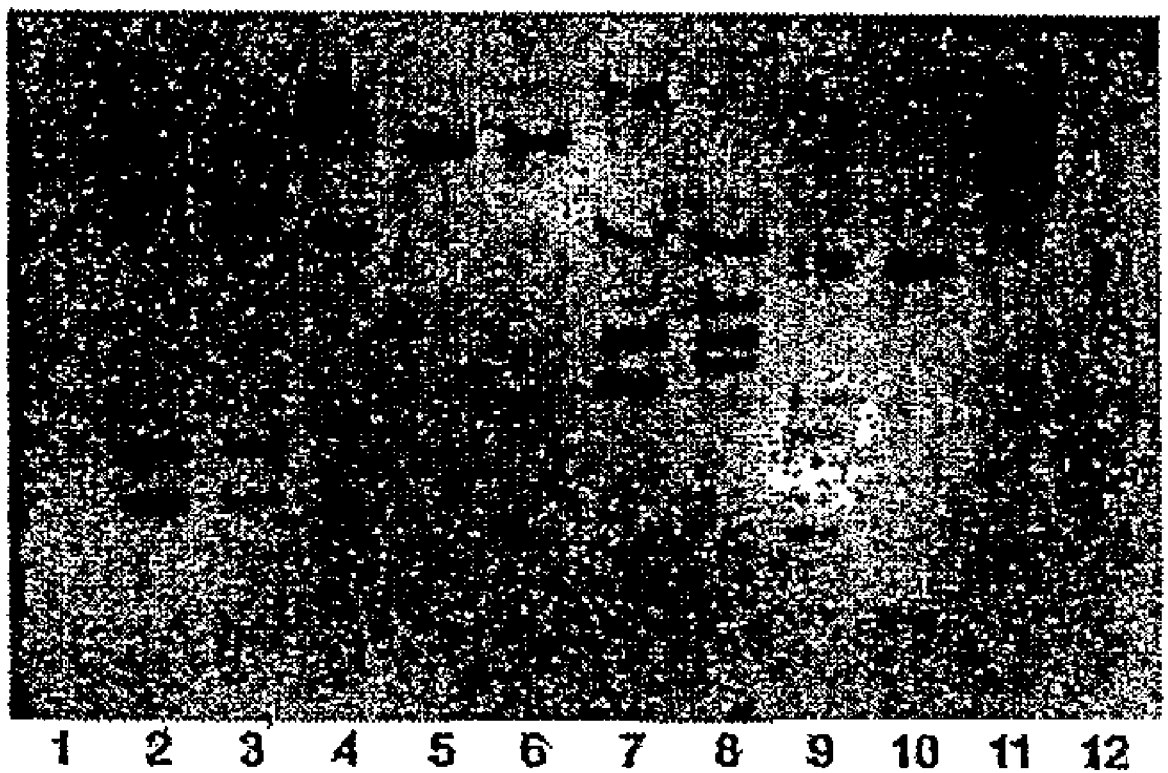
FIG. 4 shows evaluation of the Ds copy number in F$_1$ fish. Individual F$_1$ fish were out-crossed to the wt and DNA from 12 randomly selected GFP-positive embryos was used for Southern blot analysis. The DNA samples were digested with EcoRI (the Ds construct contains a single EcoRI site) and hybridized with DIG-labeled probe for the EGFP sequence. (Lane 1-4) progenies of four different F$_1$ fish from the same family (from the same founder F$_0$); (Lanes 5-11) progenies of F$_1$ fish from different families (originated from different F$_0$ founders), (Lane 2) GFP negative control.

Southern blot hybridization with EGFP-specific probe revealed predominantly multiple insertions in different $F_1$ progeny (FIG. 4). The copy number ranged from 1 to 7 or more insertions per $F_1$ fish with an average of 4 insertions per genome. Different $F_1$ progeny from the same family (descendents from the same $F_0$ founder) often carried different independent insertions (FIG. 4, lanes 1-4).

Such an unusually high frequency of germline transposition suggests, firstly, that original host factors are dispensable and, secondly, that the new host environment does not suppress Ds transposition.

Example 7

Transposition of the Genomic Ds Elements

Figure 5:
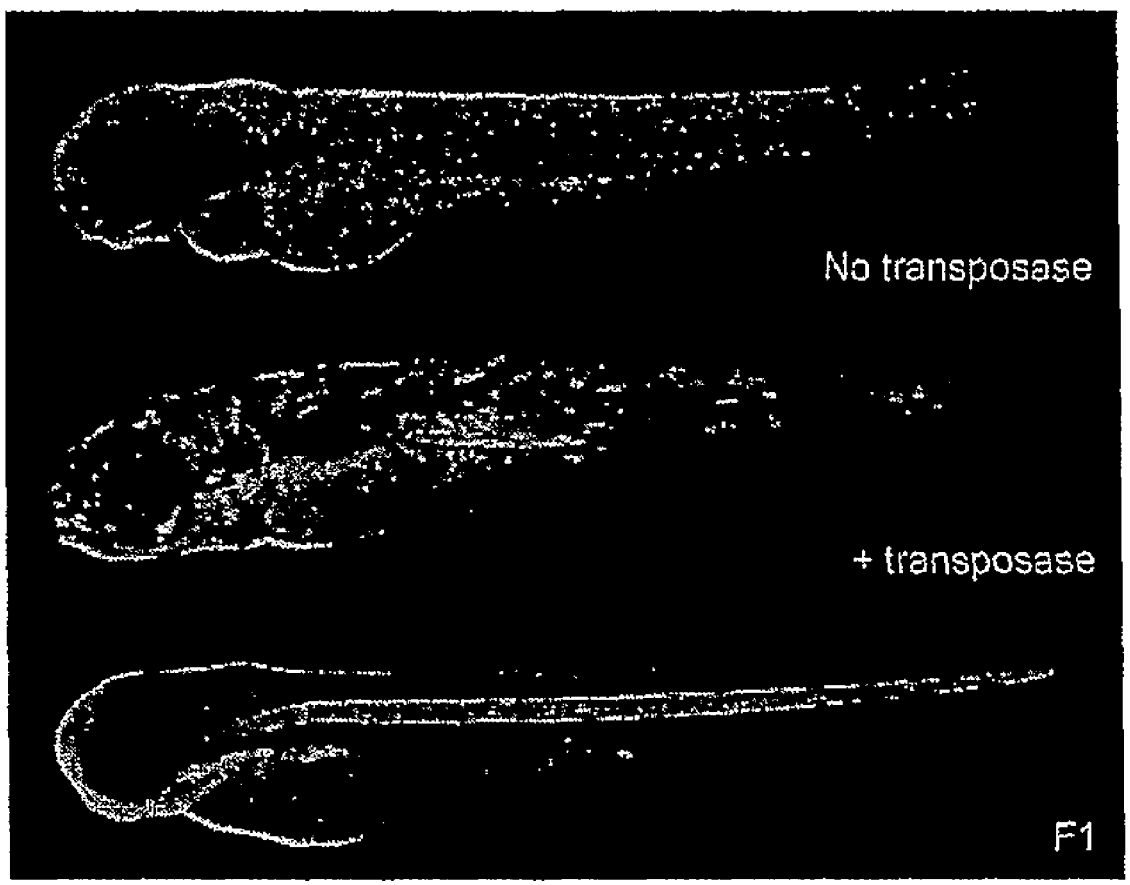
FIG. 5 shows transposition of genomic Ds insertions. Top: mock-injected transgenic fish with a single Ds insertion in genome exhibiting even and weak GFP expression pattern in the skin epithelia and the gut. Middle: a representative example of a fish carrying the same Ds insertion injected with TPase RNA demonstrating ectopic GFP expression in the brain, spinal chord, ears, muscles, gonadal region, and variegating mosaic expression in the skin (presumably due to increased number of copies). Bottom: Example of a novel expression pattern found among F$_1$ generation—expression in notochord is not present in the control; moreover the dotted pattern on the skin of the control fish is not present in the $F_1$ fish indicating that the donor Ds copy is lost during transposition.

To further validate transposition activity of the Ac/Ds, we remobilized the genomic Ds insertions by injecting TPase mRNA into the embryos of the transgenic fish carrying a single Ds insertion showing EGFP expression in the skin epithelia and the gut (FIG. 5). Over 90% of the embryos injected with NLS-TPase (80 out of 85) and $NLS^{K5E}$-TPase (69 out of 72) exhibited ectopic EGFP expression in various organs including brain, spinal chord, muscles, heart, liver, gonadal region etc. (FIG. 5). Ectopic expression of the EGFP reporter could be attributed to the enhancer-trap effect created as a consequence of the successful re-insertion of the excised Ds copy in each instance. No such effect was observed in the mock-injected control embryos. For mock injections we used RNA of Tol2 transposase (Kaeakanii et al., 2000) that apparently does not recognize the Ds sequence. Interestingly, injection of NoNLS-TPase caused a much lower rate of ectopic GFP expression (9 out of 168 injected embryos) compared to NLS-TPase and $NLS^{K5E}$-TPase. The novel patterns induced by NoNLS-TPase were simpler, usually affecting only a single cluster of same cell type. This experiment is additional supporting evidence that TPase required nuclear localization for genomic transposition. The embryos injected with $NLS^{K5E}$-TPase were raised to maturity and out-crossed to wt fish. We found $F_1$ embryos with novel expression patterns among the progenies of 10 out of 13 screened founders (77%) (FIG. 5 and Table 5). Note that the real number of transpositions should be higher since we only detected the insertions that generated new distinguishable patterns. Sequences amplified from the $F_1$ embryos carrying such new expression patterns revealed novel Ds insertion sites that were not present in the original fish line. Hence, the modified Ac transposase is clearly capable of effectively transposing not only the Ds carried by the vector construct supplied via pan-embryonic injection, but also the Ds elements stably integrated into zebrafish nuclear genome. In addition to the unusually high re-insertion rate we observed frequently altered GFP segregation ratios (Table 5). One out of the thirteen founders produced GFP segregation ratio significantly higher than 1:1 (the expected ratio for an outcross of a single allele heterozygous parent) manifesting the increase of Ds copy number. Five out of thirteen founders demonstrated GFP segregation significantly lower than 1:1 indicative of a loss of the donor Ds. Altogether in 11 out of 13 (85%) screened founders we were able to detect the TPase activity by observing the presence of novel GFP expression pattern or/and by altered segregation ratio.

TABLE 5

Re-Transposition and Loss of Ds Donor in the Transgenic Line Injected with RNA

| $F_0$ fish | GFP+/GFP− | New GFP patterns | GFP segregation |
|---|---|---|---|
| 1 | 144/151 | — | |
| 2 | 70/78 | +1 | |
| 3 | 118/130 | +1 | |
| 4 | 175/93 | +3 | Ds copies increase |
| 5 | 120/187 | +2 | loss of Ds |
| 6 | 55/314 | — | loss of Ds |
| 7 | 56/170 | +1 | loss of Ds |
| 8 | 41/122 | +1 | loss of Ds |
| 9 | 225/201 | +1 | |
| 10 | 74/253 | +2 | loss of Ds |
| 11 | 165/172 | — | |
| 12 | 126/124 | +2 | |
| 13 | 153/134 | +1 | |

Transgenic embryos carrying a single heterozygous Ds insert were injected with $NLS^{K5E}$-TPase, raised to maturity and out-crossed to wild type fish. In $F_1$ generation we observed the occurrence of novel expression patterns and altered GFP segregation.

Example 8

Ds Transposition of Human Embryonic Kidney Cell Line

We have also demonstrated Ds transposition in human cells. We utilized a different strategy compared to the one used in fish. Instead of a messenger RNA encoding a modified Ac transposase we used a plasmid DNA construct containing ORF of the modified $NLS^{K5E}$-Ac transposase under the CMV promoter. The Ds construct was also different: The Ds element carried EGFP gene under the CMV promoter, it also contained a blasticidin-resistance gene (BSD) and internal plasmid replication origin. Two plasmids were co-transfected into human embryonic kidney cell line HEK293, selected on blasticidin. The cells were harvested and their DNAs were analyzed by TAIL-PCR and sequencing for the presence of TPase-mediated Ds integrations in the human genome. We have successfully obtained such flanking sequences that perfectly matched human nucleotide sequences starting from the first nucleotide immediately adjacent to Ds 5'- or 3'-termini (FIG. 6). Moreover, in one case the Ds insertions were flanked by the classic 8 bp direct duplication of the target site, typically accompanying hAT transposons. Therefore, intracellular environment of human cells is also suitable for the Ds transposition.

Materials and Methods

Transfection of Ac/Ds into HEK293 Cell Line

1) $2.5 \times 10^5$ HEK293 (ATCC# CRL-1573) cells per 6-well plate were seeded 24 hours before transfection in 2 ml DMEM/10% FBS at 5% $CO_2$.

2) Cells were co-transfected with 0.5 mg each plasmid (pDs-CMV-EGFP-Ub-Bsd and pCMV-Ac). The GenePorter2 transfection reagent (GTS, CA, USA; Cat. #T202096) was used for transfection according to the recommended protocol.

3) 24 hours after transfection, single-cell diluted cells were seeded in 96-well plate in DMEM/10% FBS containing 10 mg/ml Blasticidin (Invitrogene; #R210-01). The antibiotic selection of resistant to antibiotic colonies was continued during 6 days. After selection, the media was changed to DMEM/10% FBS and GFP positive colonies continue grow till confluence in 6-well plate.

4) DNA from the cells was obtained using phenol/chloroform extraction followed by ethanol precipitation.

5) Flanking sequences were obtained by TAIL-PCR.

Constructs Used in Human Embryonic Kidney Cell Line

Ds Construct (pDS-CMV-EGFP-Ub-Bsd) (SEQ ID NO: 70)

bp 1-292, Ds 5'-end cis-required sequence:

(SEQ ID NO: 45)
CAGGGATGAAAGTAGGATGGGAAAATCCCGTACCGACCGTTATCGTATAA

CCGATTTTGTTAGTTTTATCCCGATCGATTTCGAACCCGAGGTAAAAAAC

GAAAACGGAACGGAAACGGGATATACAAAACGGTAAACGGAAACGGAAAC

GGTAGAGCTAGTTTCCCGACCGTTTCACCGGGATCCCGTTTTTAATCGGG

ATGATCCCGTTTCGTTACCGTATTTTCTAATTCGGGATGACTGCAACAGA

TCCCTCGAGCGCTTAAGTTTAAACGCGTTAACAATTGGCCAT bp 293-1687, pEGFP-N3 plasmid fragment (bp 9-1403) containing pCMV-EGFP:

(SEQ ID NO: 46)
AATAGTAATCAATTACGGGGTCATTAGTTCATAGCCCATATATGGAGTTC

CGCGTTACATAACTTACGGTAAATGGCCCGCCTGGCTGACCGCCCAACGA

CCCCCGCCCATTGACGTCAATAATGACGTATGTTCCCATAGTAACGCCAA

TAGGGACTTTCCATTGACGTCAATGGGTGGAGTATTTACCGTAAACTGCC

CACTTGGCACTACATCAAGTGTATCATATGCCAAGTACGCCCCCTATTGA

CGTCAATGACGGTAAATGGCCCGCCTGGCATTATGCCCAGTACATGACCT

TATGGGACTTTCCTACTTGGCAGTACATCTACGTATTAGTCATCGCTATT

ACCATGGTGATGCGGTTTTGGCAGTACATCAATGGGCGTGGATAGCGGTT

TGACTCACGGGGATTTCCAAGTCTCCACCCGATTGACGTCAATGGGAGTT

TGTTTTGGCACCAAAATCAACGGGACTTTCCAAAATGTCGTAACAACTCC

GCCCCATTGACCCAAATGGGCGGTAGGCGTGTACGGTGGGAGGTCTATAT

AAGCAGAGCTGGTTTAGTGAACCGTCAGATCCGCTAGCGCTACCGGAGTC

AGATCTCGAGCTCAAGCTTCGAATTCTGCAGTCGACGGTACCGCGGGCCC

GGGATCCATCGCCACCATGGTGAGCAAGGGCGAGGAGCTGTTCACCGGGG

TGGTGCCCATCCTGGTCGAGCTGGACGGCGACGTAAACGGCCACAAGTTC

AGCGTGTCCGGCGAGGGCGACGGCGATGCCACCTAGGGCAAGCTGACCCT

GAAGTTCATCTGCACCACCGGCAAGCTGCCCGTGCCCTGGCCCACCCTCG

TGACCACCCTGACCTACGGCGTGCAGTGCTTCAGCCGCTACCCCGACCAC

ATGAAGCAGCACGACTTCTTCAAGTCCGCCATGCCCGAAGGCTACGTCCA

GGAGCGCACCATCTTCTTCAAGGACGACGGCAACTACAAGACCCGCGCCG

ACGTGAAGTTCGAGGCCGACACCCTGGTGAACCGCATCGAGCTGAAGGGC

ATCGACTTCAAGGAGGACGGCAACATCCTGGGGCACAAGCTGGAGTACAA

CTACAACAGCCACAACGTCTATATCATGGCCGACAAGCAGAAGAACGGCA

TCAAGGTGAACTTCAAGATCCGCCACAACATCGAGGACGGCAGCGTGCAG

CTCGCCGACCACTACCAGCAGAACACCCCCATCGGCGACGGCCCCGTGCT

GCTGCCCGACAACCACTACCTGAGCACCCAGTCCGCCCTGAGCAAAGACC

CCAACGAGAAGCGCGATCACATGGTCCTGCTGGAGTTCGTGACCGCCGCC

GGGATCACTCTCGGCATGGACGAGCTGTACAAGTAAAGCGGCCGC bp 1688-3403, pUBBSD1 plasmid fragment (bp 1917-3632) containing blasticidin-resistance gene (BSD):

(SEQ ID NO: 47)
GATATCGCTAGCTCGAGATCGGGAGATCTGGCCTCCGCGCCGGGTTTTGG

CGCCCCCCGCGGGCGCCCCCTCCTCACGGCGAGCGCTGCCACGTCAGACG

AAGGGCGCACGAGGGTCCTGATCCTTCCGCCCGGACGCTCAGGACAGCGG

CCCGCTGCTCATAAGACTCCGCCTTAGAACCCCAGTATCAGCAGAAGGAC

ATTTTAGGACGGGACTTGGGTGACTCTAGGGCACTGGTTTTCTTTCCAGA

GAGCGGAACAGGCGAGGAAAAGTAGTCCCTTCTCGGCGATTCTGCGGAGG

GATCTCCGTCGGGCGGTGAACGCCGATGATTATATAAGGACGCGCCGGGT

GTGGCACAGCTAGTTCCGTCGCAGCCGGGATTTGGGTCGCGGTTCTTGTT

TGTGGATCGCTGTGATCGTCACTTGGTGAGTAGCGGGCTGCTGGGCTGGC

CGGGGCTTTCGTGGCCGCCCGGCCGCTCGGTGGGACGGAAGCGTGTGGAG

AGACCGCCAAGGGCTGTAGTCTGGGTCCGCGAGCAAGGTTGCCCTGAACT

GGGGGGTTGGGGGGAGCGCAGCAAAATGGCGGCTGTTCCCGAGTCTTGAAT

GGAAGACGCTTGTGAGGCGGGCTGTGAGGTCGTTGAAACAAGGTGGGGGG

CATGGTGGGCGCCAAGAACCCAAGGTCTTGAGGCCTTCGCTAATGCGGGA

AAGCTCTTATTCGGGTGAGATGGGCTGGGGCACCATCTGGGGACCCTGAC

GTGAAGTTTGTCACTGACTGGAGAACTCGGTTTGTCGTCTGTTGCGGGGG

CGGCAGTTATGGCGGTGCCGTTGGGCAGTGCACCCGTACCTTTGGGAGCG

CGCGCCCTCGTCGTGTCGTGACGTCACCCGTTCTGTTGGCTTATAATGCA

GGGTGGGGCCACCTGCCGGTAGGTGTGCGGTAGGCTTTTCTCCGTCGCAG

GACGCAGGGTTCGGGCCTAGGGTAGGCTCTCCTGAATCGACAGGCGCCGG

ACCTCTGGTGAGGGAGGGATAAGTGAGGCGTCAGTTTCTTTGGTCGGTT

TTATGTACCTATCTTCTTAAGTAGCTGAAGCTCCGGTTTTGAACTATGCG

CTCGGGGTTGGCGAGTGTGTTTTGTGAAGTTTTTTAGGCACCTTTTGAAA

TGTAATCATTTGGGTCAATATGTAATTTTCAGTGTTAGACTAGTAAATTG

TCCGCTAAATTCTGGCCGTTTTTGGCTTTTTTGTTAGACCGGACCGTGTT

GACAATTAATCATCGGCATAGTATATCGGCATAGTATAATACGACAAGGT

GAGGAACTAAACCATGGCCAAGCCTTTGTCTCAAGAAGAATCCACCCTCA

TTGAAAGAGCAACGGCTACAATCAACAGCATCCCCATCTCTGAAGACTAC

AGCGTCGCCAGCGCAGCTCTCTCTAGCGACGGCCGCATCTTCACTGGTGT

CAATGTATATCATTTTACTGGGGGACCTTGTGCAGAACTCGTGGTGCTGG

GCACTGCTGCTGCTGCGGCAGCTGGCAACCTGACTTGTATCGTCGCGATC

GGAAATGAGAACAGGGGCATCTTGACCCCCTGCGGACGGTGCCGACAGGT

GCTTCTCGATCTGCATCCTGGGATCAAAGCCATAGTGAAGGACAGTGATG

GACAGCCGACGGCAGTTGGGATTCGTGAATTGCTGCCCTCTGGTTATGTG

TCGGAGGGCTAAGCAC bp 3404-4465, cloning vector fragment containing plasmid replication origin:

(SEQ ID NO: 48)
TTCGTGGCCGAGGAGCAGGACTGACACTCGACCTCGAAACTTGTTTATTG

CAGCTTATAATGGTTACAAATAAAGCAATAGCATCACAAATTTCACAAAT

AAAGCATTTTTTTCACTGCATTCTAGTTGTGGTTTGTCCAAACTCATCAA

TGTATCTTATCATGTCTGAATTCCCGGGGATCCTCTAGACTGTCAGACCA

AGTTTACTCATATATACTTTAGATTGATTTAAAACTTCATTTTTAATTTA

AAAGGATCTAGGTGAAGATCCTTTTTGATAATCTCATGACCAAAATCCCT

TAACGTGAGTTTTCGTTCGACTGAGCGTCAGACCCCGTAGAAAAGATCAA

AGGATCTTCTTGAGATCCTTTTTTTCTGCGCGTAATCTGCTGCTTGCAAA

CAAAAAAACCACCGCTACCAGCGGTGGTTTGTTTGCCGGATCAAGAGCTA

CCAACTCTTTTTCCGAAGGTAACTGGCTTCAGCAGAGCGCAGATACCAAA

TACTGTTCTTCTAGTGTAGCCGTAGTTAGGCCACCACTTCAAGAACTCTG

TAGCACCGCCTACATACCTCGCTCTGCTAATCCTGTTACCAGTGGCTGCT

GCCAGTGGCGATAAGTCGTGTCTTACCGGGTTGGACTCAAGACGATAGTT

ACCGGATAAGGCGCAGCGGTCGGGCTGAACGGGGGGTTCGTGCACACAGC

CCAGCTTGGAGCGAACGACCTACACCGAACTGAGATACCTACAGCGTGAG

CTATGAGAAAGCGCCACGCTTCCCGAAGGGAGAAAGGCGGACAGGTATCC

GGTAAGCGGCAGGGTCGGAACAGGAGAGCGCACGAGGGAGCTTCCAGGGG

GAAACGCCTGGTATCTTTATAGTCCTGTCGGGTTTCGCCACCTCTGACTT

GAGCGTCGATTTTTGTGATGCTCGTCAGGGGCGGAGCCTATGGAAAAA

CGCCAGCAACGCGGCCTTTTTACGGTTCCCGCCCTTTTGCTGGCCTTTTG

CTCACATGCTGGGCCCAGCCGGCCAGATCTGAGCTCGCGGCCGCGATATC

GCTAGCTCGAGG bp 4466-4835, Ds 3'-end cis-required sequence:

(SEQ ID NO: 49)
GACTTATATGGCTTCTTATGTTAGCCAAGAGCCCAAGACTTATCACTTAT

GTGCTACATTAAACTATGTGTGCTCCAGATTTATATGGATTTTATCTATG

TTTAATTAAGACTTGTGTTTACAATTTTTTATATTTGTTTTTAAGTTTTG

AATATATGTTTTCATGTGTGATTTTACCGAACAAAAATACCGGTTCCCGT

CCGATTTCGACTTTAACCCGACCGGATCGTATCGGTTTTCGATTACCGTA

TTTATCCCGTTCGTTTTCGTTACCGGTATATCCCGTTTTCGTTTCCGTCC

CGCAAGTTAAATATGAAAATGAAAACGGTAGAGGTATTTTACCGACCGTT

ACCGACCGTTTTCATCCCTA bp 4836-6495, cloning vector fragment containing ampicillin resistance gene:

(SEQ ID NO: 50)
TGCATTCTGACAGTTACCAATGCTTAATCAGTGAGGCACCTATCTCAGCG

ATCTGTCTATTTCGTTCATCCATAGTTGCCTGACTCCCCGTCGTGTAGAT

AACTACGATACGGGAGGGCTTACCATCTGGCCCCAGTGCTGCAATGATAC

CGCGAGACCCACGCTCACCGGCTCCAGATTTATCAGCAATAAACCAGCCA

GCCGGAAGGGCCCAGCGCAGAAGTGGTCCTGCAACTTTATCCGCCTCCAT

CCAGTCTATTAATTGTTGCCGGGAAGCTAGAGTAAGTAGTTCGCCAGTTA

ATAGTTTGCGCAACGTTGTTGCCATTGCTACAGGCATCGTGGTGTCACGC

TCGTCGTTTGGTATGGCTTCATTCAGCTCCGGTTCCCAACGATCAAGGCG

AGTTACATGATCCCCCATGTTGTGCAAAAAAGCGGTTAGCTCCTTCGGTC

CTCCGATCGTTGTCAGAAGTAAGTTGGCCGCAGTGTTATCACTCATGGTT

ATGGCAGCACTGCATAATTCTCTTACTGTCATGCCATCCGTAAGATGCTT

TTCTGTGACTGGTGAGTACTCAACCAAGTCATTCTGAGAATAGTGTATGC

GGCGACCGAGTTGCTCTTGCCCGGCGTCAATACGGGATAATACCGCGCCA

CATAGCAGAACTTTAAAAGTGCTCATCATTGGAAAACGTTCTTCGGGGCG

AAAACTCTCAAGGATCTTACCGCTGTTGAGATCCAGTTCGATGTAACCCA

CTCGTGCACCCAACTGATCTTCAGCATCTTTTACTTTCACCAGCGTTTCT

GGGTGAGCAAAAACAGGAAGGCAAAATGCCGCAAAAAAGGGAATAAGGGC

GACACGGAAATGTTGAATACTCATACTCTTCCTTTTTCAATATAATTGAA

GCATTTATCAGGGTTATTGTCTCATGAGCGGATACATATTTGAATGTATT

TAGAAAAATAAACAAATAGGGGTTCCGCGCACATTTCCCCGAAAAGTGCC

ACCTAAATTGTAAGCGTTAATATTTTGTTAAAATTCGCGTTAAATTTTTG

TTAAATCAGCTCATTTTTTAACCAATAGGCCGAAATCGGCAAAATCCCTT

ATAAATCAAAAGAATAGACCGAGATAGGGTTGAGTGTTGTTCCAGTTTGG

AACAAGAGTCCACTATTAAAGAACGTGGACTCCAACGTCAAAGGGCGAAA

AACCGTCTATCAGGGCGATGGCCCACTACGTGAACCATCACCCTAATCAA

GTTTTTTGGGGTCGAGGTGCCGTAAAGCACTAAATCGGAACCCTAAAGGG

AGCCCCCGATTTAGAGCTTGACGGGGAAAGCCGGCGAACGTGGCGAGAAA

GGAAGGGAAGAAAGCGAAAGGAGCGGGCGCTAGGGCGCTGGCAAGTGTAG

CGGTCACGCTGCGCGTAACCACCACACCCGCCGCGCTTAATGCGCCGCTA

CAGGGCGCGTCCCATTCGCCATTCAGGCTGCGCAACTGTTGGGAAGGGCG

ATCGGTGCGGGCCTCTTCGCTATTACGCCAGCTGGCGAAAGGGGGATGTG

CTGCAAGGCGATTAAGTTGGGTAACGCCAGGGTTTTCCCAGTCACGACGT

TGTAAAACGACGGCCAGTGAATTGATACGACTCACTATAGGGCGAATTGG

GTACCCGACG

Ac-TPase Construct CA-Ac) (SEQ ID NO: 71)

DNA construct carrying NLS$^{K5E}$-TPase ORF under CMV promoter was made by cloning the PCR amplified NLS$^{K5E}$-TPase fragments using primers: Ac5Bam: gcgcGGATCCatacgatttaggtgacactatag (SEQ ID NO:51) and Ac3Not: cgatcgatgcGGCCgCCTT GGCTAACATAAGAAG (SEQ ID NO:52) into BamHI and NotI restriction sites of the pEGFP-N1 construct.

bp 1-665, pEGFP-N1 plasmid fragment (bp 1-665) containing promoter CMV:

(SEQ ID NO: 53)
tagttattaatagtaatcaattacggggtcattagttcatagcccatata tggagttccgcgttacataacttacggtaaatggcccgcctggctgaccg cccaacgaccccgcccattgacgtcaataatgacgtatgttcccatagt aacgccaatagggactttccattgacgtcaatgggtggagtatttacggt aaactgcccacttggcagtacatcaagtgtatcatatgccaagtacgccc cctattgacgtcaatgacggtaaatggcccgcctggcattatgcccagta catgaccttatgggactttcctacttggcagtacatctacgtattagtca tcgctattaccatggtgatgcggttttggcagtacatcaatgggcgtgga tagcggtttgactcacggggatttccaagtctccaccccattgacgtcaa tgggagtttgttttggcaccaaaatcaacgggactttccaaaatgtcgta acaactccgcccattgacgcaaatgggcggtaggcgtgtacggtgggag gtctatataagcagagctggtttagtgaaccgtcagatccgctagcgcta ccggactcagatctcgagctcaagcttcgaattctgcagtcgacggtacc gcgggcccgggatcc bp 665-3066, amplified fragment containing NLS$^{K5E}$-TPase ORF sequence:

(SEQ ID NO: 54)
atacgatttaggtgacactatagaatacaagcttgcttgttcttttttgca gaagctcagaataaacgctcaactttggcagatccGCCACCATGGGTCCT

CCAGAGAAGAAGCGTAAGGTAGAAATGGCTATTGTTCATGAACCACAACC

ACAACCACAACCACAACCAGAACCACAACCACAGCCACAACCTGAACCCG

AAGAAGAAGCACCACAGAAGAGGGCAAAGAAGTGCACATCGGATGTATGG

CAGCATTTCACCAAGAAGGAAATTGAAGTGGAGGTCGATGGAAAGAAATA

CGTTCAGGTATGGGGGCATTGCAACTTTCCTAATTGCAAGGCTAAGTATA

GGGCTGAGGGTCATCATGGAACAAGCGGATTTCGAAATCACTTGAGAACA

TCACATAGTTTAGTTAAAGGTCAGTTGTGTCTAAAAAGTGAAAAGGATCA

TGGCAAAGACATAAATCTCATTGAGCCTTATAAGTACGATGAAGTGGTTA

GCCTAAAGAAGCTTCATTTGGCAATAATCATGCATGAATACCCTTTCAAT

ATTGTAGAACATGAGTACTTTGTTGAGTTTGTTAAGTCTCTGCGCCCTCA

CTTTCCAATAAAGTCCCGTGTCACTGCTAGAAAATATATCATGGATTTGT

ATTTGGAAGAAAAGAAAAGTTGTATGGAAAACTAAAAGATGTTCAGTCT

CGCTTCAGTACAACTATGGATATGTGGACATCTTGTCAAAATAAGTCATA

CATGTGTGTCACCATCCATTGGATTGATGATGATTGGTGTCTCCAAAAAA

GAATTGTTGGCTTTTTTCATGTTGAAGGGCGCCACACTGGCCAAAGGTTA

TCACAAACCTTCACTGCAATCATGGTTAAGTGGAACATTGAGAAAAAATT

GTTTGCCTTGTCTTTGGATAATGCTAGTGCAAATGAAGTAGCTGTGCACG

ATATAATTGAGGATTTGCAGGACACTGATTCAAATCTAGTTTGTGATGGT

GCTTTCTTTCATGTGAGGTGTGCTTGTCACATACTGAACTTGGTTGCAAA

GGATGGCTTGGCTGTAATTGCAGGAACAATTGAGAAAATCAAAGCGATTG

TTCTTGCTGTAAAATCTTCTGCTTTGCAGTGGGAAGAACTAATGAAGTGT

GCTAGTGAATGTGACTTGGATAAATCTAAAGGGATCTCATATGATGTCTC

AACTAGATCGAATTCAACCTATTTGATGTTGAGGGATGCCTTATATTATA

AGCCTGCAGTAATAAGGCTTAAAACAAGTGATCCTCGCAGGTACGATGCA

ATTTGTCCTAAAGCCGAGGAGTGGAAGATGGCATTAACTCTTTTTAAGTG

TTTGAAGAAGTTTTTTGATCTCACTGAACTCCTATCTGQTACTCAATATT

CCACTGCAAATTTATTTTACAAACGTTTCTGTGAGATAAAGGATTTGATT

GACCAATGGTGTGTTCATGAAAAATTTGTCATTAGGAGAATGGCCGTTGC

AATGAGTGAAAAGTTTGAGAAATATTGGAAAGTGTCTAATATTGCACTAG

CTGTAGCATGCTTCCTTGACCCTAGGTACAAGAAAATATTGATTGAGTTC

TATATGAAAAAATTTCATGGTGATTCATACAAAGTTCATGTAGATGACTT

TGTTAGGGTCATTAGAAAATTGTATCAATTCTATTCTAGTTGTAGTCCTT

CAGCTCCAAAGACAAAGCAACTACTAATGATAGTATGGATGATACCTTG

ATGGAAAATGAAGATGATGAATTTCAAAACTATTTGCATGAGTTGAAGGA

TTATGATCAAGTAGAGTCAAATGAATTGGATAAATATATGTCTGAACCCC

TTTTGAAGCATAGTGGTCAGTTTGATATTTTATCATGGTGGAGGGGAAGG

GTTGCAGAATATCCTATTCTCACCCAAATTGCAAGGGATGTGCTAGCAAT

ACAAGTGTCAACTGTTGCTTCTGAGTCTGCGTTCAGTGCTGGTGGTCGTG

TTGTTGATCCTTACCGCAATCGTCTTGGTTCGGAGATTGTTGAAGCTTTG

ATATGCACAAAAGATTGGGTAGCAGCATCTAGAAAAGGTGCTACATATTT

TCCAACAATGATTGGTGATCTCGAGGTGCTAGACTCTGTTATTGCTGCTG

CAACAAATCATGAGAATCATATGGATGAGGATGAAGACGCAATAGAATTT

TCTAAGAATAATGAAGATGTAGCAAGTGGCTCCTCTCCATGAGCAATGTG

TCTTATGTTTGTTGACAGATGAGCCTTGGTTGTAATAGTTTATGCATGCT

AAGTGCTCCAGATGTGAGCAAGTGATTATGAATATGTGTTTTAAACTTTA

TATTGTGTCATGTGTGCTAGTAGACTTATATGGCTTCTTATGTTAGCCAA

G bp 3067-6400, pEGFP-N1 plasmid fragment (bp 1400-4733):

(SEQ ID NO: 55)
gcggccgcgactctagatcataatcagccataccacatttgtagaggttt tacttgctttaaaaaacctcccacacctccccctgaacctgaaacataaa atgaatgcaattgttgttgttaacttgtttattgcagcttataatggtta caaataaagcaatagcatcacaaatttcacaaataaagcatttttttcac tgcattctagttgtggtttgtccaaactcatcaatgtatcttaaggcgta -continued aattgtaagcgttaatattttgttaaaattcgcgttaaattttttgttaaa
tcagctcattttttaaccaataggccgaaatcggcaaaatcccttataaa
tcaaaagaatagaccgagatagggttgagtgttgttccagtttggaacaa
gagtccactattaaagaacgtggactccaacgtcaaagggcgaaaaaccg
tctatcagggcgatggcccactacgtgaaccatcaccctaatcaagtttt
ttggggtcgaggtgccgtaaagcactaaatcggaaccctaaagggagccc
ccgatttagagcttgacggggaaagccggcgaacgtggcgagaaaggaag
ggaagaaagcgaaaggagcgggcgctagggcgctggcaagtgtagcggtc
acgctgcgcgtaaccaccacacccgccgcgcttaatgcgccgctacaggg
cgcgtcaggtggcacttttcggggaaatgtgcgcggaaccccctatttgtt
tattttctaaatacattcaaatatgtatccgctcatgagacaataaccc
tgataaatgcttcaataatattgaaaaaggaagagtcctgaggcggaaag
aaccagctgtggaatgtgtgtcagttagggtgtggaaagtccccaggctc
cccagcaggcagaagtatgcaaagcatgcatctcaattagtcagcaacca
ggtgtggaaagtccccaggctccccagcaggcagaagtatgcaaagcatg
catctcaattagtcagcaaccatagtcccgccctaactccgcccatccc
gcccctaactccgcccagttccgcccattctccgcccatggctgactaa
ttttttttatttatgcagaggccgaggccgcctcggcctctgagctattc
cagaagtagtgaggaggcttttttggaggcctaggcttttgcaaagatcg
atcaagagacaggatgaggatcgtttcgcatgattgaacaagatggattg
cacgcaggttctccggccgcttgggtggagaggctattcggctatgactg
ggcacaacagacaatcggctgctctgatgccgccgtgttccggctgtcag
cgcaggggcgcccggttcttttttgtcaagaccgacctgtccggtgccctg
aatgaactgcaagacgaggcagcgcggctatcgtggctggccacgacggg
cgttccttgcgcagctgtgctcgacgttgtcactgaagcgggaagggact
ggctgctattgggcgaagtgccggggcaggatctcctgtcatctcaccttc
gctcctgccgagaaagtatccatcatggctgatgcaatgcggcggctgca
tacgcctgatccggctacctgcccattcgaccaccaagcgaaacatcgca
tcgagcgagcacgtactcggatggaagccggtcttgtcgatcaggatgat
ctggacgaagagcatcaggggctcgcgccagccgaactgttcgccaggct
caaggcgagcatgcccgacggcgaggatctcgtcgtgacccatggcgatg
cctgcttgccgaatatcatggtggaaaatggccgcttttctggattcatc
gactgtggccggctgggtgtggcggaccgctatcaggacatagcgttggc
tacccgtgatattgctgaagagcttggcggcgaatgggctgaccgcttcc
tcgtgctttacggtatcgccgctcccgattcgcagcgcatcgccttctat
cgccttcttgacgagttcttctgagcgggactctggggttcgaaatgacc
gaccaagcgacgcccaacctgccatcacgagatttcgattccaccgccgc
cttctatgaaaggttgggcttcggaatcgttttccgggacgccggctgga
tgatcctccagcgcggggatctcatgctggagttcttcgcccaccctagg
gggaggctaactgaaacacggaaggagacaataccggaaggaacccgcgc -continued tatgacggcaataaaaagacagaataaaacgcacggtgttgggtcgtttg
ttcataaacgcggggttcggtcccagggctggcactctgtcgatacccca
ccgagacccattggggccaatacgcccgcgtttcttccttttccccacc
ccaccccccaagttcgggtgaaggcccagggctcgcagccaacgtcgggg
cggcaggccctgccatagcctcaggttactcatatatactttagattgat
ttaaaacttcattttttaattttaaaaggatctaggtgaagatcctttttga
taatctcatgaccaaaatcccttaacgtgagttttcgttccactgagcgt
cagacccgtagaaaagatcaaaggatcttcttgagatcctttttttctg
cgcgtaatctgctgcttgcaaacaaaaaaaccaccgctaccagcggtggt
ttgtttgccggatcaagagctaccaactctttttccgaaggtaactggct
tcagcagagcgcagataccaaatactgtccttctagtgtagccgtagtta
ggccaccacttcaagaactctgtagcaccgcctacatacctcgctctgct
aatcctgttaccagtggctgctgccagtggcgataagtcgtgtcttaccg
ggttggactcaagacgatagttaccggataaggcgcagcggtcgggctga
acggggggttcgtgcacacagcccagcttggagcgaacgacctacaccga
actgagatacctacagcgtgagctatgagaaagcgccacgcttcccgaag
ggagaaaggcggacaggtatccggtaagcggcagggtcggaacaggagag
cgcacgagggagcttccaggggggaaacgcctggtatctttatagtcctgt
cgggtttcgccacctctgacttgagcgtcgatttttgtgatgctcgtcag
gggggcggagcctatggaaaaacgccagcaacgcggcctttttacggttc
ctggccttttgctggccttttgctcacatgttctttcctgcgttatcccc
tgattctgtggataaccgtattaccgccatgcat The results of the analysis of Ds in three examples of transfected HEK293 cells are shown in FIG. 6. The Ds (lower case letters) in these three examples is flanked by human DNA (upper case letters) (not the vector DNA of the donor) starting from the first nucleotide immediately adjacent to the Ds end sequence. This demonstrates that Ds integrated into human genome via transposase-mediated mechanism. In case of DNA 2 insertion site is surrounded by classic 8 bp direct repeat that is often created when hAT transposons integrate into new locations.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Allen et al. (1988). "Transgene as probes for active chromosomal domains in mouse development." Nature 333:852-855.

Allende, M. L. et al. (1996). "Insertional mutagenesis in zebrafish identifies two novel genes, pescadillo and dead eye, essential for embryonic development." Genes Dev 10:3141-3155.

Altschul, S. F. et al., (1990). "Basic local alignment search tool." J Mol Biol 215:403-410.

Altschul, S. F. et al. (1997). "Gapped BLAST and PSI-BLAST: a new generation of protein database search programs." Nucleic Acids Res 25:3389-3402.

Amsterdam, A. et al. (1999). "A large-scale insertional mutagenesis screen in zebrafish." Genes Dev 13:2713-2724.

Andersen, J. K. et al. (1993). "Herpesvirus-mediated gene delivery into the rat brain: specificity and efficiency of the neuron-specific enolase promoter." Cell Mol Neurobiol 13:503-515.

Balciunas, D. et al. (2004). "Enhancer trapping in zebrafish using the Sleeping Beauty transposon." BMC Genomics 5:62(1-15).

Bellen, H. J. et al. (1989). "P-element-mediated enhancer detection: a versatile method to study development in Drosophila." Genes Dev 3:1288-1300.

Bingham, P. M. et al. (1981). "Cloning of DNA sequences from the white locus of D. melanogaster by a novel and general method." Cell 25:693-704.

Boehm, U. et al. (1995). "One of three nuclear localization signals of maize Activator (Ac) transposase overlaps the DNA-binding domain." Plant J 7:441-451.

Bunin, B. A. and Ellman, J. A. et al. (1992). "A general and expedient method for the solid-phase synthesis of 1,4-benzodiazepine derivatives." J. Am. Chem. Soc. 114:10997-10998.

Burns, J. C. et al. (1993). "Vesicular stomatitis virus G glycoprotein pseudotyped retroviral vectors: concentration to very high titer and efficient gene transfer into mammalian and nonmammalian cells." Proc Natl Acad Sci USA 90:8033-8037.

Carell, E. et al. (1994a). "A Novel Procedure for the Synthesis of Libraries Containing Small Organic Molecules." Angew. Chem. Int. Ed. Engl. 33:2059-2061.

Carell, E. et al. (1994b). "A Solution-Phase Screening Procedure for the Isolation of Active Compounds from a Library of Molecules." Angew. Chem. Int. Ed. Engl. 33:2061-2064.

Chen, T. T. and Powers, D. A. (1990). "Transgenic fish." Trends Biotechnol 8:209-215.

Chen, W. et al. (2002). "High-throughput selection of retrovirus producer cell lines leads to markedly improved efficiency of germ line-transmissible insertions in zebra fish." J Virol 76:2192-2198.

Childs, S. et al. (2000). "Zebrafish dracula encodes ferrochelatase and its mutation provides a model for erythropoietic protoporphyria." Curr Biol 10:1001-1004.

Cho, C. Y. et al. (1993). "An Unnatural biopolymer." Science. 261:1303-1305.

Clark, J. T. et al. (1984). "Neuropeptide Y and human pancreatic polypeptide stimulate feeding behavior in rats." Endocrinology 115:427-429.

Converse, A. D. et al. (2004). "Counterselection and co-delivery of transposon and transposase functions for Sleeping Beauty-mediated transposition in cultured mammalian cells." Biosci Rep 24:577-594.

Cull, M. G. et al. (1992). "Screening for Receptor Ligands Using Large Libraries of Peptides Linked to the C Terminus of the lac Repressor." Proc Natl Acad Sci USA 89:1865-1869.

Culp, P. et al. (1991). "High-frequency germ-line transmission of plasmid DNA sequences injected into fertilized zebrafish eggs." Proc Natl Acad Sci USA 88:7953-7957.

Cwirla, S. E. et al. (1990). "Peptides on Phage: A Vast Library of Peptides for Identifying Ligands." Proc. Natl. Acad. Sci. USA 87:6378-6382.

Davidson, A. E. (2003). "Efficient gene delivery and gene expression in zebrafish using the Sleeping Beauty transposon." Dev Biol 263:191-202.

Davidson, B. L. et al. (1993). "A model system for in vivo gene transfer into the central nervous system using an adenoviral vector." Nature Genetics 3:219-223.

Devlin, J. L. et al. (1990). "Random Peptide Libraries: A Source of Specific Protein Binding Molecules." Science 249:404-406.

Devon, R. S. et al. (1995). "Splinkerettes-improved vectorettes for greater efficiency in PCR walking." Nucl Acids Res 23:1644-1645.

DeWitt, S. H. et al. (1993). "Diversomers": An Approach to Nonpeptide, Nonoligomeric Chemical Diversity." Proc. Natl. Acad. Sci. USA 90:6909-6913.

Driever, W. et al. (1996). "A genetic screen for mutations affecting embryogenesis in zebrafish." Development 123: 37-46.

Dujon, B. et al. (1994). "Complete DNA sequence of yeast chromosome XI." Nature 369:371-378.

Ekker, S. C. (2000). "Morphants: a new systematic vertebrate functional genomics approach." Yeast 17:302-306.

Emi, N. et al. (1991). "Pseudotype formation of murine leukemia virus with the G protein of vesicular stomatitis virus." J Virol 65:1202-1207.

Erb, E. et al. (1994). "Recursive Deconvolution of Combinatorial Chemical Libraries." Proc. Natl. Acad. Sci. USA 91:11422-11426.

Erickson, J. C. et al. (1996). "Sensitivity to leptin and susceptibility to seizures of mice lacking neuropeptide Y." Nature 381:415-421.

Erzurum, S. C. et al. (1993). "Protection of human endothelial cells from oxidant injury by adenovirus-mediated transfer of the human catalase cDNA." Nucleic Acids Res 21:1607-1612.

Essner, J. J. et al. (2005). "Awakening gene therapy with Sleeping Beauty transposons." Curr Opin Pharmacol 5:513-519.

Fadool, J. M. et al. (1998). "Transposition of the mariner element from Drosophila mauritiana in zebrafish." Proc Natl Acad Sci USA 95:5182-5186.

Fedoroff, N. et al. (1983). Isolation of the transposable maize controlling elements Ac and Ds. *Cell* 35:235-242.

Felici, F. et al. (1991). "Selection of antibody ligands from a large library of oligopeptides expressed on a multivalent exposition vector." *J. Mol. Biol.* 222:301-310.

Fletcher, G. L., and Davis, P. L. (1991). "Transgenic fish for aquaculture." In *Genetic Engineering*, Setlow, J. K., ed., Plenum Press.

Flotte, T. R. et al. (1993). "Stable in vivo expression of the cystic fibrosis transmembrane conductance regulator with an adeno-associated virus vector." *Proc Natl Acad Sci USA* 90:10613-10617.

Fodor, S. et al. (1993). "Multiplexed biochemical assays with biological chips." *Nature* 364:555-556.

Gallop, M. A. et al. (1994). "Applications of combinatorial technologies to drug discovery. 1. Background and peptide combinatorial libraries." *J. Med. Chem.* 37:1233-1251.

Golling, G. et al. (2002). "Insertional mutagenesis in zebrafish rapidly identifies genes essential for early vertebrate development." *Nat Genet.* 31:135-140.

Gong, Z. et al. (2002). "Green fluorescent protein expression in germ-line transmitted transgenic zebrafish under a stratified epithelial promoter from keratin8." *Dev Dyn* 223:204-215.

Gossler et al. (1989). "Mouse Embryonic Stem Cells and Reporter Constructs to Detect Developmentally Regulated Genes." *Science* 244:463-465.

Graham, M., et al. (1997). "Overexpression of Agrt leads to obesity in transgenic mice." *Nat Genet.* 17:273-274.

Hackett, P. B. et al. (2005). "Sleeping beauty transposon-mediated gene therapy for prolonged expression." *Adv Genet* 54:189-232.

Haffter, P. et al. (1996). "The identification of genes with unique and essential functions in the development of the zebrafish *Danio rerio*." *Development* 123:1-36.

Halford, J. C. (2001). "Pharmacology of appetite suppression: implication for the treatment of obesity." *Curr Drug Targets* 2:353-370.

Hay, B. A. et al. (1997). "P element insertion-dependent gene activation in the *Drosophila* eye." *Proc Natl Acad Sci USA* 94:5195-5200.

Heasman, J. (2002). "Morpholino oligos: making sense of antisense?" *Dev Biol* 243:209-214.

Heinlein, M. et al. (1994). "In vivo aggregation of maize Activator (Ac) transposase in nuclei of maize endosperm and Petunia protoplasts." *Plant J* 5:705-714.

Horie, K. et al. (2001). "Efficient chromosomal transposition of a Tc1/mariner-like transposon Sleeping Beauty in mice." *Proc Natl Acad Sci USA.* 98:9191-9196.

Horwell, D. et al (1996). "'Targeted' molecular diversity: design and development of non-peptide antagonists for cholecystokinin and tachykinin receptors." *Immunopharmacology* 33:68-72.

Houba-Herin, N. et al. (1990). "Excision of a Ds-like maize transposable element (Ac delta) in a transient assay in Petunia is enhanced by a truncated coding region of the transposable element Ac." *Mol Gen Genet.* 224:17-23.

Houghten, R. A. et al. (1992). "The use of synthetic peptide combinatorial libraries for the identification of bioactive peptides." *Biotechniques* 13:412-421.

Izsvak, Z. and Z. Ivics (1993). "Two-stage ligation-mediated PCR enhances the detection of integrated transgenic DNA." *Biotechniques* 15:814-818.

Izsvak, Z. and Z. Ivics (2004). "Sleeping beauty transposition: biology and applications for molecular therapy." *Mol Ther* 9:147-156.

Kaiser, K. et al. (1995). "Eukaryotic transposable elements as tools to study gene structure and function." In *Mobile Genetic Elements*, Sheratt, D. J., ed., Oxford University Press, Oxford, pp. 69-100.

Kaminski, J. M. et al. (2002). "Design of a nonviral vector for site-selective, efficient integration into the human genome." *FASEB J* 16:1242-1247.

Kawakami, K. and T. Noda (2004). "Transposition of the Tol2 element, an Ac-like element from the Japanese medaka fish *Oryzias latipes*, in mouse embryonic stem cells." *Genetics.* 166:895-899.

Kawakami, K. et al. (2000). "Identification of a functional transposase of the Tol2 element, an Ac-like element from the Japanese medaka fish, and its transposition in the zebrafish germ lineage." *Proc Natl Acad Sci USA* 97:11403-11408.

Kawakami, K. et al. (2004). "Excision of the Tol2 transposable element of the medaka fish *Oryzias latipes* in *Xenopus laevis* and *Xenopus tropicalis*." *Gene* 338:93-98.

Kimmel, C. B. (1989). "Genetics and Early Development of Zebrafish." *Trends Genet.* 5:283-288.

Koga, A. et al. (2002). "Gene transfer and coining of flanking chromosomal regions using the medaka fish Tol2 transposable element." *Mar Biotechnol (NY)* 4:6-11.

Kothary et al. (1988). "A transgene containing lacZ inserted into the dystonia locus is expressed in neural tube." *Nature* 335:435-437.

Krieg, P. A. and D. A. Melton (1984). "Functional messenger RNAs are produced by SP6 in vitro transcription of cloned cDNAs." *Nucleic Acids Res* 12:7057-7070.

Lam, K. S. (1997). "Application of combinatorial library methods in cancer research and drug discovery." *Anticancer Drug Des.* 12:145-167.

Lam, K. S. et al. (1991). "A new type of synthetic peptide library for identifying ligand-binding activity." *Nature* 354:82-84.

Lander, E. S. et al. (2001). "Initial sequencing and analysis of the human genome." *Nature* 409:860-921.

Levine, A. S. and J. E. Morley (1984). "Neuropeptide Y: a potent inducer of consummatory behavior in rats." *Peptides* 5:1025-1029.

Lever, A. M. (2000). "Lentiviral vectors: progress and potential." *Curr Opin Mol Ther* 2:488-496.

Lin, S. et al. (1994). "Integration and germ-line transmission of a pseudotyped retroviral vector in zebrafish." *Science* 265:666-669.

Liu, L. et al. (2005). "Endothelial targeting of the Sleeping Beauty transposon within lung." *Mol Ther* 10:97-105.

Liu, L. et al. (2006). "Sustained FVIII Expression and Phenotypic Correction of Hemophilia A in Neonatal Mice Using an Endothelial-Targeted Sleeping Beauty Transposon." *Mol Ther February* 3; [Epub ahead of print].

Liu, Y. G. and R. F. Whittier (1995). "Thermal asymmetric interlaced PCR: automatable amplification and sequencing of insert end fragments from P1 and YAC clones for chromosome walking." *Genomics* 25:674-81.

Lu, J. K. et al. (1992). "Integration, expression and germ-line transmission of foreign growth hormone genes in medaka (*Oryzias latipes*)." *Molec Mar Biol Biotechnol* 1:366-375.

Miklos, G. L. and G. M. Rubin (1996). "The role of the genome project in determining gene function: insights from model organisms." *Cell* 86:521-529.

Miller, A. D. et al., (1993). "Use of retroviral vectors for gene transfer and expression." *Methods of Enzymology* 217:581-599.

Mooslehner, K. et al. (1990). "Retroviral integration sites in transgenic Mov mice frequently map in the vicinity of transcribed DNA regions." *J Virol* 64:3056-3058.

Nasevicius, A. and S. C. Ekker (2000). "Effective targeted gene 'knockdown' in zebrafish." *Nat Genet.* 26:216-220.

Ohlfest, J. E. et al. (2005). "Nonviral vectors for cancer gene therapy: prospects for integrating vectors and combination therapies." *Curr Gene Ther* 5:629-641.

Ollmann, M. M. et al. (1997). "Antagonism of central melanocortin receptors in vitro and in vivo by agouti-related protein." *Science* 278:135-138.

O'Kane, et al. (1987). "Detection in situ of Genomic Regulatory Elements in *Drosophila*." *Proc. Natl. Acad. Sci. USA* 84:9123-9127.

Osborne, B. I. and B. Baker (1995). "Movers and shakers: maize transposons as tools for analyzing other plant genomes." *Curr Opin Cell Biol* 7:406-413.

Parinov, S. et al. (1999). "Analysis of flanking sequences from Dissociation 4U insertion lines: a database for reverse genetics in *Arabidopsis*." *Plant Cell* 11:2263-2270.

Parinov, S. et al. (2004). "Enhancer trap transposable element as a tool for identification of developmentally regulated genes in zebrafish in vivo." *Dev Dyn.* 231:449-459.

Plasterk, R. H. (1993). "Molecular mechanisms of transposition and its control." *Cell* 74:781-786.

Pohhnan, R. F. et al. (1984). The nucleotide sequence of the maize controlling element Activator. *Cell* 37:635-643.

Powers, D. A. et al. (1992). "Electroporation: a method for transferring genes into the gametes of zebrafish (*Brachydanio rerio*), channel catfish (*Ictalurus punctatus*), and common carp (*Cyprinus carpio*)." *Molec Mar Biol Biotechnol* 1:301-308.

Qian, S. et al. (2002). "Neither agouti-related protein nor neuropeptide Y is critically required for the regulation of energy homeostasis in mice." *Mol Cell Biol* 22:5027-5035.

Raz, E. et al. (1998). "Transposition of the nematode *Caenorhabditis elegans* Tc3 element in the zebrafish *Danio rerio*." *Curr Biol* 8:82-88.

Richardson, P. D. et al. (2002). "Gene repair and transposon-mediated gene therapy." *Stem Cells* 20:105-118.

Rohdewohld, H. et al. (1987). "Retrovirus integration and chromatin structure: Moloney murine leukemia proviral integration sites map near DNase I-hypersensitive sites." *J Virol* 61:336-343.

Rorth, P. (1996). "A modular misexpression screen in *Drosophila* detecting tissue-specific phenotypes." *Proc Natl Acad Sci USA* 93:12418-12422.

Rorth, P. et al. (1998). "Systematic gain-of-function genetics in *Drosophila*." *Development* 125:1049-1057.

Sakaguchi, T. et al. (2001). "A novel sox gene, 226D7, acts downstream of Nodal signaling to specify endoderm precursors in zebrafish." *Mech Dev* 107:25-38.

Sambrook et al. (1989). *Molecular Cloning*, 2nd Ed., Cold Spring Harbor Laboratory Press, Cold Spring Harbor, N.Y.

Scherdin, U. et al. (1990). "Transcriptionally active genome regions are preferred targets for retrovirus integration." *J Virol* 64:907-912.

Scott, J. K. and J. P. Smith (1990). "Searching for Peptide Ligands with an Epitope Library." *Science* 249:386-390.

Shapiro, J. A. (1992). "Natural genetic engineering in evolution." *Genomics* 86:99-111.

Shure, M. et al. (1983). Molecular identification and isolation of the Waxy locus in maize. *Cell* 35:225-233.

Spradling, A. C. et al. (1995). "Gene disruptions using P transposable elements: an integral component of the *Drosophila* genome project." *Proc Natl Acad Sci USA* 92:10824-10930.

Streisinger (1984). Attainment of Minimal Biological Variability and Measurements of Genotoxicity: Production of Homozygous Diploid Zebra Fish. *Natl. Cancer Inst. Monogr.* 65:53-58.

Sulston, J. et al. (1992). "The *C. elegans* genome sequencing project: a beginning." *Nature* 356:37-41.

Summerton, J. and D. Weller (1997). "Morpholino antisense oligomers: design, preparation, and properties." *Antisense Nucleic Acid Drug Dev* 7:187-195.

Summerton, J. et al. (1997). "Morpholino and phosphorothioate antisense oligomers compared in cell-free and in-cell systems." *Antisense Nucleic Acid Drug Dev* 7:63-70.

Talbot, W. S. and N. Hopkins (2000). "Zebrafish mutations and functional analysis of the vertebrate genome." *Genes Dev* 14:755-762.

Tsang, M. et al. (2002). "Identification of Sef, a novel modulator of FGF signalling." *Nat Cell Biol* 4:165-169.

Venter, J. C. et al. (2001). "The sequence of the human genome." *Science* 291:1304-1351.

Vijaya, S. et al. (1986). "Acceptor sites for retroviral integrations map near DNase I-hypersensitive sites in chromatin." *J Virol* 60:683-692.

Weil, C. F. and R. Kunze (2000). "Transposition of maize Ac/Ds transposable elements in the yeast *Saccharomyces cerevisiae*." *Nat Genet.* 26:187-190.

Westerfield, M. (2000). *The Zebrafish Book: A guide for the laboratory use of Zebrafish (Danio rerio)*, 4th ed., University of Oregon Press, Eugene.

Wienholds, E. et al. (2002). "Target-Selected Inactivation of the Zebrafish rag1 Gene." *Science* 297:99-102.

Yee, J. K. et al. (1994). "A general method for the generation of high-titer, pantropic retroviral vectors: highly efficient infection of primary hepatocytes." *Proc Natl Acad Sci USA* 91:9564-9568.

Zabner, J. et al. (1994). "Safety and efficacy of repetitive adenovirus-mediated transfer of CFTR cDNA to airway epithelia of primates and cotton rats." *Nature Genetics* 6:75-83.

Zhang, G. et al. (1996). "An enhanced green fluorescent protein allows sensitive detection of gene transfer in mammalian cells." *Biochem Biophys Res Commun* 227:707-711.

Zuckermann, R. N. (1994). "Discovery of nanomolar ligands for 7-transmembrane G-protein-coupled receptors from a diverse N-(substituted)glycine peptoid library." *J. Med. Chem.* 37:2678-2685.

What is claimed is:

1. A method of integrating a polynucleotide into the DNA of a vertebrate cell comprising:
introducing into the vertebrate cell a modified Ac transposase or a nucleic acid encoding the modified Ac transposase, wherein the modified Ac transposase comprises (i) a nuclear localization signal (NLS) and (ii) a truncated Ac transposase, wherein the NLS is fused to the N-terminus of the truncated Ac transposase, wherein the NLS localizes a transposition reaction to the nucleus of the vertebrate cell and wherein the truncated Ac transposase comprises the amino acid sequence set forth in SEQ ID NO:8 and catalyzes the integration of the polynucleotide into the DNA of the vertebrate cell, wherein the NLS comprises the amino acid sequence set forth in SEQ ID NO:2 or the amino acid sequence set forth in SEQ ID NO:9;
introducing into the vertebrate cell a nucleic acid fragment comprising the polynucleotide positioned between 5' end and 3' end cis-required sequences of a Ds element that bind to the modified Ac transposase; and
integrating the polynucleotide into the DNA of the vertebrate cell.

2. The method of claim 1, wherein the 5' end and 3' end cis-required sequences of the Ds element are selected from the group consisting of:
(a) 5' end and 3' end cis-required sequences that are part of a Ds element;
(b) the Ds 5' end cis-required sequence having the nucleotide sequence set forth in SEQ ID NO:45 and the Ds 3' end cis-required sequence having the nucleotide sequence set forth in SEQ ID NO:49; and
(c) the Ds 5' end cis-required sequence having the nucleotide sequence set forth in nucleotides 3657-3903 of SEQ ID NO:1 and the Ds 3' end cis-required sequence having the nucleotide sequence set forth in nucleotides 43-412 of SEQ ID NO:1.

3. The method of claim 1, wherein the nucleic acid encoding the modified Ac transposase is introduced into a vertebrate cell and stably integrated into its genome before the nucleic acid fragment containing the Ds 5' end and 3' end cis-required sequences is introduced into the vertebrate cell.

4. The method of claim 1, wherein the modified Ac transposase is introduced into the vertebrate cell.

5. The method of claim 1, wherein the nucleic acid encoding the modified Ac transposase is introduced into the vertebrate cell.

6. The method of claim 1, wherein the nucleic acid fragment is part of a vector.

7. The method of claim 1, wherein the polynucleotide comprises at least a portion of an open reading frame.

8. The method of claim 1, wherein the polynucleotide comprises at least one expression control region.

9. The method of claim 8, wherein the expression control region is selected from the group consisting of a promoter, an enhancer or a silencer.

10. The method of claim 1, wherein the polynucleotide comprises a promoter operably linked to at least a portion of an open reading frame.

11. The method of claim 1, wherein the DNA into which the polynucleotide is capable of integrating is the cell genome.

12. The method of claim 1, wherein introducing the polynucleotide to the cell comprises using a method selected from the group consisting of microinjection, electroporation, combining the nucleic acid fragment with cationic lipid vesicles or DNA condensing reagents, and incorporating the nucleic acid fragment into a viral vector and contacting the viral vector with the cell.

13. The method of claim 1, wherein the NLS comprises the amino acid sequence set forth in SEQ ID NO:2.

14. The method of claim 1, wherein the NLS comprises the amino acid sequence set forth in SEQ ID NO:9.

15. The method of claim 3, wherein the nucleic acid comprises the nucleotide sequence set forth in SEQ ID NO:10 or the nucleotide sequence set forth in SEQ ID NO:36.

16. The method of claim 15, wherein the nucleic acid comprises the nucleotide sequence set forth in SEQ ID NO:10.

17. The method of claim 15, wherein the nucleic acid comprises the nucleotide sequence set forth in SEQ ID NO:36.

18. The method of claim 5, wherein the nucleic acid is an RNA.

19. The method of claim 5, wherein the nucleic acid is a DNA.

20. The method of claim 19, wherein the nucleic acid comprises the nucleotide sequence set forth in SEQ ID NO:10 or the nucleotide sequence set forth in SEQ ID NO:36.

21. The method of claim 20, wherein the nucleic acid comprises the nucleotide sequence set forth in SEQ ID NO:10.

22. The method of claim 20, wherein the nucleic acid comprises the nucleotide sequence set forth in SEQ ID NO:36.

23. The method of claim 13, wherein the modified Ac transposase comprises the amino acid sequence set forth in SEQ ID NO:20.

24. The method of claim 14, wherein the modified Ac transposase comprises the amino acid sequence set forth in SEQ ID NO:44.

25. The method of claim 9, wherein the promoter comprises the nucleotide sequence set forth in nucleotides 436-2674 of SEQ ID NO:1.

26. The method of claim 10, wherein the promoter comprises the nucleotide sequence set forth in nucleotides 436-2674 of SEQ ID NO:1.

27. The method of claim 1, wherein the vertebrate cell is selected from the group consisting of a pluripotent cell, a totipotent cell, an oocyte, a lymphocyte, a hepatocyte, a neural cell, a muscle cell and a blood cell.

28. The method of claim 1, wherein the vertebrate cell is a cell of an egg or a cell of an embryo.

29. The method of claim 1, wherein the vertebrate is selected from the group consisting of a fish, a bird or a mammal.

30. The method of claim 29, wherein the fish is selected from the group consisting of salmon, trout, tuna, halibut, catfish, zebrafish, medaka, carp, tilapia, goldfish, and loach.

31. The method of claim 30, wherein the fish is zebrafish.

* * * * *